US007244609B2

(12) United States Patent
Drocourt et al.

(10) Patent No.: US 7,244,609 B2
(45) Date of Patent: Jul. 17, 2007

(54) SYNTHETIC GENES AND BACTERIAL PLASMIDS DEVOID OF CPG

(75) Inventors: Daniel Drocourt, Saint Orens de Gameville (FR); Jean Paul Reynes, Escalquens (FR); Gerard Tiraby, Toulouse (FR)

(73) Assignee: Cayla, Toulouse Cedex (FR)

( * ) Notice: Subject to any disclaimer, the term of this patent is extended or adjusted under 35 U.S.C. 154(b) by 415 days.

(21) Appl. No.: 10/469,851

(22) PCT Filed: Mar. 11, 2002

(86) PCT No.: PCT/FR02/00862

§ 371 (c)(1),
(2), (4) Date: Sep. 5, 2003

(87) PCT Pub. No.: WO02/072846

PCT Pub. Date: Sep. 19, 2002

(65) Prior Publication Data

US 2004/0219677 A1 Nov. 4, 2004

(30) Foreign Application Priority Data

Mar. 9, 2001 (FR) .................................. 01 03274

(51) Int. Cl.
*C12N 1/20* (2006.01)
*C12N 15/00* (2006.01)
*C12N 15/64* (2006.01)
*C07H 21/04* (2006.01)

(52) U.S. Cl. ............................ 435/252.33; 435/320.1; 435/91.4; 536/24.1

(58) Field of Classification Search ..................... None
See application file for complete search history.

(56) References Cited

FOREIGN PATENT DOCUMENTS

| WO | 00/14262 A | 3/2000 |
|---|---|---|
| WO | 01/40478 A | 6/2001 |

OTHER PUBLICATIONS

Krieg et al., PRoc. Natl. Acad. Sci. USA, vol. 95, pp. 12631-12636, 1998.*

Campbell et al., PNAS (1999) 96, 9184-9.

Krieg et al. Immunopharmacology (2000) 48, 303-305.

Palmer et al., Gene (1994) 143, 1-12.

Filutowicz et al., Gene (1998) 223, 195-204.

Hershberg et al, "PromEC: An updated database of *E. coli*. mRNA promoters with experimentallyidentified transcriptional start sites" Promec index, printed from internet web site "bioinfo.md.huji.ac.il/marg/promec" on Dec. 12, 2003.

Isabelle Henry et al; "LagoZ et LagZ, Deux Genes Appauvris en Dinucleotides CpG Derives du Gene LacZ Pour L'Etude des Controles Epigenetiques"; C.R. Acd. Sci. Paris, vol. 322, 1999, pp. 1061-1070, XP002185406.

Thomas R Skpek et al; "Synthesis of a Laci Gene Analogue With Reduced CpG Content"; Mutation Research, vol. 349, 1996, pp. 163-172, XP001041417.

Thomas Skopek et al; "Effect of Target Gene CpG Content on Spontaneous Mutation in Transgenic Mice"; vol. 400, 1998, pp. 77-88, XP001030795.

Base de donnes EMBL' Numero d'acces L37432; Apr. 10, 1996, Tiraby G. et al; "New Suicide Genes and New Associations of Pyrimidine Nucleobase and Nucleoside Analogs With New Suicide Genes for a Gene Therapy of Acquired Disease"; XP002185408.

Pritam Sengupta et al; "Methylation in the Initiation Region of the First Exon Supresses Collagen Pre-Alpha2(I) Gene Transcription"; Biochimica ET Biophysica ACTA, vol. 1443, 1998, pp. 75-89, Xpoo2185407.

Richard S. Hale et al; "Codon Optimization of the Gene Encoding a Domain From Human Type 1 Neurofibromin Protein Results in a Threefold Improvement in Expression Level in *Escherichia coli*"; Protein Expression and Purification, vol. 12, Mar. 1998, pp. 185-188, XP001030791.

Martin Hug et al; Transcriptional Repression by Methylation"Cooperativity Between a CpG Cluster in the Promoter and Remote CpG-Rich Regions"; FEBS Letters, vol. 379, 1996, pp. 251-254, XP002125021.

Igor Levchenko et al; "Initiator Protein PI can Bind Independently to Two Domains of the Gamma Origin Core of Plasmid R6K" the Direct Repeats and the A+T-Rich Segment; Nucleic Acids Research, vol. 24, No. 10, 1996, pp. 1936-1942, XP002185270.

* cited by examiner

*Primary Examiner*—Nancy Vogel
(74) *Attorney, Agent, or Firm*—Nixon & Vanderhye P.C.

(57) ABSTRACT

The invention relates to a new series of bacterial plasmid vectors which are fully devoid of CpG and which can express synthetic genes which do not contain CpG in the bacteria *Escherichia coli.*

12 Claims, 27 Drawing Sheets

```
     NcoI
1    CCATGGCCAAGTTGACCAGTGCTGTCCCAGTGCTCACAGCCAGGGATGTGGCTGGAGCT
1       MetAlaLysLeuThrSerAlaValProValLeuThrAlaArgAspValAlaGlyAla

60   GTTGAGTTCTGGACTGACAGGTTGGGGTTCTCCAGAGATTTTGTGGAGGATGACTTTGCA
20   ValGluPheTrpThrAspArgLeuGlyPheSerArgAspPheValGluAspAspPheAla

120  GGTGTGGTCAGAGATGATGTCACCCTGTTCATCTCAGCAGTCCAGGACCAGGTGGTGCCT
40   GlyValValArgAspAspValThrLeuPheIleSerAlaValGlnAspGlnValValPro

180  GACAACACCCTGGCTTGGGTGTGGGTGAGAGGACTGGATGAGCTGTATGCTGAGTGGAGT
60   AspAsnThrLeuAlaTrpValTrpValArgGlyLeuAspGluLeuTyrAlaGluTrpSer

240  GAGGTGGTCTCCACCAACTTCAGGGATGCCAGTGGCCCTGCCATGACAGAGATTGGAGAG
80   GluValValSerThrAsnPheArgAspAlaSerGlyProAlaMetThrGluIleGlyGlu

300  CAGCCCTGGGGGAGAGAGTTTGCCCTGAGAGACCCAGCAGGCAACTGTGTGCACTTTGTG
100  GlnProTrpGlyArgGluPheAlaLeuArgAspProAlaGlyAsnCysValHisPheVal
                                     NheI
360  GCAGAGGAGCAGGACTGAGGATAAGAATTCAGCTAGC           SEQ ID No.1
120  AlaGluGluGlnAsp***                              SEQ ID No.2
```

Figure 1

| Oligo | SEQ ID |
|---|---|
| OL26099:AACTCAGCTGAGGAGGCAGACCATGGCCAAGTTGACCAGT | SEQ ID No.16 |
| OL26199:GCTGTCCCAGTGCTCACAGCCAGGGATGTGGCTGGAGCTG | SEQ ID No.17 |
| OL26299:TTGAGTTCTGGACTGACAGGTTGGGGTTCTCCAGAGATTT | SEQ ID No.18 |
| OL26399:TGTGGAGGATGACTTTGCAGGTGTGGTCAGAGATGATGTC | SEQ ID No.19 |
| OL26499:ACCCTGTTCATCTCAGCAGTCCAGGACCAGGTGGTGCCTG | SEQ ID No.20 |
| OL26599:ACAACACCCTGGCTTGGGTGTGGGTGAGAGGACTGGATGA | SEQ ID No.21 |
| OL26699:GCTGTATGCTGAGTGGAGTGAGGTGGTCTCCACCAACTTC | SEQ ID No.22 |
| OL26799:AGGGATGCCAGTGGCCCTGCCATGACAGAGATTGGAGAGC | SEQ ID No.23 |
| OL26899:AGCCCTGGGGGAGAGAGTTTGCCCTGAGAGACCCAGCAGG | SEQ ID No.24 |
| OL26999:CAACTGTGTGCACTTTGTGGCAGAGGAGCAGGACTGAGGA | SEQ ID No.25 |
| OL27099:TAAGAATTCAGCTAGCTCGAC | SEQ ID No.26 |
| OL27199:GTCGAGCTAGCTGAATTCTTATCCTCAGTCCTGCTCCTCTG | SEQ ID No.27 |
| OL27299:CCACAAAGTGCACACAGTTGCCTGCTGGGTCTCTCAGGGC | SEQ ID No.28 |
| OL27399:AAACTCTCTCCCCCAGGGCTGCTCTCCAATCTCTGTCATG | SEQ ID No.29 |
| OL27499:GCAGGGCCACTGGCATCCCTGAAGTTGGTGGAGACCACCT | SEQ ID No.30 |
| OL27599:CACTCCACTCAGCATACAGCTCATCCAGTCCTCTCACCCA | SEQ ID No.31 |
| OL27699:CACCCAAGCCAGGGTGTTGTCAGGCACCACCTGGTCCTGG | SEQ ID No.32 |
| OL27799:ACTGCTGAGATGAACAGGGTGACATCATCTCTGACCACAC | SEQ ID No.33 |
| OL27899:CTGCAAAGTCATCCTCCACAAAATCTCTGGAGAACCCCAA | SEQ ID No.34 |
| OL27999:CCTGTCAGTCCAGAACTCAACAGCTCCAGCCACATCCCTG | SEQ ID No.35 |
| OL28099:GCTGTGAGCACTGGGACAGCACTGGTCAACTTGGCCATGG | SEQ ID No.36 |
| OL28199:TCTGCCTCCTCAGCTGAGTT | SEQ ID No.37 |

Figure 2

```
      BspHI
   1  TCATGAAGAAACCTGAACTGACAGCAACTTCTGTTGAGAAGTTTCTCATTGAAAAATTT
   1    MetLysLysProGluLeuThrAlaThrSerValGluLysPheLeuIleGluLysPhe

  60 GATTCTGTTTCTGATCTCATGCAGCTGTCTGAAGGTGAAGAAAGCAGAGCCTTTTCTTTT
  20 AspSerValSerAspLeuMetGlnLeuSerGluGlyGluGluSerArgAlaPheSerPhe

 120 GATGTTGGAGGAAGAGGTTATGTTCTGAGGGTCAATTCTTGTGCTGATGGTTTTTACAAA
  40 AspValGlyGlyArgGlyTyrValLeuArgValAsnSerCysAlaAspGlyPheTyrLys

 180 GACAGATATGTTTACAGACACTTTGCCTCTGCTGCTCTGCCAATTCCAGAAGTTCTGGAC
  60 AspArgTyrValTyrArgHisPheAlaSerAlaAlaLeuProIleProGluValLeuAsp

 240 ATTGGAGAATTTTCTGAATCTCTCACCTACTGCATCAGCAGAAGAGCACAAGGAGTCACT
  80 IleGlyGluPheSerGluSerLeuThrTyrCysIleSerArgArgAlaGlnGlyValThr

 300 CTCCAGGATCTCCCTGAAACTGAGCTGCCAGCTGTTCTGCAACCTGTTGCTGAAGCAATG
 100 LeuGlnAspLeuProGluThrGluLeuProAlaValLeuGlnProValAlaGluAlaMet

 360 GATGCCATTGCAGCAGCTGATCTGAGCCAAACCTCTGGATTTGGTCCTTTTGGTCCCCAA
 120 AspAlaIleAlaAlaAlaAspLeuSerGlnThrSerGlyPheGlyProPheGlyProGln

 420 GGCATTGGTCAGTACACCACTTGGAGGGATTTCATTTGTGCCATTGCTGATCCTCATGTC
 140 GlyIleGlyGlnTyrThrThrTrpArgAspPheIleCysAlaIleAlaAspProHisVal

 480 TATCACTGGCAGACTGTGATGGATGACACAGTTTCTGCTTCTGTTGCTCAGGCACTGGAT
 160 TyrHisTrpGlnThrValMetAspAspThrValSerAlaSerValAlaGlnAlaLeuAsp

 540 GAACTCATGCTGTGGGCAGAAGATTGTCCTGAAGTCAGACACCTGGTCCATGCTGATTTT
 180 GluLeuMetLeuTrpAlaGluAspCysProGluValArgHisLeuValHisAlaAspPhe

 600 GGAAGCAACAATGTTCTGACAGACAATGGCAGAATCACTGCAGTCATTGACTGGTCTGAA
 200 GlySerAsnAsnValLeuThrAspAsnGlyArgIleThrAlaValIleAspTrpSerGlu

 660 GCCATGTTTGGAGATTCTCAATATGAGGTTGCCAACATTTTTTTTTGGAGACCTTGGCTG
 220 AlaMetPheGlyAspSerGlnTyrGluValAlaAsnIlePhePheTrpArgProTrpLeu

 720 GCTTGCATGGAACAACAAACAAGATATTTTGAAAGAAGACACCCAGAACTGGCTGGTTCC
 240 AlaCysMetGluGlnGlnThrArgTyrPheGluArgArgHisProGluLeuAlaGlySer

 780 CCCAGACTGAGAGCCTACATGCTCAGAATTGGCCTGGACCAACTGTATCAATCTCTGGTT
 260 ProArgLeuArgAlaTyrMetLeuArgIleGlyLeuAspGlnLeuTyrGlnSerLeuVal

 840 GATGGAAACTTTGATGATGCTGCTTGGGCACAAGGAAGATGTGATGCCATTGTGAGGTCT
 280 AspGlyAsnPheAspAspAlaAlaTrpAlaGlnGlyArgCysAspAlaIleValArgSer

 900 GGTGCTGGAACTGTTGGAAGAACTCAAATTGCAAGAAGGTCTGCTGCTGTTTGGACTGAT
 300 GlyAlaGlyThrValGlyArgThrGlnIleAlaArgArgSerAlaAlaValTrpThrAsp

 960 GGATGTGTTGAAGTTCTGGCTGACTCTGGAAACAGGAGACCCTCCACAAGACCCAGAGCC
 320 GlyCysValGluValLeuAlaAspSerGlyAsnArgArgProSerThrArgProArgAla

                     NheI
1020 AAGGAATGAATATTAGCTAGC                          SEQ.ID.No.3
 340 LysGlu***                                      SEQ ID No 4
```

Figure 3

HS01:TGAGATCACCGGTTCAGCTGAGGAGGCACATCATGAAGAAACCTGAACTGACAGCAACTT SEQ ID No.38
HS02:CTGTTGAGAAGTTTCTCATTGAAAAATTTGATTCTGTTTCTGATCTCATGCAGCTGTCTG SEQ ID No.39
HS03:AAGGTGAAGAAAGCAGAGCCTTTTCTTTTGATGTTGGAGGAAGAGGTTATGTTCTGAGGG SEQ ID No.40
HS04:TCAATTCTTGTGCTGATGGTTTTTACAAAGACAGATATGTTTACAGACACTTTGCCTCTG SEQ ID No.41
HS05:CTGCTCTGCCAATTCCAGAAGTTCTGGACATTGGAGAATTTTCTGAATCTCTCACCTACT SEQ ID No.42
HS06:GCATCAGCAGAAGAGCACAAGGAGTCACTCTCCAGGATCTCCCTGAAACTGAGCTGCCAG SEQ ID No.43
HS07:CTGTTCTGCAACCTGTTGCTGAAGCAATGGATGCCATTGCAGCAGCTGATCTGAGCCAAA SEQ ID No.44
HS08:CCTCTGGATTTGGTCCTTTTGGTCCCCAAGGCATTGGTCAGTACACCACTTGGAGGGATT SEQ ID No.45
HS09:TCATTTGTGCCATTGCTGATCCTCATGTCTATCACTGGCAGACTGTGATGGATGACACAG SEQ ID No.46
HS10:TTTCTGCTTCTGTTGCTCAGGCACTGGATGAACTCATGCTGTGGCAGAAGATTGTCCTG SEQ ID No.47
HS11:AAGTCAGACACCTGGTCCATGCTGATTTTGGAAGCAACAATGTTCTGACAGACAATGGCA SEQ ID No.48
HS12:GAATCACTGCAGTCATTGACTGGTCTGAAGCCATGTTTGGAGATTCTCAATATGAGGTTG SEQ ID No.49
HS13:CCAACATTTTTTTTTGGAGACCTTGGCTGGCTTGCATGGAACAACAAACAAGATATTTTG SEQ ID No.50
HS14:AAAGAAGACACCCAGAACTGGCTGGTTCCCCCAGACTGAGAGCCTACATGCTCAGAATTG SEQ ID No.51
HS15:GCCTGGACCAACTGTATCAATCTCTGGTTGATGGAAACTTTGATGATGCTGCTTGGGCAC SEQ ID No.52
HS16:AAGGAAGATGTGATGCCATTGTGAGGTCTGGTGCTGGAACTGTTGGAAGAACTCAAATTG SEQ ID No.53
HS17:CAAGAAGGTCTGCTGCTGTTTGGACTGATGGATGTGTTGAAGTTCTGGCTGACTCTGGAA SEQ ID No.54
HS18:ACAGGAGACCCTCCACAAGACCCAGAGCCAAGGAATGAATATTAGCTAGCGGATCCTGAG SEQ ID No.55
HS19:CTCAGGATCCGCTAGCTAATATTCATTCCT SEQ ID No.56
HS20:TGGCTCTGGGTCTTGTGGAGGGTCTCCTGTTTCCAGAGTCAGCCAGAACTTCAACACATC SEQ ID No.57
HS21:CATCAGTCCAAACAGCAGCAGACCTTCTTGCAATTTGAGTTCTTCCAACAGTTCCAGCAC SEQ ID No.58
HS22:CAGACCTCACAATGGCATCACATCTTCCTTGTGCCCAAGCAGCATCATCAAAGTTTCCAT SEQ ID No.59
HS23:CAACCAGAGATTGATACAGTTGGTCCAGGCCAATTCTGAGCATGTAGGCTCTCAGTCTGG SEQ ID No.60
HS24:GGGAACCAGCCAGTTCTGGGTGTCTTCTTTCAAAATATCTTGTTTGTTGTTCCATGCAAG SEQ ID No.61
HS25:CCAGCCAAGGTCTCCAAAAAAAAAATGTTGGCAACCTCATATTGAGAATCTCCAAACATGG SEQ ID No.62
HS26:CTTCAGACCAGTCAATGACTGCAGTGATTCTGCCATTGTCTGTCAGAACATTGTTGCTTC SEQ ID No.63
HS27:CAAAATCAGCATGGACCAGGTGTCTGACTTCAGGACAATCTTCTGCCCACAGCATGAGTT SEQ ID No.64
HS28:CATCCAGTGCCTGAGCAACAGAAGCAGAAACTGTGTCATCCATCACAGTCTGCCAGTGAT SEQ ID No.65
HS29:AGACATGAGGATCAGCAATGGCACAAATGAAATCCCTCCAAGTGGTGTACTGACCAATGC SEQ ID No.66
HS30:CTTGGGGACCAAAAGGACCAAATCCAGAGGTTTGGCTCAGATCAGCTGCTGCAATGGCAT SEQ ID No.67
HS31:CCATTGCTTCAGCAACAGGTTGCAGAACAGCTGGCAGCTCAGTTTCAGGGAGATCCTGGA SEQ ID No.68
HS32:GAGTGACTCCTTGTGCTCTTCTGCTGATGCAGTAGGTGAGAGATTCAGAAAATTCTCCAA SEQ ID No.69
HS33:TGTCCAGAACTTCTGGAATTGGCAGAGCAGCAGAGGCAAAGTGTCTGTAAACATATCTGT SEQ ID No.70
HS34:CTTTGTAAAAACCATCAGCACAAGAATTGACCCTCAGAACATAACCTCTTCCTCCAACAT SEQ ID No.71
HS35:CAAAAGAAAAGGCTCTGCTTTCTTCACCTTCAGACAGCTGCATGAGATCAGAAACAGAAT SEQ ID No.72
HS36:CAAATTTTTCAATGAGAAACTTCTCAACAGAAGTTGCTGTCAGTTCAGGTTTCTTCATGA SEQ ID No.73
HS37:TGTGCCTCCTCAGCTGAACCGGTGATCTCA SEQ ID No.74

Figure 4

```
       BspHI
1     TCATGAAGACCTTCAACATCTCTCAGCAGGATCTGGAGCTGGTGGAGGTCGCCACTGAG
1       MetLysThrPheAsnIleSerGlnGlnAspLeuGluLeuValGluValAlaThrGlu

 60 AAGATCACCATGCTCTATGAGGACAACAAGCACCATGTCGGGGCGGCCATCAGGACCAAG
 20 LysIleThrMetLeuTyrGluAspAsnLysHisHisValGlyAlaAlaIleArgThrLys

120 ACTGGGGAGATCATCTCTGCTGTCCACATTGAGGCCTACATTGGCAGGGTCACTGTCTGT
 40 ThrGlyGluIleIleSerAlaValHisIleGluAlaTyrIleGlyArgValThrValCys

180 GCTGAAGCCATTGCCATTGGGTCTGCTGTGAGCAACGGGCAGAAGGACTTTGACACCATT
 60 AlaGluAlaIleAlaIleGlySerAlaValSerAsnGlyGlnLysAspPheAspThrIle

240 GTGGCTGTCAGGCACCCCTACTCTGATGAGGTGGACAGATCCATCAGGGTGGTCAGCCCC
 80 ValAlaValArgHisProTyrSerAspGluValAspArgSerIleArgValValSerPro

300 TGTGGCATGTGCAGAGAGCTCATCTCTGACTATGCTCCTGACTGCTTTGTGCTCATTGAG
100 CysGlyMetCysArgGluLeuIleSerAspTyrAlaProAspCysPheValLeuIleGlu

360 ATGAATGGCAAGCTGGTCAAAACCACCATTGAGGAACTCATCCCCCTCAAGTACACCAGG
120 MetAsnGlyLysLeuValLysThrThrIleGluGluLeuIleProLeuLysTyrThrArg
                       NheI
420 AACTAAACCTGAATTCAGCTAGC                         SEQ ID No 5
140 Asn***                                          SEQ ID No 6
```

Figure 5

| Oligo | Sequence | SEQ ID |
|---|---|---|
| OL64: | AGGAGGCACATCATGAAGACCTTCAACATCTCTCAGCAGG | SEQ ID No.75 |
| OL65: | ATCTGGAGCTGGTGGAGGTCGCCACTGAGAAGATCACCAT | SEQ ID No.76 |
| OL66: | GCTCTATGAGGACAACAAGCACCATGTCGGGGCGGCCATC | SEQ ID No.77 |
| OL67: | AGGACCAAGACTGGGGAGATCATCTCTGCTGTCCACATTG | SEQ ID No.78 |
| OL68: | AGGCCTACATTGGCAGGGTCACTGTCTGTGCTGAAGCCAT | SEQ ID No.79 |
| OL69: | TGCCATTGGGTCTGCTGTGAGCAACGGGCAGAAGGACTTT | SEQ ID No.80 |
| OL70: | GACACCATTGTGGCTGTCAGGCACCCCTACTCTGATGAGG | SEQ ID No.81 |
| OL71: | TGGACAGATCCATCAGGGTGGTCAGCCCCTGTGGCATGTG | SEQ ID No.82 |
| OL72: | CAGAGAGCTCATCTCTGACTATGCTCCTGACTGCTTTGTG | SEQ ID No.83 |
| OL73: | CTCATTGAGATGAATGGCAAGCTGGTCAAAACCACCATTG | SEQ ID No.84 |
| OL74: | AGGAACTCATCCCCCTCAAGTACACCAGGAACTAAACCTG | SEQ ID No.85 |
| OL75: | AATTCAGCTAGCTCGACATGA | SEQ ID No.86 |
| OL76: | TCATGTCGAGCTAGCTGAATTCAGGTTTAGTTCCTGGTGTA | SEQ ID No.87 |
| OL77: | CTTGAGGGGGATGAGTTCCTCAATGGTGGTTTTGACCAGC | SEQ ID No.88 |
| OL78: | TTGCCATTCATCTCAATGAGCACAAAGCAGTCAGGAGCAT | SEQ ID No.89 |
| OL79: | AGTCAGAGATGAGCTCTCTGCACATGCCACAGGGGCTGAC | SEQ ID No.90 |
| OL80: | CACCCTGATGGATCTGTCCACCTCATCAGAGTAGGGGTGC | SEQ ID No.91 |
| OL81: | CTGACAGCCACAATGGTGTCAAAGTCCTTCTGCCCGTTGC | SEQ ID No.92 |
| OL82: | TCACAGCAGACCCAATGGCAATGGCTTCAGCACAGACAGT | SEQ ID No.93 |
| OL83: | GACCCTGCCAATGTAGGCCTCAATGTGGACAGCAGAGATG | SEQ ID No.94 |
| OL84: | ATCTCCCCAGTCTTGGTCCTGATGGCCGCCCCGACATGGT | SEQ ID No.95 |
| OL85: | GCTTGTTGTCCTCATAGAGCATGGTGATCTTCTCAGTGGC | SEQ ID No.96 |
| OL86: | GACCTCCACCAGCTCCAGATCCTGCTGAGAGATGTTGAAG | SEQ ID No.97 |
| OL87: | GTCTTCATGATGTGCCTCCT | SEQ ID No.98 |

Figure 6

```
     BspHI
1    TCATGACTGAGTACAAACCCACAGTGAGGCTGGCAACCAGAGATGATGTTCCAAGAGCT
1      MetThrGluTyrLysProThrValArgLeuAlaThrArgAspAspValProArgAla

 60 GTGAGAACACTGGCTGCTGCTTTTGCAGACTACCCTGCAACAAGGCACACAGTTGACCCT
 20 ValArgThrLeuAlaAlaAlaPheAlaAspTyrProAlaThrArgHisThrValAspPro

120 GACAGGCACATTGAGAGGGTGACAGAACTGCAAGAACTCTTCCTCACCAGAGTGGGACTG
 40 AspArgHisIleGluArgValThrGluLeuGlnGluLeuPheLeuThrArgValGlyLeu

180 GACATTGGAAAAGTTTGGGTTGCAGATGATGGAGCTGCTGTTGCAGTTTGGACAACACCT
 60 AspIleGlyLysValTrpValAlaAspAspGlyAlaAlaValAlaValTrpThrThrPro

240 GAGTCTGTTGAAGCTGGTGCTGTTTTTGCTGAAATTGGACCAAGAATGGCTGAGCTCTCT
 80 GluSerValGluAlaGlyAlaValPheAlaGluIleGlyProArgMetAlaGluLeuSer

300 GGAAGCAGGCTGGCAGCACAACAACAAATGGAAGGTCTGCTGGCACCACACAGGCCAAAA
100 GlySerArgLeuAlaAlaGlnGlnGlnMetGluGlyLeuLeuAlaProHisArgProLys

360 GAGCCAGCTTGGTTTCTGGCAACTGTTGGAGTGAGCCCTGACCACCAGGGAAAGGGTCTG
120 GluProAlaTrpPheLeuAlaThrValGlyValSerProAspHisGlnGlyLysGlyLeu

420 GGATCTGCTGTTGTTCTGCCTGGAGTTGAAGCTGCTGAAAGGGCTGGAGTTCCTGCCTTT
140 GlySerAlaValValLeuProGlyValGluAlaAlaGluArgAlaGlyValProAlaPhe

480 CTGGAAACTTCTGCTCCCAGAAACCTGCCTTTTTATGAAAGACTGGGATTCACTGTGACA
160 LeuGluThrSerAlaProArgAsnLeuProPheTyrGluArgLeuGlyPheThrValThr

540 GCTGATGTTGAGGTTCCAGAAGGCCCAAGAACTTGGTGCATGACAAGGAAGCCTGGAGCT
180 AlaAspValGluValProGluGlyProArgThrTrpCysMetThrArgLysProGlyAla
              NheI
600 TAAACCTGAGCTAGC                         SEQ ID No 7
200 ***                                     SEQ ID No 8
```

Figure 7 pur1:CTCACTATAGGAGGACCATCATGACTGAGTACAAACCCACAGTGAGGCTGGCAACCAGAG SEQ ID No.99
pur2:ATGATGTTCCAAGAGCTGTGAGAACACTGGCTGCTGCTTTTGCAGACTACCCTGCAACAA SEQ ID No.100
pur3:GGCACACAGTTGACCCTGACAGGCACATTGAGAGGGTGACAGAACTGCAAGAACTCTTCC SEQ ID No.101
pur4:TCACCAGAGTGGGACTGGACATTGGAAAAGTTTGGGTTGCAGATGATGGAGCTGCTGTTG SEQ ID No.102
pur5:CAGTTTGGACAACACCTGAGTCTGTTGAAGCTGGTGCTGTTTTTGCTGAAATTGGACCAA SEQ ID No.103
pur6:GAATGGCTGAGCTCTCTGGAAGCAGGCTGGCAGCACAACAACAAATGGAAGGTCTGCTGG SEQ ID No.104
pur7:CACCACACAGGCCAAAAGAGCCAGCTTGGTTTCTGGCAACTGTTGGAGTGAGCCCTGACC SEQ ID No.105
pur8:ACCAGGGAAAGGGTCTGGGATCTGCTGTTGTTCTGCCTGGAGTTGAAGCTGCTGAAAGGG SEQ ID No.106
pur9:CTGGAGTTCCTGCCTTTCTGGAAACTTCTGCTCCCAGAAACCTGCCTTTTTATGAAAGAC SEQ ID No.107
pur10:TGGGATTCACTGTGACAGCTGATGTTGAGGTTCCAGAAGGCCCAAGAACTTGGTGCATGA SEQ ID No.108
pur11:CAAGGAAGCCTGGAGCTTAAACCTGAGCTAGCTCGACATGATAAGATACATTGATGAGTT SEQ ID No.109
pur12:AACTCATCAATGTATCTTATCATGTCGAGC SEQ ID No.110
pur13:TAGCTCAGGTTTAAGCTCCAGGCTTCCTTGTCATGCACCAAGTTCTTGGGCCTTCTGGAA SEQ ID No.111
pur14:CCTCAACATCAGCTGTCACAGTGAATCCCAGTCTTTCATAAAAAGGCAGGTTTCTGGGAG SEQ ID No.112
pur15:CAGAAGTTTCCAGAAAGGCAGGAACTCCAGCCCTTTCAGCAGCTTCAACTCCAGGCAGAA SEQ ID No.113
pur16:CAACAGCAGATCCCAGACCCTTTCCCTGGTGGTCAGGGCTCACTCCAACAGTTGCCAGAA SEQ ID No.114
pur17:ACCAAGCTGGCTCTTTTGGCCTGTGTGGTGCCAGCAGACCTTCCATTTGTTGTTGTGCTG SEQ ID No.115
pur18:CCAGCCTGCTTCCAGAGAGCTCAGCCATTCTTGGTCCAATTTCAGCAAAAACAGCACCAG SEQ ID No.116
pur19:CTTCAACAGACTCAGGTGTTGTCCAAACTGCAACAGCAGCTCCATCATCTGCAACCCAAA SEQ ID No.117
pur20:CTTTTCCAATGTCCAGTCCCACTCTGGTGAGGAAGAGTTCTTGCAGTTCTGTCACCCTCT SEQ ID No.118
pur21:CAATGTGCCTGTCAGGGTCAACTGTGTGCCTTGTTGCAGGGTAGTCTGCAAAAGCAGCAG SEQ ID No.119
pur22:CCAGTGTTCTCACAGCTCTTGGAACATCATCTCTGGTTGCCAGCCTCACTGTGGGTTTGT SEQ ID No.120
pur23:ACTCAGTCATGATGGTCCTCCTATAGTGAG SEQ ID No.121

Figure 8a

```
     NcoI
   1 CCATGGACCCTGTTGTGCTGCAAAGGAGAGACTGGGAGAACCCTGGAGTGACCCAGCTC SEQ ID No 5
   1   MetAspProValValLeuGlnArgArgAspTrpGluAsnProGlyValThrGlnLeu SEQ ID No 10

  60 AACAGACTGGCTGCCCACCCTCCCTTTGCCTCTTGGAGGAACTCTGAGGAAGCCAGGACA
  20 AsnArgLeuAlaAlaHisProProPheAlaSerTrpArgAsnSerGluGluAlaArgThr

 120 GACAGGCCCAGCCAGCAGCTCAGGTCTCTCAATGGAGAGTGGAGGTTTGCCTGGTTCCCT
  40 AspArgProSerGlnGlnLeuArgSerLeuAsnGlyGluTrpArgPheAlaTrpPhePro

 180 GCCCCTGAAGCTGTGCCTGAGTCTTGGCTGGAGTGTGACCTCCCAGAGGCTGACACTGTT
  60 AlaProGluAlaValProGluSerTrpLeuGluCysAspLeuProGluAlaAspThrVal

 240 GTGGTGCCCAGCAACTGGCAGATGCATGGCTATGATGCCCCCATCTACACCAATGTCACC
  80 ValValProSerAsnTrpGlnMetHisGlyTyrAspAlaProIleTyrThrAsnValThr

 300 TACCCCATCACTGTGAACCCCCCTTTTGTGCCCACTGAGAACCCCACTGGCTGCTACAGC
 100 TyrProIleThrValAsnProProPheValProThrGluAsnProThrGlyCysTyrSer

 360 CTGACCTTCAATGTTGATGAGAGCTGGCTGCAAGAAGGCCAGACCAGGATCATCTTTGAT
 120 LeuThrPheAsnValAspGluSerTrpLeuGlnGluGlyGlnThrArgIleIlePheAsp

 420 GGAGTCAACTCTGCCTTCCACCTCTGGTGCAATGGCAGGTGGGTTGGCTATGGCCAAGAC
 140 GlyValAsnSerAlaPheHisLeuTrpCysAsnGlyArgTrpValGlyTyrGlyGlnAsp

 480 AGCAGGCTGCCCTCTGAGTTTGACCTCTCTGCCTTCCTCAGAGCTGGAGAGAACAGGCTG
 160 SerArgLeuProSerGluPheAspLeuSerAlaPheLeuArgAlaGlyGluAsnArgLeu

 540 GCTGTCATGGTGCTCAGGTGGTCTGATGGCAGCTACCTGGAAGACCAAGACATGTGGAGG
 180 AlaValMetValLeuArgTrpSerAspGlySerTyrLeuGluAspGlnAspMetTrpArg

 600 ATGTCTGGCATCTTCAGGGATGTGAGCCTGCTGCACAAGCCCACCACCCAGATTTCTGAC
 200 MetSerGlyIlePheArgAspValSerLeuLeuHisLysProThrThrGlnIleSerAsp

 660 TTCCATGTTGCCACCAGGTTCAATGATGACTTCAGCAGAGCTGTGCTGGAGGCTGAGGTG
 220 PheHisValAlaThrArgPheAsnAspAspPheSerArgAlaValLeuGluAlaGluVal

 720 CAGATGTGTGGAGAACTCAGAGACTACCTGAGAGTCACAGTGAGCCTCTGGCAAGGTGAG
 240 GlnMetCysGlyGluLeuArgAspTyrLeuArgValThrValSerLeuTrpGlnGlyGlu

 780 ACCCAGGTGGCCTCTGGCACAGCCCCCTTTGGAGGAGAGATCATTGATGAGAGAGGAGGC
 260 ThrGlnValAlaSerGlyThrAlaProPheGlyGlyGluIleIleAspGluArgGlyGly

 840 TATGCTGACAGAGTCACCCTGAGGCTCAATGTGGAGAACCCCAAGCTGTGGTCTGCTGAG
 280 TyrAlaAspArgValThrLeuArgLeuAsnValGluAsnProLysLeuTrpSerAlaGlu

 900 ATCCCCAACCTCTACAGGGCTGTTGTGGAGCTGCACACTGCTGATGGCACCCTGATTGAA
 300 IleProAsnLeuTyrArgAlaValValGluLeuHisThrAlaAspGlyThrLeuIleGlu

 960 GCTGAAGCCTGTGATGTTGGATTCAGAGAAGTCAGGATTGAGAATGGCCTGCTGCTGCTC
 320 AlaGluAlaCysAspValGlyPheArgGluValArgIleGluAsnGlyLeuLeuLeuLeu

1020 AATGGCAAGCCTCTGCTCATCAGGGGAGTCAACAGGCATGAGCACCACCCTCTGCATGGA
 340 AsnGlyLysProLeuLeuIleArgGlyValAsnArgHisGluHisHisProLeuHisGly

                                               EcoRV
1080 CAAGTGATGGATGAACAGACAATGGTGCAAGATATCCTGCTAATGAAGCAGAACAACTTC
```

Figure 8b

```
 360 GlnValMetAspGluGlnThrMetValGlnAspIleLeuLeuMetLysGlnAsnAsnPhe

1140 AATGCTGTCAGGTGCTCTCACTACCCCAACCACCCTCTCTGGTACACCCTGTGTGACAGG
 380 AsnAlaValArgCysSerHisTyrProAsnHisProLeuTrpTyrThrLeuCysAspArg

1200 TATGGCCTGTATGTTGTTGATGAAGCCAACATTGAGACACATGGCATGGTGCCCATGAAC
 400 TyrGlyLeuTyrValValAspGluAlaAsnIleGluThrHisGlyMetValProMetAsn

1260 AGGCTCACAGATGACCCCAGGTGGCTGCCTGCCATGTCTGAGAGAGTGACCAGGATGGTG
 420 ArgLeuThrAspAspProArgTrpLeuProAlaMetSerGluArgValThrArgMetVal

1320 CAGAGAGACAGGAACCACCCCTCTGTGATCATCTGGTCTCTGGGCAATGAGTCTGGACAT
 440 GlnArgAspArgAsnHisProSerValIleIleTrpSerLeuGlyAsnGluSerGlyHis

1380 GGAGCCAACCATGATGCTCTCTACAGGTGGATCAAGTCTGTTGACCCCAGCAGACCTGTG
 460 GlyAlaAsnHisAspAlaLeuTyrArgTrpIleLysSerValAspProSerArgProVal

1440 CAGTATGAAGGAGGTGGAGCAGACACCACAGCCACAGACATCATCTGCCCCATGTATGCC
 480 GlnTyrGluGlyGlyGlyAlaAspThrThrAlaThrAspIleIleCysProMetTyrAla

1500 AGGGTTGATGAGGACCAGCCCTTCCCTGCTGTGCCCAAGTGGAGCATCAAGAAGTGGCTC
 500 ArgValAspGluAspGlnProPheProAlaValProLysTrpSerIleLysLysTrpLeu

1560 TCTCTGCCTGGAGAGACCAGACCTCTGATCCTGTGTGAATATGCACATGCAATGGGCAAC
 520 SerLeuProGlyGluThrArgProLeuIleLeuCysGluTyrAlaHisAlaMetGlyAsn

1620 TCTCTGGGAGGCTTTGCCAAGTACTGGCAAGCCTTCAGACAGTACCCCAGGCTGCAAGGA
 540 SerLeuGlyGlyPheAlaLysTyrTrpGlnAlaPheArgGlnTyrProArgLeuGlnGly

1680 GGATTTGTGTGGGACTGGGTGGACCAATCTCTCATCAAGTATGATGAGAATGGCAACCCC
 560 GlyPheValTrpAspTrpValAspGlnSerLeuIleLysTyrAspGluAsnGlyAsnPro

1740 TGGTCTGCCTATGGAGGAGACTTTGGTGACACCCCCAATGACAGGCAGTTCTGCATGAAT
 580 TrpSerAlaTyrGlyGlyAspPheGlyAspThrProAsnAspArgGlnPheCysMetAsn

1800 GGCCTGGTCTTTGCAGACAGGACCCCTCACCCTGCCCTCACAGAGGCCAAGCACCAGCAA
 600 GlyLeuValPheAlaAspArgThrProHisProAlaLeuThrGluAlaLysHisGlnGln

1860 CAGTTCTTCCAGTTCAGGCTGTCTGGACAGACCATTGAGGTGACATCTGAGTACCTCTTC
 620 GlnPhePheGlnPheArgLeuSerGlyGlnThrIleGluValThrSerGluTyrLeuPhe

                        SacI
1920 AGGCACTCTGACAATGAGCTCCTGCACTGGATGGTGGCCCTGGATGGCAAGCCTCTGGCT
 640 ArgHisSerAspAsnGluLeuLeuHisTrpMetValAlaLeuAspGlyLysProLeuAla

1980 TCTGGTGAGGTGCCTCTGGATGTGGCCCCTCAAGGAAAGCAGCTGATTGAACTGCCTGAG
 660 SerGlyGluValProLeuAspValAlaProGlnGlyLysGlnLeuIleGluLeuProGlu

2040 CTGCCTCAGCCAGAGTCTGCTGGACAACTGTGGCTAACAGTGAGGGTGGTTCAGCCCAAT
 680 LeuProGlnProGluSerAlaGlyGlnLeuTrpLeuThrValArgValValGlnProAsn

2100 GCAACAGCTTGGTCTGAGGCAGGCCACATCTCTGCATGGCAGCAGTGGAGGCTGGCTGAG
 700 AlaThrAlaTrpSerGluAlaGlyHisIleSerAlaTrpGlnGlnTrpArgLeuAlaGlu

2160 AACCTCTCTGTGACCCTGCCTGCTGCCTCTCATGCCATCCCTCACCTGACAACATCTGAA
 720 AsnLeuSerValThrLeuProAlaAlaSerHisAlaIleProHisLeuThrThrSerGlu

2220 ATGGACTTCTGCATTGAGCTGGGCAACAAGAGATGGCAGTTCAACAGGCAGTCTGGCTTC
 740 MetAspPheCysIleGluLeuGlyAsnLysArgTrpGlnPheAsnArgGlnSerGlyPhe
```

Figure 8c

```
2280 CTGTCTCAGATGTGGATTGGAGACAAGAAGCAGCTCCTCACCCCTCTCAGGGACCAATTC
 760 LeuSerGlnMetTrpIleGlyAspLysLysGlnLeuLeuThrProLeuArgAspGlnPhe

2340 ACCAGGGCTCCTCTGGACAATGACATTGGAGTGTCTGAGGCCACCAGGATTGACCCAAAT
 780 ThrArgAlaProLeuAspAsnAspIleGlyValSerGluAlaThrArgIleAspProAsn

2400 GCTTGGGTGGAGAGGTGGAAGGCTGCTGGACACTACCAGGCTGAGGCTGCCCTGCTCCAG
 800 AlaTrpValGluArgTrpLysAlaAlaGlyHisTyrGlnAlaGluAlaAlaLeuLeuGln

2460 TGCACAGCAGACACCCTGGCTGATGCTGTTCTGATCACCACAGCCCATGCTTGGCAGCAC
 820 CysThrAlaAspThrLeuAlaAspAlaValLeuIleThrThrAlaHisAlaTrpGlnHis

2520 CAAGGCAAGACCCTGTTCATCAGCAGAAAGACCTACAGGATTGATGGCTCTGGACAGATG
 840 GlnGlyLysThrLeuPheIleSerArgLysThrTyrArgIleAspGlySerGlyGlnMet

2580 GCAATCACAGTGGATGTGGAGGTTGCCTCTGACACACCTCACCCTGCAAGGATTGGCCTG
 860 AlaIleThrValAspValGluValAlaSerAspThrProHisProAlaArgIleGlyLeu

2640 AACTGTCAACTGGCACAGGTGGCTGAGAGGGTGAACTGGCTGGGCTTAGGCCCTCAGGAG
 880 AsnCysGlnLeuAlaGlnValAlaGluArgValAsnTrpLeuGlyLeuGlyProGlnGlu

2700 AACTACCCTGACAGGCTGACAGCTGCCTGCTTTGACAGGTGGGACCTGCCTCTGTCTGAC
 900 AsnTyrProAspArgLeuThrAlaAlaCysPheAspArgTrpAspLeuProLeuSerAsp

2760 ATGTACACCCCTTATGTGTTCCCTTCTGAGAATGGCCTGAGGTGTGGCACCAGGGAGCTG
 920 MetTyrThrProTyrValPheProSerGluAsnGlyLeuArgCysGlyThrArgGluLeu

2820 AACTATGGTCCTCACCAGTGGAGGGGAGACTTCCAGTTCAACATCTCCAGGTACTCTCAG
 940 AsnTyrGlyProHisGlnTrpArgGlyAspPheGlnPheAsnIleSerArgTyrSerGln

2880 CAACAGCTCATGGAAACCTCTCACAGGCACCTGCTCCATGCAGAGGAGGGAACCTGGCTG
 960 GlnGlnLeuMetGluThrSerHisArgHisLeuLeuHisAlaGluGluGlyThrTrpLeu

2940 AACATTGATGGCTTCCACATGGGCATTGGAGGAGATGACTCTTGGTCTCCTTCTGTGTCT
 980 AsnIleAspGlyPheHisMetGlyIleGlyGlyAspAspSerTrpSerProSerValSer

3000 GCTGAGTTCCAGTTATCTGCTGGCAGGTACCACTATCAGCTGGTGTGGTGCCAGAAGTAA
1000 AlaGluPheGlnLeuSerAlaGlyArgTyrHisTyrGlnLeuValTrpCysGlnLys***

          NheI
3060 ACCTGAGCTAGC
```

Figure 9 a

BGS001: ATCACTATAGGAGGCCACCATGGACCCTGTTGTGCTGCA SEQ ID No.122
BGS002: GGTGGCCCTCCTATAGTGAT SEQ ID No.123
BGS003: AAGGAGAGACTGGGAGAACCCTGGAGTGACCCAGCTCAAC SEQ ID No.124
BGS004: GGTTCTCCCAGTCTCTCCTTTGCAGCACAACAGGGTCCAT SEQ ID No.125
BGS005: AGACTGGCTGCCCACCCTCCCTTTGCCTCTTGGAGGAACT SEQ ID No.126
BGS006: GGAGGGTGGGCAGCCAGTCTGTTGAGCTGGGTCACTCCAG SEQ ID No.127
BGS007: CTGAGGAAGCCAGGACAGACAGGCCCAGCCAGCAGCTCAG SEQ ID No.128
BGS008: GTCTGTCCTGGCTTCCTCAGAGTTCCTCCAAGAGGCAAAG SEQ ID No.129
BGS009: GTCTCTCAATGGAGAGTGGAGGTTTGCCTGGTTCCCTGCC SEQ ID No.130
BGS010: TCCACTCTCCATTGAGAGACCTGAGCTGCTGGCTGGGCCT SEQ ID No.131
BGS011: CCTGAAGCTGTGCCTGAGTCTTGGCTGGAGTGTGACCTCC SEQ ID No.132
BGS012: GACTCAGGCACAGCTTCAGGGGCAGGGAACCAGGCAAACC SEQ ID No.133
BGS013: CAGAGGCTGACACTGTTGTGGTGCCCAGCAACTGGCAGAT SEQ ID No.134
BGS014: CACAACAGTGTCAGCCTCTGGGAGGTCACACTCCAGCCAA SEQ ID No.135
BGS015: GCATGGCTATGATGCCCCCATCTACACCAATGTCACCTAC SEQ ID No.136
BGS016: TGGGGGCATCATAGCCATGCATCTGCCAGTTGCTGGGCAC SEQ ID No.137
BGS017: CCCATCACTGTGAACCCCCCTTTTGTGCCCACTGAGAACC SEQ ID No.138
BGS018: GGGGGGTTCACAGTGATGGGGTAGGTGACATTGGTGTAGA SEQ ID No.139
BGS019: CCACTGGCTGCTACAGCCTGACCTTCAATGTTGATGAGAG SEQ ID No.140
BGS020: CAGGCTGTAGCAGCCAGTGGGGTTCTCAGTGGGCACAAAA SEQ ID No.141
BGS021: CTGGCTGCAAGAAGGCCAGACCAGGATCATCTTTGATGGA SEQ ID No.142
BGS022: TCTGGCCTTCTTGCAGCCAGCTCTCATCAACATTGAAGGT SEQ ID No.143
BGS023: GTCAACTCTGCCTTCCACCTCTGGTGCAATGGCAGGTGGG SEQ ID No.144
BGS024: AGGTGGAAGGCAGAGTTGACTCCATCAAAGATGATCCTGG SEQ ID No.145
BGS025: TTGGCTATGGCCAAGACAGCAGGCTGCCCTCTGAGTTTGA SEQ ID No.146
BGS026: GCTGTCTTGGCCATAGCCAACCCACCTGCCATTGCACCAG SEQ ID No.147
BGS027: CCTCTCTGCCTTCCTCAGAGCTGGAGAGAACAGGCTGGCT SEQ ID No.148
BGS028: CTCTGAGGAAGGCAGAGAGGTCAAACTCAGAGGGCAGCCT SEQ ID No.149
BGS029: GTCATGGTGCTCAGGTGGTCTGATGGCAGCTACCTGGAAG SEQ ID No.150
BGS030: GACCACCTGAGCACCATGACAGCCAGCCTGTTCTCTCCAG SEQ ID No.151
BGS031: ACCAAGACATGTGGAGGATGTCTGGCATCTTCAGGGATGT SEQ ID No.152
BGS032: CATCCTCCACATGTCTTGGTCTTCCAGGTAGCTGCCATCA SEQ ID No.153
BGS033: GAGCCTGCTGCACAAGCCCACCACCCAGATTTCTGACTTC SEQ ID No.154
BGS034: TGGGCTTGTGCAGCAGGCTCACATCCCTGAAGATGCCAGA SEQ ID No.155
BGS035: CATGTTGCCACCAGGTTCAATGATGACTTCAGCAGAGCTG SEQ ID No.156
BGS036: TTGAACCTGGTGGCAACATGGAAGTCAGAAATCTGGGTGG SEQ ID No.157
BGS037: TGCTGGAGGCTGAGGTGCAGATGTGTGGAGAACTCAGAGA SEQ ID No.158
BGS038: CTGCACCTCAGCCTCCAGCACAGCTCTGCTGAAGTCATCA SEQ ID No.159
BGS039: CTACCTGAGAGTCACAGTGAGCCTCTGGCAAGGTGAGACC SEQ ID No.160
BGS040: TCACTGTGACTCTCAGGTAGTCTCTGAGTTCTCCACACAT SEQ ID No.161
BGS041: CAGGTGGCCTCTGGCACAGCCCCCTTTGGAGGAGAGATCA SEQ ID No.162
BGS042: GCTGTGCCAGAGGCCACCTGGGTCTCACCTTGCCAGAGGC SEQ ID No.163
BGS043: TTGATGAGAGAGGAGGCTATGCTGACAGAGTCACCCTGAG SEQ ID No.164
BGS044: ATAGCCTCCTCTCTCATCAATGATCTCTCCTCCAAAGGGG SEQ ID No.165
BGS045: GCTCAATGTGGAGAACCCCAAGCTGTGGTCTGCTGAGATC SEQ ID No.166
BGS046: TGGGGTTCTCCACATTGAGCCTCAGGGTGACTCTGTCAGC SEQ ID No.167
BGS047: CCCAACCTCTACAGGGCTGTTGTGGAGCTGCACACTGCTG SEQ ID No.168
BGS048: ACAGCCCTGTAGAGGTTGGGGATCTCAGCAGACCACAGCT SEQ ID No.169
BGS049: ATGGCACCCTGATTGAAGCTGAAGCCTGTGATGTTGGATT SEQ ID No.170
BGS050: AGCTTCAATCAGGGTGCCATCAGCAGTGTGCAGCTCCACA SEQ ID No.171
BGS051: CAGAGAAGTCAGGATTGAGAATGGCCTGCTGCTGCTCAAT SEQ ID No.172
BGS052: TCTCAATCCTGACTTCTCTGAATCCAACATCACAGGCTTC SEQ ID No.173
BGS053: GGCAAGCCTCTGCTCATCAGGGGAGTCAACAGGCATGAGC SEQ ID No.174
BGS054: CTGATGAGCAGAGGCTTGCCATTGAGCAGCAGCAGGCCAT SEQ ID No.175
BGS055: ACCACCCTCTGCATGGACAAGTGATGGATGAACAGACAAT SEQ ID No.176

Figure 9b

BGS056: TTGTCCATGCAGAGGGTGGTGCTCATGCCTGTTGACTCCC SEQ ID No.177
BGS057: GGTGCAAGATATCCTGCTGATGAAGCAGAACTCCGCCTAC SEQ ID No.178
BGS058: TCAGCAGGATATCTTGCACCATTGTCTGTTCATCCATCAC SEQ ID No.179
BGS059: GTAGGCGGAGTTCTGCTTCA SEQ ID No.180

Figure 10a

BGS060: TCATTAGCAGGATATCTTGC SEQ ID No.181
BGS061: GCAAGATATCCTGCTAATGAAGCAGAACAACTTCAATGCT SEQ ID No.182
BGS062: GGGTAGTGAGAGCACCTGACAGCATTGAAGTTGTTCTGCT SEQ ID No.183
BGS063: GTCAGGTGCTCTCACTACCCCAACCACCCTCTCTGGTACA SEQ ID No.184
BGS064: GCCATACCTGTCACACAGGGTGTACCAGAGAGGGTGGTTG SEQ ID No.185
BGS065: CCCTGTGTGACAGGTATGGCCTGTATGTTGTTGATGAAGC SEQ ID No.186
BGS066: TGCCATGTGTCTCAATGTTGGCTTCATCAACAACATACAG SEQ ID No.187
BGS067: CAACATTGAGACACATGGCATGGTGCCCATGAACAGGCTC SEQ ID No.188
BGS068: AGCCACCTGGGGTCATCTGTGAGCCTGTTCATGGGCACCA SEQ ID No.189
BGS069: ACAGATGACCCCAGGTGGCTGCCTGCCATGTCTGAGAGAG SEQ ID No.190
BGS070: TCTCTGCACCATCCTGGTCACTCTCTCAGACATGGCAGGC SEQ ID No.191
BGS071: TGACCAGGATGGTGCAGAGAGACAGGAACCACCCCTCTGT SEQ ID No.192
BGS072: TGCCCAGAGACCAGATGATCACAGAGGGGTGGTTCCTGTC SEQ ID No.193
BGS073: GATCATCTGGTCTCTGGGCAATGAGTCTGGACATGGAGCC SEQ ID No.194
BGS074: CTGTAGAGAGCATCATGGTTGGCTCCATGTCCAGACTCAT SEQ ID No.195
BGS075: AACCATGATGCTCTCTACAGGTGGATCAAGTCTGTTGACC SEQ ID No.196
BGS076: ATACTGCACAGGTCTGCTGGGGTCAACAGACTTGATCCAC SEQ ID No.197
BGS077: CCAGCAGACCTGTGCAGTATGAAGGAGGTGGAGCAGACAC SEQ ID No.198
BGS078: AGATGATGTCTGTGGCTGTGGTGTCTGCTCCACCTCCTTC SEQ ID No.199
BGS079: CACAGCCACAGACATCATCTGCCCCATGTATGCCAGGGTT SEQ ID No.200
BGS080: GGGAAGGGCTGGTCCTCATCAACCCTGGCATACATGGGGC SEQ ID No.201
BGS081: GATGAGGACCAGCCCTTCCCTGCTGTGCCCAAGTGGAGCA SEQ ID No.202
BGS082: CAGAGAGAGCCACTTCTTGATGCTCCACTTGGGCACAGCA SEQ ID No.203
BGS083: TCAAGAAGTGGCTCTCTCTGCCTGGAGAGACCAGACCTCT SEQ ID No.204
BGS084: GTGCATATTCACACAGGATCAGAGGTCTGGTCTCTCCAGG SEQ ID No.205
BGS085: GATCCTGTGTGAATATGCACATGCAATGGGCAACTCTCTG SEQ ID No.206
BGS086: CAGTACTTGGCAAAGCCTCCCAGAGAGTTGCCCATTGCAT SEQ ID No.207
BGS087: GGAGGCTTTGCCAAGTACTGGCAAGCCTTCAGACAGTACC SEQ ID No.208
BGS088: AAATCCTCCTTGCAGCCTGGGGTACTGTCTGAAGGCTTGC SEQ ID No.209
BGS089: CCAGGCTGCAAGGAGGATTTGTGTGGGACTGGGTGGACCA SEQ ID No.210
BGS090: CATCATACTTGATGAGAGATTGGTCCACCCAGTCCCACAC SEQ ID No.211
BGS091: ATCTCTCATCAAGTATGATGAGAATGGCAACCCCTGGTCT SEQ ID No.212
BGS092: CCAAAGTCTCCTCCATAGGCAGACCAGGGGTTGCCATTCT SEQ ID No.213
BGS093: GCCTATGGAGGAGACTTTGGTGACACCCCCAATGACAGGC SEQ ID No.214
BGS094: CAGGCCATTCATGCAGAACTGCCTGTCATTGGGGGTGTCA SEQ ID No.215
BGS095: AGTTCTGCATGAATGGCCTGGTCTTTGCAGACAGGACCCC SEQ ID No.216
BGS096: CCTCTGTGAGGGCAGGGTGAGGGGTCCTGTCTGCAAAGAC SEQ ID No.217
BGS097: TCACCCTGCCCTCACAGAGGCCAAGCACCAGCAACAGTTC SEQ ID No.218
BGS098: CCAGACAGCCTGAACTGGAAGAACTGTTGCTGGTGCTTGG SEQ ID No.219
BGS099: TTCCAGTTCAGGCTGTCTGGACAGACCATTGAGGTGACAT SEQ ID No.220
BGS100: GTGCCTGAAGAGGTACTCAGATGTCACCTCAATGGTCTGT SEQ ID No.221
BGS101: CTGAGTACCTCTTCAGGCACTCTGACAATGAGCTCCTGCA SEQ ID No.222
BGS102: TGCAGGAGCTCATTGTCAGA SEQ ID No.223

Figure 10b -1

BGS103: GTAATTTAACAATGAGCTCCTGCACTGGATGGTGGCCCTG SEQ ID No.224
BGS104: GGAGCTCATTGTTAAATTAC SEQ ID No.225
BGS105: GATGGCAAGCCTCTGGCTTCTGGTGAGGTGCCTCTGGATG SEQ ID No.226
BGS106: GAAGCCAGAGGCTTGCCATCCAGGGCCACCATCCAGTGCA SEQ ID No.227
BGS107: TGGCCCCTCAAGGAAAGCAGCTGATTGAACTGCCTGAGCT SEQ ID No.228
BGS108: CTGCTTTCCTTGAGGGGCCACATCCAGAGGCACCTCACCA SEQ ID No.229
BGS109: GGCTCAGCCAGAGTCTGCTGGACAACTGTGGCTAACAGTG SEQ ID No.230
BGS110: CAGCAGACTCTGGCTGAGGCAGCTCAGGCAGTTCAATCAG SEQ ID No.231
BGS111: AGGGTGGTTCAGCCCAATGCAACAGCTTGGTCTGAGGCAG SEQ ID No.232
BGS112: GCATTGGGCTGAACCACCCTCACTGTTAGCCACAGTTGTC SEQ ID No.233
BGS113: GCCACATCTCTGCATGGCAGCAGTGGAGGCTGGCTGAGAA SEQ ID No.234
BGS114: CTGCCATGCAGAGATGTGGCCTGCCTCAGACCAAGCTGTT SEQ ID No.235
BGS115: CCTCTCTGTGACCCTGCCTGCTGCCTCTCATGCCATCCCT SEQ ID No.236
BGS116: CAGGCAGGGTCACAGAGAGGTTCTCAGCCAGCCTCCACTG SEQ ID No.237
BGS117: CACCTGACAACATCTGAAATGGACTTCTGCATTGAGCTGG SEQ ID No.238
BGS118: ATTTCAGATGTTGTCAGGTGAGGGATGGCATGAGAGGCAG SEQ ID No.239
BGS119: GCAACAAGAGATGGCAGTTCAACAGGCAGTCTGGCTTCCT SEQ ID No.240
BGS120: GAACTGCCATCTCTTGTTGCCCAGCTCAATGCAGAAGTCC SEQ ID No.241
BGS121: GTCTCAGATGTGGATTGGAGACAAGAAGCAGCTCCTCACC SEQ ID No.242
BGS122: CTCCAATCCACATCTGAGACAGGAAGCCAGACTGCCTGTT SEQ ID No.243
BGS123: CCTCTCAGGGACCAATTCACCAGGGCTCCTCTGGACAATG SEQ ID No.244
BGS124: GTGAATTGGTCCCTGAGAGGGGTGAGGAGCTGCTTCTTGT SEQ ID No.245
BGS125: ACATTGGAGTGTCTGAGGCCACCAGGATTGACCCAAATGC SEQ ID No.246
BGS126: GGCCTCAGACACTCCAATGTCATTGTCCAGAGGAGCCCTG SEQ ID No.247
BGS127: TTGGGTGGAGAGGTGGAAGGCTGCTGGACACTACCAGGCT SEQ ID No.248
BGS128: CCTTCCACCTCTCCACCCAAGCATTTGGGTCAATCCTGGT SEQ ID No.249
BGS129: GAGGCTGCCCTGCTCCAGTGCACAGCAGACACCCTGGCTG SEQ ID No.250
BGS130: CACTGGAGCAGGGCAGCCTCAGCCTGGTAGTGTCCAGCAG SEQ ID No.251
BGS131: ATGCTGTTCTGATCACCACAGCCCATGCTTGGCAGCACCA SEQ ID No.252
BGS132: TGTGGTGATCAGAACAGCATCAGCCAGGGTGTCTGCTGTG SEQ ID No.253
BGS133: AGGCAAGACCCTGTTCATCAGCAGAAAGACCTACAGGATT SEQ ID No.254
BGS134: TGATGAACAGGGTCTTGCCTTGGTGCTGCCAAGCATGGGC SEQ ID No.255
BGS135: GATGGCTCTGGACAGATGGCAATCACAGTGGATGTGGAGG SEQ ID No.256
BGS136: GCCATCTGTCCAGAGCCATCAATCCTGTAGGTCTTTCTGC SEQ ID No.257
BGS137: TTGCCTCTGACACACCTCACCCTGCAAGGATTGGCCTGAA SEQ ID No.258
BGS138: GTGAGGTGTGTCAGAGGCAACCTCCACATCCACTGTGATT SEQ ID No.259
BGS139: CTGTCAACTGGCACAGGTGGCTGAGAGGGTGAACTGGCTG SEQ ID No.260
BGS140: CCACCTGTGCCAGTTGACAGTTCAGGCCAATCCTTGCAGG SEQ ID No.261
BGS141: GGCTTAGGCCCTCAGGAGAACTACCCTGACAGGCTGACAG SEQ ID No.262
BGS142: TTCTCCTGAGGGCCTAAGCCCAGCCAGTTCACCCTCTCAG SEQ ID No.263
BGS143: CTGCCTGCTTTGACAGGTGGGACCTGCCTCTGTCTGACAT SEQ ID No.264
BGS144: CCACCTGTCAAAGCAGGCAGCTGTCAGCCTGTCAGGGTAG SEQ ID No.265
BGS145: GTACACCCCTTATGTGTTCCCTTCTGAGAATGGCCTGAGG SEQ ID No.266
BGS146: GGAACACATAAGGGGTGTACATGTCAGACAGAGGCAGGTC SEQ ID No.267
BGS147: TGTGGCACCAGGGAGCTGAACTATGGTCCTCACCAGTGGA SEQ ID No.268
BGS148: TTCAGCTCCCTGGTGCCACACCTCAGGCCATTCTCAGAAG SEQ ID No.269
BGS149: GGGGAGACTTCCAGTTCAACATCTCCAGGTACTCTCAGCA SEQ ID No.270
BGS150: GTTGAACTGGAAGTCTCCCCTCCACTGGTGAGGACCATAG SEQ ID No.271
BGS151: ACAGCTCATGGAAACCTCTCACAGGCACCTGCTCCATGCA SEQ ID No.272
BGS152: GAGAGGTTTCCATGAGCTGTTGCTGAGAGTACCTGGAGAT SEQ ID No.273
BGS153: GAGGAGGGAACCTGGCTGAACATTGATGGCTTCCACATGG SEQ ID No.274
BGS154: TTCAGCCAGGTTCCCTCCTCTGCATGGAGCAGGTGCCTGT SEQ ID No.275
BGS155: GCATTGGAGGAGATGACTCTTGGTCTCCTTCTGTGTCTGC SEQ ID No.276
BGS156: AGAGTCATCTCCTCCAATGCCCATGTGGAAGCCATCAATG SEQ ID No.277

Figure 10b-2

BGS157: TGAGTTCCAGTTATCTGCTGGCAGGTACCACTATCAGCTG SEQ ID No.278
BGS158: CAGCAGATAACTGGAACTCAGCAGACACAGAAGGAGACCA SEQ ID No.279
BGS159: GTGTGGTGCCAGAAGTAAACCTGAGCTAGCAGTCCATGAT SEQ ID No.280
BGS160: GTTTACTTCTGGCACCACACCAGCTGATAGTGGTACCTGC SEQ ID No.281
BGS161: ATCATGGACTGCTAGCTCAG SEQ ID No.282

Figure 10c

```
    AseI                                                                   NcoI
1-CAATTAATCATcgGCATAGTATATCgGCATAGTATAATACgACTCACTATAGGAGGGCCACCCATGG SEQ ID No.297
2-CAATTAAWCATDGGCATAGTATATCWGCATAGTATAATACHACTCACTATAGGAGGGCCACCCATGG SEQ ID No.298
3-CAATTAAaCATtGGCATAGTATATCtGCATAGTATAATACaACTCACTATAGGAGGGCCACCCATGG SEQ ID No 11
```

Figure 11

```
                 PacI
  1  GCAGGACTGAGGCTTAATTAAACCTTAAAACCTTTAAAAGCCTTATATATTCTTTTTTT

 60  TCTTATAAAACTTAAAACCTTAGAGGCTATTTAAGTTGCTGATTTATATTAATTTTATTG

120  TTCAAACATGAGAGCTTAGTACATGAAACATGAGAGCTTAGTACATTAGCCATGAGAGCT

180  TAGTACATTAGCCATGAGGGTTTAGTTCATTAAACATGAGAGCTTAGTACATTAAACATG

240  AGAGCTTAGTACATGAAACATGAGAGCTTAGTACATACTATCAACAGGTTGAACTGCTGA
         PacI
300  TCTTAATTAACCTGGAGACTT                  SEQ ID No 12
```

Figure 12

RK1 : GCAGGACTGAGGCTTAATTAAACCTTAAAACCTTTAAAAG SEQ ID No.283
RK2 : CCTTATATATTCTTTTTTTTTCTTATAAAACTTAAAACCTT SEQ ID No.284
RK3 : AGAGGCTATTTAAGTTGCTGATTTATATTAATTTTATTGT SEQ ID No.285
RK4 : TCAAACATGAGAGCTTAGTACATGAAACATGAGAGCTTAGTACATTAGCC SEQ ID No.286
RK5 : ATGAGAGCTTAGTACATTAGCCATGAGGGTTTAGTTCATTAAACATGAGAGCTTAGTACA SEQ ID No.287
RK6 : TTAAACATGAGAGCTTAGTACATGAAACATGAGAGCTTAGTACATACTATCAACAGGTTG SEQ ID No.288
RK7 : AACTGCTGATCTTAATTAACCTGGAGACTT SEQ ID No.289
RK8 : AAGTCTCCAGGTTAATTAAGATCAGCAGTTCAACCTGTTGATAGTATGTACTAAGCTCTC SEQ ID No.290
RK9 : ATGTTTCATGTACTAAGCTCTCATGTTTAATGTACTAAGCTCTCATGTTTAATGAACTAA SEQ ID No.291
RK10 : ACCCTCATGGCTAATGTACTAAGCTCTCATGGCTAATGTACTAAGCTCTCATGTTTCATG SEQ ID No.292
RK11 : TACTAAGCTCTCATGTTTGAACAATAAAATTAATATAAAT SEQ ID No.293
RK12 : CAGCAACTTAAATAGCCTCTAAGGTTTTAAGTTTTATAAG SEQ ID No.294
RK13 : AAAAAAAAGAATATATAAGGCTTTTAAAGGTTTTAAGGTT SEQ ID No.295
RK14 : TAATTAAGCCTCAGTCCTGC SEQ ID No.296

Figure 13

```
      PacI
1   TTAATTAACCTTAAAACCTTTAAAAGCCTTATATATTCTTTTTTTCTTATAAAACTTA

60  AAACCTTAGAGGCTATTTAAGTTGCTGATTTATATTAATTTTATTGTTCAAACATGAGAG

120 CTTAGTACATGAAACATGAGAGCTTAGTACATTAGCCATGAGAGCTTAGTACATTAGCCA

180 TGAGGGTTTAGTTCATTAAACATGAGAGCTTAGTACATTAAACATGAGAGCTTAGTACAT
                                      PacI
240 ACTATCAACAGGTTGAACTGCTGATCTTAATTAA               SEQ ID No 13
```

Figure 14 a

```
     PacI
   1 TTAATTAAAACAGTAGTTGACAATTAAACATTGGCATAGTATATCTGCATAGTATAATAC
                                 NcoI
  61 AACTCACTATAGGAGGGCCACCATGGCCAAGTTGACCAGTGCTGTCCCAGTGCTCACAGC
                           MetAlaLysLeuThrSerAlaValProValLeuThrAl
 121 CAGGGATGTGGCTGGAGCTGTTGAGTTCTGGACTGACAGGTTGGGGTTCTCCAGAGATTT
     aArgAspValAlaGlyAlaValGluPheTrpThrAspArgLeuGlyPheSerArgAspPh
 181 TGTGGAGGATGACTTTGCAGGTGTGGTCAGAGATGATGTCACCCTGTTCATCTCAGCAGT
     eValGluAspAspPheAlaGlyValValArgAspAspValThrLeuPheIleSerAlaVa
 241 CCAGGACCAGGTGGTGCCTGACAACACCCTGGCTTGGGTGTGGGTGAGAGGACTGGATGA
     lGlnAspGlnValValProAspAsnThrLeuAlaTrpValTrpValArgGlyLeuAspGl
 301 GCTGTATGCTGAGTGGAGTGAGGTGGTCTCCACCAACTTCAGGGATGCCAGTGGCCCTGC
     uLeuTyrAlaGluTrpSerGluValValSerThrAsnPheArgAspAlaSerGlyProAl
 361 CATGACAGAGATTGGAGAGCAGCCCTGGGGGAGAGAGTTTGCCCTGAGAGACCCAGCAGG
     aMetThrGluIleGlyGluGlnProTrpGlyArgGluPheAlaLeuArgAspProAlaGl
                                                   EcoRI
 421 CAACTGTGTGCACTTTGTGGCAGAGGAGCAGGACTGAGGATAAGAATTCTGAGGAGAAGC
     yAsnCysValHisPheValAlaGluGluGlnAsp•••
 481 TCATGGACCCTGTTGTGCTGCAAAGGAGAGACTGGGAGAACCCTGGAGTGACCCAGCTCA
       MetAspProValValLeuGlnArgArgAspTrpGluAsnProGlyValThrGlnLeuA
 541 ACAGACTGGCTGCCCACCCTCCCTTTGCCTCTTGGAGGAACTCTGAGGAAGCCAGGACAG
     snArgLeuAlaAlaHisProProPheAlaSerTrpArgAsnSerGluGluAlaArgThrA
 601 ACAGGCCCAGCCAGCAGCTCAGGTCTCTCAATGGAGAGTGGAGGTTTGCCTGGTTCCCTG
     spArgProSerGlnGlnLeuArgSerLeuAsnGlyGluTrpArgPheAlaTrpPheProA
 661 CCCCTGAAGCTGTGCCTGAGTCTTGGCTGGAGTGTGACCTCCCAGAGGCTGACACTGTTG
     laProGluAlaValProGluSerTrpLeuGluCysAspLeuProGluAlaAspThrValV
 721 TGGTGCCCAGCAACTGGCAGATGCATGGCTATGATGCCCCCATCTACACCAATGTCACCT
     alValProSerAsnTrpGlnMetHisGlyTyrAspAlaProIleTyrThrAsnValThrT
 781 ACCCCATCACTGTGAACCCCCCTTTTGTGCCCACTGAGAACCCCACTGGCTGCTACAGCC
     yrProIleThrValAsnProProPheValProThrGluAsnProThrGlyCysTyrSerL
 841 TGACCTTCAATGTTGATGAGAGCTGGCTGCAAGAAGGCCAGACCAGGATCATCTTTGATG
     euThrPheAsnValAspGluSerTrpLeuGlnGluGlyGlnThrArgIleIlePheAspG
 901 GAGTCAACTCTGCCTTCCACCTCTGGTGCAATGGCAGGTGGGTTGGCTATGGCCAAGACA
     lyValAsnSerAlaPheHisLeuTrpCysAsnGlyArgTrpValGlyTyrGlyGlnAspS
 961 GCAGGCTGCCCTCTGAGTTTGACCTCTCTGCCTTCCTCAGAGCTGGAGAGAACAGGCTGG
     erArgLeuProSerGluPheAspLeuSerAlaPheLeuArgAlaGlyGluAsnArgLeuA
1021 CTGTCATGGTGCTCAGGTGGTCTGATGGCAGCTACCTGGAAGACCAAGACATGTGGAGGA
     laValMetValLeuArgTrpSerAspGlySerTyrLeuGluAspGlnAspMetTrpArgM
1081 TGTCTGGCATCTTCAGGGATGTGAGCCTGCTGCACAAGCCCACCACCCAGATTTCTGACT
     etSerGlyIlePheArgAspValSerLeuLeuHisLysProThrThrGlnIleSerAspP
1141 TCCATGTTGCCACCAGGTTCAATGATGACTTCAGCAGAGCTGTGCTGGAGGCTGAGGTGC
     heHisValAlaThrArgPheAsnAspAspPheSerArgAlaValLeuGluAlaGluValG
1201 AGATGTGTGGAGAACTCAGAGACTACCTGAGAGTCACAGTGAGCCTCTGGCAAGGTGAGA
     lnMetCysGlyGluLeuArgAspTyrLeuArgValThrValSerLeuTrpGlnGlyGluT
1261 CCCAGGTGGCCTCTGGCACAGCCCCCTTTGGAGGAGAGATCATTGATGAGAGAGGAGGCT
     hrGlnValAlaSerGlyThrAlaProPheGlyGlyGluIleIleAspGluArgGlyGlyT
1321 ATGCTGACAGAGTCACCCTGAGGCTCAATGTGGAGAACCCCAAGCTGTGGTCTGCTGAGA
     yrAlaAspArgValThrLeuArgLeuAsnValGluAsnProLysLeuTrpSerAlaGluI
1381 TCCCCAACCTCTACAGGGCTGTTGTGGAGCTGCACACTGCTGATGGCACCCTGATTGAAG
     leProAsnLeuTyrArgAlaValValGluLeuHisThrAlaAspGlyThrLeuIleGluA
1441 CTGAAGCCTGTGATGTTGGATTCAGAGAAGTCAGGATTGAGAATGGCCTGCTGCTGCTCA
     laGluAlaCysAspValGlyPheArgGluValArgIleGluAsnGlyLeuLeuLeuLeuA
1501 ATGGCAAGCCTCTGCTCATCAGGGGAGTCAACAGGCATGAGCACCACCCTCTGCATGGAC
     snGlyLysProLeuLeuIleArgGlyValAsnArgHisGluHisHisProLeuHisGlyG
1561 AAGTGATGGATGAACAGACAATGGTGCAAGATATCCTGCTAATGAAGCAGAACAACTTCA
     lnValMetAspGluGlnThrMetValGlnAspIleLeuLeuMetLysGlnAsnAsnPheA
1621 ATGCTGTCAGGTGCTCTCACTACCCCAACCACCCTCTCTGGTACACCCTGTGTGACAGGT
     snAlaValArgCysSerHisTyrProAsnHisProLeuTrpTyrThrLeuCysAspArgT
1681 ATGGCCTGTATGTTGTTGATGAAGCCAACATTGAGACACATGGCATGGTGCCCATGAACA
```

Figure 14b

```
     yrGlyLeuTyrValValAspGluAlaAsnIleGluThrHisGlyMetValProMetAsnA
1741 GGCTCACAGATGACCCCAGGTGGCTGCCTGCCATGTCTGAGAGAGTGACCAGGATGGTGC
     rgLeuThrAspAspProArgTrpLeuProAlaMetSerGluArgValThrArgMetValG
1801 AGAGAGACAGGAACCACCCCTCTGTGATCATCTGGTCTCTGGGCAATGAGTCTGGACATG
     lnArgAspArgAsnHisProSerValIleIleTrpSerLeuGlyAsnGluSerGlyHisG
1861 GAGCCAACCATGATGCTCTCTACAGGTGGATCAAGTCTGTTGACCCCAGCAGACCTGTGC
     lyAlaAsnHisAspAlaLeuTyrArgTrpIleLysSerValAspProSerArgProValG
1921 AGTATGAAGGAGGTGGAGCAGACACCACAGCCACAGACATCATCTGCCCCATGTATGCCA
     lnTyrGluGlyGlyGlyAlaAspThrThrAlaThrAspIleIleCysProMetTyrAlaA
1981 GGGTTGATGAGGACCAGCCCTTCCCTGCTGTGCCCAAGTGGAGCATCAAGAAGTGGCTCT
     rgValAspGluAspGlnProPheProAlaValProLysTrpSerIleLysLysTrpLeuS
2041 CTCTGCCTGGAGAGACCAGACCTCTGATCCTGTGTGAATATGCACATGCAATGGGCAACT
     erLeuProGlyGluThrArgProLeuIleLeuCysGluTyrAlaHisAlaMetGlyAsnS
2101 CTCTGGGAGGCTTTGCCAAGTACTGGCAAGCCTTCAGACAGTACCCCAGGCTGCAAGGAG
     erLeuGlyGlyPheAlaLysTyrTrpGlnAlaPheArgGlnTyrProArgLeuGlnGlyG
2161 GATTTGTGTGGGACTGGGTGGACCAATCTCTCATCAAGTATGATGAGAATGGCAACCCCT
     lyPheValTrpAspTrpValAspGlnSerLeuIleLysTyrAspGluAsnGlyAsnProT
2221 GGTCTGCCTATGGAGGAGACTTTGGTGACACCCCCAATGACAGGCAGTTCTGCATGAATG
     rpSerAlaTyrGlyGlyAspPheGlyAspThrProAsnAspArgGlnPheCysMetAsnG
2281 GCCTGGTCTTTGCAGACAGGACCCCTCACCCTGCCCTCACAGAGGCCAAGCACCAGCAAC
     lyLeuValPheAlaAspArgThrProHisProAlaLeuThrGluAlaLysHisGlnGlnG
2341 AGTTCTTCCAGTTCAGGCTGTCTGGACAGACCATTGAGGTGACATCTGAGTACCTCTTCA
     lnPhePheGlnPheArgLeuSerGlyGlnThrIleGluValThrSerGluTyrLeuPheA
2401 GGCACTCTGACAATGAGCTCCTGCACTGGATGGTGGCCCTGGATGGCAAGCCTCTGGCTT
     rgHisSerAspAsnGluLeuLeuHisTrpMetValAlaLeuAspGlyLysProLeuAlaS
2461 CTGGTGAGGTGCCTCTGGATGTGGCCCCTCAAGGAAAGCAGCTGATTGAACTGCCTGAGC
     erGlyGluValProLeuAspValAlaProGlnGlyLysGlnLeuIleGluLeuProGluL
2521 TGCCTCAGCCAGAGTCTGCTGGACAACTGTGGCTAACAGTGAGGGTGGTTCAGCCCAATG
     euProGlnProGluSerAlaGlyGlnLeuTrpLeuThrValArgValValGlnProAsnA
2581 CAACAGCTTGGTCTGAGGCAGGCCACATCTCTGCATGGCAGCAGTGGAGGCTGGCTGAGA
     laThrAlaTrpSerGluAlaGlyHisIleSerAlaTrpGlnGlnTrpArgLeuAlaGluA
2641 ACCTCTCTGTGACCCTGCCTGCTGCCTCTCATGCCATCCCTCACCTGACAACATCTGAAA
     snLeuSerValThrLeuProAlaAlaSerHisAlaIleProHisLeuThrThrSerGluM
2701 TGGACTTCTGCATTGAGCTGGGCAACAAGAGATGGCAGTTCAACAGGCAGTCTGGCTTCC
     etAspPheCysIleGluLeuGlyAsnLysArgTrpGlnPheAsnArgGlnSerGlyPheL
2761 TGTCTCAGATGTGGATTGGAGACAAGAAGCAGCTCCTCACCCCTCTCAGGGACCAATTCA
     euSerGlnMetTrpIleGlyAspLysLysGlnLeuLeuThrProLeuArgAspGlnPheT
2821 CCAGGGCTCCTCTGGACAATGACATTGGAGTGTCTGAGGCCACCAGGATTGACCCAAATG
     hrArgAlaProLeuAspAsnAspIleGlyValSerGluAlaThrArgIleAspProAsnA
2881 CTTGGGTGGAGAGGTGGAAGGCTGCTGGACACTACCAGGCTGAGGCTGCCCTGCTCCAGT
     laTrpValGluArgTrpLysAlaAlaGlyHisTyrGlnAlaGluAlaAlaLeuLeuGlnC
2941 GCACAGCAGACACCCTGGCTGATGCTGTTCTGATCACCACAGCCCATGCTTGGCAGCACC
     ysThrAlaAspThrLeuAlaAspAlaValLeuIleThrThrAlaHisAlaTrpGlnHisG
3001 AAGGCAAGACCCTGTTCATCAGCAGAAAGACCTACAGGATTGATGGCTCTGGACAGATGG
     lnGlyLysThrLeuPheIleSerArgLysThrTyrArgIleAspGlySerGlyGlnMetA
3061 CAATCACAGTGGATGTGGAGGTTGCCTCTGACACACCTCACCCTGCAAGGATTGGCCTGA
     laIleThrValAspValGluValAlaSerAspThrProHisProAlaArgIleGlyLeuA
3121 ACTGTCAACTGGCACAGGTGGCTGAGAGGGTGAACTGGCTGGGCTTAGGCCCTCAGGAGA
     snCysGlnLeuAlaGlnValAlaGluArgValAsnTrpLeuGlyLeuGlyProGlnGluA
3181 ACTACCCTGACAGGCTGACAGCTGCCTGCTTTGACAGGTGGGACCTGCCTCTGTCTGACA
     snTyrProAspArgLeuThrAlaAlaCysPheAspArgTrpAspLeuProLeuSerAspM
3241 TGTACACCCCTTATGTGTTCCCTTCTGAGAATGGCCTGAGGTGTGGCACCAGGGAGCTGA
     etTyrThrProTyrValPheProSerGluAsnGlyLeuArgCysGlyThrArgGluLeuA
3301 ACTATGGTCCTCACCAGTGGAGGGGAGACTTCCAGTTCAACATCTCCAGGTACTCTCAGC
     snTyrGlyProHisGlnTrpArgGlyAspPheGlnPheAsnIleSerArgTyrSerGlnG
3361 AACAGCTCATGGAAACCTCTCACAGGCACCTGCTCCATGCAGAGGAGGGAACCTGGCTGA
     lnGlnLeuMetGluThrSerHisArgHisLeuLeuHisAlaGluGluGlyThrTrpLeuA
3421 ACATTGATGGCTTCCACATGGGCATTGGAGGAGATGACTCTTGGTCTCCTTCTGTGTCTG
     snIleAspGlyPheHisMetGlyIleGlyGlyAspAspSerTrpSerProSerValSerA
```

Figure 14c

```
3481 CTGAGTTCCAGTTATCTGCTGGCAGGTACCACTATCAGCTGGTGTGGTGCCAGAAGTAAG
     laGluPheGlnLeuSerAlaGlyArgTyrHisTyrGlnLeuValTrpCysGlnLys***    SEQ ID No.15
     NheI                                                 PacI
3541 CTAGCTGAGTTTCAGAAAAGGGGGCCTGAGTGGCCCCTTTTTTCAACTTAATTAACCTTA
3601 AAACCTTTAAAAGCCTTATATATTCTTTTTTTTCTTATAAAACTTAAAACCTTAGAGGCT
3661 ATTTAAGTTGCTGATTTATATTAATTTTATTGTTCAAACATGAGAGCTTAGTACATGAAA
3721 CATGAGAGCTTAGTACATTAGCCATGAGAGCTTAGTACATTAGCCATGAGGGTTTAGTTC
3781 ATTAAACATGAGAGCTTAGTACATTAAACATGAGAGCTTAGTACATACTATCAACAGGTT
3841 GAACTGCTGATC                                                   SEQ ID No.14
```

Figure 15

```
       BspHI
  1   TCATGATTGAACAAGATGGCCTACATGCAGGTTCTCCAGCTGCCTGGGTTGAGAGACTG
  1     MetIleGluGlnAspGlyLeuHisAlaGlySerProAlaAlaTrpValGluArgLeu

 60  TTTGGCTATGACTGGGCACAGCAGACCATTGGTTGCTCTGATGCAGCAGTTTTCAGACTT
 20  PheGlyTyrAspTrpAlaGlnGlnThrIleGlyCysSerAspAlaAlaValPheArgLeu

120  TCAGCCCAAGGCAGGCCAGTCCTTTTTGTAAAGACAGACCTCAGTGGGGCTCTCAATGAG
 40  SerAlaGlnGlyArgProValLeuPheValLysThrAspLeuSerGlyAlaLeuAsnGlu

180  CTCCAGGATGAGGCTGCCAGACTCTCCTGGTTGGCAACAACTGGGGTCCCCTGTGCAGCT
 60  LeuGlnAspGluAlaAlaArgLeuSerTrpLeuAlaThrThrGlyValProCysAlaAla

240  GTCCTTGATGTGGTCACAGAAGCTGGAAGGGACTGGCTCCTACTAGGTGAGGTGCCTGGG
 80  ValLeuAspValValThrGluAlaGlyArgAspTrpLeuLeuLeuGlyGluValProGly

300  CAGGACCTCCTTTCCTCTCACCTAGCTCCAGCTGAGAAAGTGTCAATCATGGCTGATGCC
100  GlnAspLeuLeuSerSerHisLeuAlaProAlaGluLysValSerIleMetAlaAspAla

360  ATGAGAAGACTCCACACCCTTGACCCAGCCACCTGCCCCTTTGACCACCAGGCCAAGCAC
120  MetArgArgLeuHisThrLeuAspProAlaThrCysProPheAspHisGlnAlaLysHis

420  AGGATAGAGAGGGCCAGAACCAGGATGGAGGCTGGCCTGGTGGACCAAGATGACTTGGAT
140  ArgIleGluArgAlaArgThrArgMetGluAlaGlyLeuValAspGlnAspAspLeuAsp

480  GAAGAACACCAGGGCCTGGCCCCTGCTGAACTATTTGCCAGGCTCAAGGCATCCATGCCA
160  GluGluHisGlnGlyLeuAlaProAlaGluLeuPheAlaArgLeuLysAlaSerMetPro

540  GATGGTGAGGACCTAGTGGTGACTCATGGGGATGCCTGCCTTCCCAACATCATGGTTGAA
180  AspGlyGluAspLeuValValThrHisGlyAspAlaCysLeuProAsnIleMetValGlu

600  AATGGAAGGTTCTCTGGCTTCATAGACTGTGGCAGGCTGGGAGTGGCTGACAGGTACCAG
200  AsnGlyArgPheSerGlyPheIleAspCysGlyArgLeuGlyValAlaAspArgTyrGln

660  GACATTGCCCTAGCAACCAGGGACATAGCAGAAGAGCTAGGGGGAGAGTGGGCAGACAGG
220  AspIleAlaLeuAlaThrArgAspIleAlaGluGluLeuGlyGlyGluTrpAlaAspArg

720  TTCCTAGTGCTCTATGGCATTGCAGCCCCTGACTCCCAGAGAATTGCCTTCTACAGACTT
240  PheLeuValLeuTyrGlyIleAlaAlaProAspSerGlnArgIleAlaPheTyrArgLeu
                          NheI
780  CTTGATGAGTTCTTCTAAAGCTAGC   SEQ ID NO: 316 (positions 3 to 797)
260  LeuAspGluPhePhe***          SEQ ID NO: 317
```

Figure 18

SEQ ID NO: 318 CATTACCGGTAGGCACATCATGATTGAACAAGATGGCCTA
SEQ ID NO: 319 CATGCAGGTTCTCCAGCTGCCTGGGTTGAGAGACTGTTTG
SEQ ID NO: 320 GCTATGACTGGGCACAGCAGACCATTGGTTGCTCTGATGC
SEQ ID NO: 321 AGCAGTTTTCAGACTTTCAGCCCAAGGCAGGCCAGTCCTT
SEQ ID NO: 322 TTTGTAAAGACAGACCTCAGTGGGGCTCTCAATGAGCTCC
SEQ ID NO: 323 AGGATGAGGCTGCCAGACTCTCCTGGTTGGCAACAACTGG
SEQ ID NO: 324 GGTCCCCTGTGCAGCTGTCCTTGATGTGGTCACAGAAGCT
SEQ ID NO: 325 GGAAGGGACTGGCTCCTACTAGGTGAGGTGCCTGGGCAGG
SEQ ID NO: 326 ACCTCCTTTCCTCTCACCTAGCTCCAGCTGAGAAAGTGTC
SEQ ID NO: 327 AATCATGGCTGATGCCATGAGAAGACTCCACACCCTTGAC
SEQ ID NO: 328 CCAGCCACCTGCCCCTTTGACCACCAGGCCAAGCACAGGA
SEQ ID NO: 329 TAGAGAGGGCCAGAACCAGGATGGAGGCTGGCCTGGTGGA
SEQ ID NO: 330 CCAAGATGACTTGGATGAAGAACACCAGGGCCTGGCCCCT
SEQ ID NO: 331 GCTGAACTATTTGCCAGGCTCAAGGCATCCATGCCAGATG
SEQ ID NO: 332 GTGAGGACCTAGTGGTGACTCATGGGGATGCCTGCCTTCC
SEQ ID NO: 333 CAACATCATGGTTGAAAATGGAAGGTTCTCTGGCTTCATA
SEQ ID NO: 334 GACTGTGGCAGGCTGGGAGTGGCTGACAGGTACCAGGACA
SEQ ID NO: 335 TTGCCCTAGCAACCAGGGACATAGCAGAAGAGCTAGGGGG
SEQ ID NO: 336 AGAGTGGGCAGACAGGTTCCTAGTGCTCTATGGCATTGCA
SEQ ID NO: 337 GCCCCTGACTCCCAGAGAATTGCCTTCTACAGACTTCTTG
SEQ ID NO: 338 ATGAGTTCTTCTAAAGCTAGCTGATCCTGATAGCTGTTCG
SEQ ID NO: 339 CGAACAGCTATCAGGATCAG
SEQ ID NO: 340 CTAGCTTTAGAAGAACTCATCAAGAAGTCTGTAGAAGGCA
SEQ ID NO: 341 ATTCTCTGGGAGTCAGGGGCTGCAATGCCATAGAGCACTA
SEQ ID NO: 342 GGAACCTGTCTGCCCACTCTCCCCCTAGCTCTTCTGCTAT
SEQ ID NO: 343 GTCCCTGGTTGCTAGGGCAATGTCCTGGTACCTGTCAGCC
SEQ ID NO: 344 ACTCCCAGCCTGCCACAGTCTATGAAGCCAGAGAACCTTC
SEQ ID NO: 345 CATTTTCAACCATGATGTTGGGAAGGCAGGCATCCCCATG
SEQ ID NO: 346 AGTCACCACTAGGTCCTCACCATCTGGCATGGATGCCTTG
SEQ ID NO: 347 AGCCTGGCAAATAGTTCAGCAGGGGCCAGGCCCTGGTGTT
SEQ ID NO: 348 CTTCATCCAAGTCATCTTGGTCCACCAGGCCAGCCTCCAT
SEQ ID NO: 349 CCTGGTTCTGGCCCTCTCTATCCTGTGCTTGGCCTGGTGG
SEQ ID NO: 350 TCAAAGGGGCAGGTGGCTGGGTCAAGGGTGTGGAGTCTTC
SEQ ID NO: 351 TCATGGCATCAGCCATGATTGACACTTTCTCAGCTGGAGC
SEQ ID NO: 352 TAGGTGAGAGGAAAGGAGGTCCTGCCCAGGCACCTCACCT
SEQ ID NO: 353 AGTAGGAGCCAGTCCCTTCCAGCTTCTGTGACCACATCAA
SEQ ID NO: 354 GGACAGCTGCACAGGGGACCCCAGTTGTTGCCAACCAGGA
SEQ ID NO: 355 GAGTCTGGCAGCCTCATCCTGGAGCTCATTGAGAGCCCCA
SEQ ID NO: 356 CTGAGGTCTGTCTTTACAAAAAGGACTGGCCTGCCTTGGG
SEQ ID NO: 357 CTGAAAGTCTGAAAACTGCTGCATCAGAGCAACCAATGGT
SEQ ID NO: 358 CTGCTGTGCCCAGTCATAGCCAAACAGTCTCTCAACCCAG
SEQ ID NO: 359 GCAGCTGGAGAACCTGCATGTAGGCCATCTTGTTCAATCA
SEQ ID NO: 360 TGATGTGCCTACCGGTAATG

FIGURE 19

SEQUENCE LISTING

```
<160> NUMBER OF SEQ ID NOS: 360

<210> SEQ ID NO 1
<211> LENGTH: 396
<212> TYPE: DNA
<213> ORGANISM: Artificial Sequence
<220> FEATURE:
<223> OTHER INFORMATION: CpG-Free Sh ble
```

-continued

```
<220> FEATURE:
<221> NAME/KEY: CDS
<222> LOCATION: (3)..(374)
<223> OTHER INFORMATION:

<400> SEQUENCE: 1

cc atg gcc aag ttg acc agt gct gtc cca gtg ctc aca gcc agg gat       47
   Met Ala Lys Leu Thr Ser Ala Val Pro Val Leu Thr Ala Arg Asp
   1               5                   10                  15

gtg gct gga gct gtt gag ttc tgg act gac agg ttg ggg ttc tcc aga       95
Val Ala Gly Ala Val Glu Phe Trp Thr Asp Arg Leu Gly Phe Ser Arg
                20                  25                  30

gat ttt gtg gag gat gac ttt gca ggt gtg gtc aga gat gat gtc acc      143
Asp Phe Val Glu Asp Asp Phe Ala Gly Val Val Arg Asp Asp Val Thr
            35                  40                  45

ctg ttc atc tca gca gtc cag gac cag gtg gtg cct gac aac acc ctg      191
Leu Phe Ile Ser Ala Val Gln Asp Gln Val Val Pro Asp Asn Thr Leu
        50                  55                  60

gct tgg gtg tgg gtg aga gga ctg gat gag ctg tat gct gag tgg agt      239
Ala Trp Val Trp Val Arg Gly Leu Asp Glu Leu Tyr Ala Glu Trp Ser
    65                  70                  75

gag gtg gtc tcc acc aac ttc agg gat gcc agt ggc cct gcc atg aca      287
Glu Val Val Ser Thr Asn Phe Arg Asp Ala Ser Gly Pro Ala Met Thr
80                  85                  90                  95

gag att gga gag cag ccc tgg ggg aga gag ttt gcc ctg aga gac cca      335
Glu Ile Gly Glu Gln Pro Trp Gly Arg Glu Phe Ala Leu Arg Asp Pro
                100                 105                 110

gca ggc aac tgt gtg cac ttt gtg gca gag gag cag gac tgaggataag       384
Ala Gly Asn Cys Val His Phe Val Ala Glu Glu Gln Asp
            115                 120

aattcagcta gc                                                        396


<210> SEQ ID NO 2
<211> LENGTH: 124
<212> TYPE: PRT
<213> ORGANISM: Artificial Sequence
<220> FEATURE:
<223> OTHER INFORMATION: CpG-Free Sh ble

<400> SEQUENCE: 2

Met Ala Lys Leu Thr Ser Ala Val Pro Val Leu Thr Ala Arg Asp Val
1               5                   10                  15

Ala Gly Ala Val Glu Phe Trp Thr Asp Arg Leu Gly Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
        115                 120


<210> SEQ ID NO 3
<211> LENGTH: 1040
<212> TYPE: DNA
```

-continued

```
<213> ORGANISM: Artificial Sequence
<220> FEATURE:
<223> OTHER INFORMATION: CpG-Free Hph
<220> FEATURE:
<221> NAME/KEY: CDS
<222> LOCATION: (3)..(1025)
<223> OTHER INFORMATION:

<400> SEQUENCE: 3

tc atg aag aaa cct gaa ctg aca gca act tct gtt gag aag ttt ctc        47
   Met Lys Lys Pro Glu Leu Thr Ala Thr Ser Val Glu Lys Phe Leu
   1               5                   10                  15

att gaa aaa ttt gat tct gtt tct gat ctc atg cag ctg tct gaa ggt        95
Ile Glu Lys Phe Asp Ser Val Ser Asp Leu Met Gln Leu Ser Glu Gly
                20                  25                  30

gaa gaa agc aga gcc ttt tct ttt gat gtt gga gga aga ggt tat gtt       143
Glu Glu Ser Arg Ala Phe Ser Phe Asp Val Gly Gly Arg Gly Tyr Val
            35                  40                  45

ctg agg gtc aat tct tgt gct gat ggt ttt tac aaa gac aga tat gtt       191
Leu Arg Val Asn Ser Cys Ala Asp Gly Phe Tyr Lys Asp Arg Tyr Val
        50                  55                  60

tac aga cac ttt gcc tct gct gct ctg cca att cca gaa gtt ctg gac       239
Tyr Arg His Phe Ala Ser Ala Ala Leu Pro Ile Pro Glu Val Leu Asp
    65                  70                  75

att gga gaa ttt tct gaa tct ctc acc tac tgc atc agc aga aga gca       287
Ile Gly Glu Phe Ser Glu Ser Leu Thr Tyr Cys Ile Ser Arg Arg Ala
80                  85                  90                  95

caa gga gtc act ctc cag gat ctc cct gaa act gag ctg cca gct gtt       335
Gln Gly Val Thr Leu Gln Asp Leu Pro Glu Thr Glu Leu Pro Ala Val
                100                 105                 110

ctg caa cct gtt gct gaa gca atg gat gcc att gca gca gct gat ctg       383
Leu Gln Pro Val Ala Glu Ala Met Asp Ala Ile Ala Ala Ala Asp Leu
            115                 120                 125

agc caa acc tct gga ttt ggt cct ttt ggt ccc caa ggc att ggt cag       431
Ser Gln Thr Ser Gly Phe Gly Pro Phe Gly Pro Gln Gly Ile Gly Gln
        130                 135                 140

tac acc act tgg agg gat ttc att tgt gcc att gct gat cct cat gtc       479
Tyr Thr Thr Trp Arg Asp Phe Ile Cys Ala Ile Ala Asp Pro His Val
    145                 150                 155

tat cac tgg cag act gtg atg gat gac aca gtt tct gct tct gtt gct       527
Tyr His Trp Gln Thr Val Met Asp Asp Thr Val Ser Ala Ser Val Ala
160                 165                 170                 175

cag gca ctg gat gaa ctc atg ctg tgg gca gaa gat tgt cct gaa gtc       575
Gln Ala Leu Asp Glu Leu Met Leu Trp Ala Glu Asp Cys Pro Glu Val
                180                 185                 190

aga cac ctg gtc cat gct gat ttt gga agc aac aat gtt ctg aca gac       623
Arg His Leu Val His Ala Asp Phe Gly Ser Asn Asn Val Leu Thr Asp
            195                 200                 205

aat ggc aga atc act gca gtc att gac tgg tct gaa gcc atg ttt gga       671
Asn Gly Arg Ile Thr Ala Val Ile Asp Trp Ser Glu Ala Met Phe Gly
        210                 215                 220

gat tct caa tat gag gtt gcc aac att ttt ttt tgg aga cct tgg ctg       719
Asp Ser Gln Tyr Glu Val Ala Asn Ile Phe Phe Trp Arg Pro Trp Leu
    225                 230                 235

gct tgc atg gaa caa caa aca aga tat ttt gaa aga aga cac cca gaa       767
Ala Cys Met Glu Gln Gln Thr Arg Tyr Phe Glu Arg Arg His Pro Glu
240                 245                 250                 255

ctg gct ggt tcc ccc aga ctg aga gcc tac atg ctc aga att ggc ctg       815
Leu Ala Gly Ser Pro Arg Leu Arg Ala Tyr Met Leu Arg Ile Gly Leu
                260                 265                 270

gac caa ctg tat caa tct ctg gtt gat gga aac ttt gat gat gct gct       863
```

-continued

```
Asp Gln Leu Tyr Gln Ser Leu Val Asp Gly Asn Phe Asp Asp Ala Ala
            275                 280                 285

tgg gca caa gga aga tgt gat gcc att gtg agg tct ggt gct gga act      911
Trp Ala Gln Gly Arg Cys Asp Ala Ile Val Arg Ser Gly Ala Gly Thr
        290                 295                 300

gtt gga aga act caa att gca aga agg tct gct gct gtt tgg act gat      959
Val Gly Arg Thr Gln Ile Ala Arg Arg Ser Ala Ala Val Trp Thr Asp
    305                 310                 315

gga tgt gtt gaa gtt ctg gct gac tct gga aac agg aga ccc tcc aca     1007
Gly Cys Val Glu Val Leu Ala Asp Ser Gly Asn Arg Arg Pro Ser Thr
320                 325                 330                 335

aga ccc aga gcc aag gaa tgaatattag ctagc                            1040
Arg Pro Arg Ala Lys Glu
                340


<210> SEQ ID NO 4
<211> LENGTH: 341
<212> TYPE: PRT
<213> ORGANISM: Artificial Sequence
<220> FEATURE:
<223> OTHER INFORMATION: CpG-Free Hph

<400> SEQUENCE: 4

Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270
```

```
Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
    290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Arg Ala Lys Glu
            340


<210> SEQ ID NO 5
<211> LENGTH: 442
<212> TYPE: DNA
<213> ORGANISM: Artificial Sequence
<220> FEATURE:
<223> OTHER INFORMATION: CpG-Free Bsr
<220> FEATURE:
<221> NAME/KEY: CDS
<222> LOCATION: (3)..(422)
<223> OTHER INFORMATION:

<400> SEQUENCE: 5

tc atg aag acc ttc aac atc tct cag cag gat ctg gag ctg gtg gag        47
   Met Lys Thr Phe Asn Ile Ser Gln Gln Asp Leu Glu Leu Val Glu
   1               5                   10                  15

gtc gcc act gag aag atc acc atg ctc tat gag gac aac aag cac cat       95
Val Ala Thr Glu Lys Ile Thr Met Leu Tyr Glu Asp Asn Lys His His
                20                  25                  30

gtc ggg gcg gcc atc agg acc aag act ggg gag atc atc tct gct gtc      143
Val Gly Ala Ala Ile Arg Thr Lys Thr Gly Glu Ile Ile Ser Ala Val
            35                  40                  45

cac att gag gcc tac att ggc agg gtc act gtc tgt gct gaa gcc att      191
His Ile Glu Ala Tyr Ile Gly Arg Val Thr Val Cys Ala Glu Ala Ile
        50                  55                  60

gcc att ggg tct gct gtg agc aac ggg cag aag gac ttt gac acc att      239
Ala Ile Gly Ser Ala Val Ser Asn Gly Gln Lys Asp Phe Asp Thr Ile
    65                  70                  75

gtg gct gtc agg cac ccc tac tct gat gag gtg gac aga tcc atc agg      287
Val Ala Val Arg His Pro Tyr Ser Asp Glu Val Asp Arg Ser Ile Arg
80                  85                  90                  95

gtg gtc agc ccc tgt ggc atg tgc aga gag ctc atc tct gac tat gct      335
Val Val Ser Pro Cys Gly Met Cys Arg Glu Leu Ile Ser Asp Tyr Ala
                100                 105                 110

cct gac tgc ttt gtg ctc att gag atg aat ggc aag ctg gtc aaa acc      383
Pro Asp Cys Phe Val Leu Ile Glu Met Asn Gly Lys Leu Val Lys Thr
            115                 120                 125

acc att gag gaa ctc atc ccc ctc aag tac acc agg aac taaacctgaa       432
Thr Ile Glu Glu Leu Ile Pro Leu Lys Tyr Thr Arg Asn
        130                 135                 140

ttcagctagc                                                           442


<210> SEQ ID NO 6
<211> LENGTH: 140
<212> TYPE: PRT
<213> ORGANISM: Artificial Sequence
<220> FEATURE:
<223> OTHER INFORMATION: CpG-Free Bsr

<400> SEQUENCE: 6

Met Lys Thr Phe Asn Ile Ser Gln Gln Asp Leu Glu Leu Val Glu Val
```

-continued

```
1               5                   10                  15

Ala Thr Glu Lys Ile Thr Met Leu Tyr Glu Asp Asn Lys His His Val
            20                  25                  30

Gly Ala Ala Ile Arg Thr Lys Thr Gly Glu Ile Ile Ser Ala Val His
        35                  40                  45

Ile Glu Ala Tyr Ile Gly Arg Val Thr Val Cys Ala Glu Ala Ile Ala
    50                  55                  60

Ile Gly Ser Ala Val Ser Asn Gly Gln Lys Asp Phe Asp Thr Ile Val
65                  70                  75                  80

Ala Val Arg His Pro Tyr Ser Asp Glu Val Asp Arg Ser Ile Arg Val
                85                  90                  95

Val Ser Pro Cys Gly Met Cys Arg Glu Leu Ile Ser Asp Tyr Ala Pro
            100                 105                 110

Asp Cys Phe Val Leu Ile Glu Met Asn Gly Lys Leu Val Lys Thr Thr
        115                 120                 125

Ile Glu Glu Leu Ile Pro Leu Lys Tyr Thr Arg Asn
    130                 135                 140


<210> SEQ ID NO 7
<211> LENGTH: 614
<212> TYPE: DNA
<213> ORGANISM: Artificial Sequence
<220> FEATURE:
<223> OTHER INFORMATION: CpG-Free Pac
<220> FEATURE:
<221> NAME/KEY: CDS
<222> LOCATION: (3)..(599)
<223> OTHER INFORMATION:

<400> SEQUENCE: 7

tc atg act gag tac aaa ccc aca gtg agg ctg gca acc aga gat gat        47
   Met Thr Glu Tyr Lys Pro Thr Val Arg Leu Ala Thr Arg Asp Asp
   1               5                   10                  15

gtt cca aga gct gtg aga aca ctg gct gct gct ttt gca gac tac cct       95
Val Pro Arg Ala Val Arg Thr Leu Ala Ala Ala Phe Ala Asp Tyr Pro
                20                  25                  30

gca aca agg cac aca gtt gac cct gac agg cac att gag agg gtg aca      143
Ala Thr Arg His Thr Val Asp Pro Asp Arg His Ile Glu Arg Val Thr
            35                  40                  45

gaa ctg caa gaa ctc ttc ctc acc aga gtg gga ctg gac att gga aaa      191
Glu Leu Gln Glu Leu Phe Leu Thr Arg Val Gly Leu Asp Ile Gly Lys
        50                  55                  60

gtt tgg gtt gca gat gat gga gct gct gtt gca gtt tgg aca aca cct      239
Val Trp Val Ala Asp Asp Gly Ala Ala Val Ala Val Trp Thr Thr Pro
    65                  70                  75

gag tct gtt gaa gct ggt gct gtt ttt gct gaa att gga cca aga atg      287
Glu Ser Val Glu Ala Gly Ala Val Phe Ala Glu Ile Gly Pro Arg Met
80                  85                  90                  95

gct gag ctc tct gga agc agg ctg gca gca caa caa caa atg gaa ggt      335
Ala Glu Leu Ser Gly Ser Arg Leu Ala Ala Gln Gln Gln Met Glu Gly
                100                 105                 110

ctg ctg gca cca cac agg cca aaa gag cca gct tgg ttt ctg gca act      383
Leu Leu Ala Pro His Arg Pro Lys Glu Pro Ala Trp Phe Leu Ala Thr
            115                 120                 125

gtt gga gtg agc cct gac cac cag gga aag ggt ctg gga tct gct gtt      431
Val Gly Val Ser Pro Asp His Gln Gly Lys Gly Leu Gly Ser Ala Val
        130                 135                 140

gtt ctg cct gga gtt gaa gct gct gaa agg gct gga gtt cct gcc ttt      479
Val Leu Pro Gly Val Glu Ala Ala Glu Arg Ala Gly Val Pro Ala Phe
    145                 150                 155
```

```
ctg gaa act tct gct ccc aga aac ctg cct ttt tat gaa aga ctg gga      527
Leu Glu Thr Ser Ala Pro Arg Asn Leu Pro Phe Tyr Glu Arg Leu Gly
160                 165                 170                 175

ttc act gtg aca gct gat gtt gag gtt cca gaa ggc cca aga act tgg      575
Phe Thr Val Thr Ala Asp Val Glu Val Pro Glu Gly Pro Arg Thr Trp
                180                 185                 190

tgc atg aca agg aag cct gga gct taaacctgag ctagc                     614
Cys Met Thr Arg Lys Pro Gly Ala
            195
```

```
<210> SEQ ID NO 8
<211> LENGTH: 199
<212> TYPE: PRT
<213> ORGANISM: Artificial Sequence
<220> FEATURE:
<223> OTHER INFORMATION: CpG-Free Pac

<400> SEQUENCE: 8

Met Thr Glu Tyr Lys Pro Thr Val Arg Leu Ala Thr Arg Asp Asp Val
1               5                   10                  15

Pro Arg Ala Val Arg Thr Leu Ala Ala Ala Phe Ala Asp Tyr Pro Ala
            20                  25                  30

Thr Arg His Thr Val Asp Pro Asp Arg His Ile Glu Arg Val Thr Glu
        35                  40                  45

Leu Gln Glu Leu Phe Leu Thr Arg Val Gly Leu Asp Ile Gly Lys Val
    50                  55                  60

Trp Val Ala Asp Asp Gly Ala Ala Val Ala Val Trp Thr Thr Pro Glu
65                  70                  75                  80

Ser Val Glu Ala Gly Ala Val Phe Ala Glu Ile Gly Pro Arg Met Ala
                85                  90                  95

Glu Leu Ser Gly Ser Arg Leu Ala Ala Gln Gln Gln Met Glu Gly Leu
            100                 105                 110

Leu Ala Pro His Arg Pro Lys Glu Pro Ala Trp Phe Leu Ala Thr Val
        115                 120                 125

Gly Val Ser Pro Asp His Gln Gly Lys Gly Leu Gly Ser Ala Val Val
    130                 135                 140

Leu Pro Gly Val Glu Ala Ala Glu Arg Ala Gly Val Pro Ala Phe Leu
145                 150                 155                 160

Glu Thr Ser Ala Pro Arg Asn Leu Pro Phe Tyr Glu Arg Leu Gly Phe
                165                 170                 175

Thr Val Thr Ala Asp Val Glu Val Pro Glu Gly Pro Arg Thr Trp Cys
            180                 185                 190

Met Thr Arg Lys Pro Gly Ala
        195
```

```
<210> SEQ ID NO 9
<211> LENGTH: 3071
<212> TYPE: DNA
<213> ORGANISM: Artificial Sequence
<220> FEATURE:
<223> OTHER INFORMATION: CpG-Free LacZ
<220> FEATURE:
<221> NAME/KEY: CDS
<222> LOCATION: (3)..(3056)
<223> OTHER INFORMATION:

<400> SEQUENCE: 9

cc atg gac cct gtt gtg ctg caa agg aga gac tgg gag aac cct gga      47
   Met Asp Pro Val Val Leu Gln Arg Arg Asp Trp Glu Asn Pro Gly
   1               5                   10                  15
```

-continued

```
gtg acc cag ctc aac aga ctg gct gcc cac cct ccc ttt gcc tct tgg       95
Val Thr Gln Leu Asn Arg Leu Ala Ala His Pro Pro Phe Ala Ser Trp
            20                  25                  30

agg aac tct gag gaa gcc agg aca gac agg ccc agc cag cag ctc agg      143
Arg Asn Ser Glu Glu Ala Arg Thr Asp Arg Pro Ser Gln Gln Leu Arg
        35                  40                  45

tct ctc aat gga gag tgg agg ttt gcc tgg ttc cct gcc cct gaa gct      191
Ser Leu Asn Gly Glu Trp Arg Phe Ala Trp Phe Pro Ala Pro Glu Ala
    50                  55                  60

gtg cct gag tct tgg ctg gag tgt gac ctc cca gag gct gac act gtt      239
Val Pro Glu Ser Trp Leu Glu Cys Asp Leu Pro Glu Ala Asp Thr Val
65                  70                  75

gtg gtg ccc agc aac tgg cag atg cat ggc tat gat gcc ccc atc tac      287
Val Val Pro Ser Asn Trp Gln Met His Gly Tyr Asp Ala Pro Ile Tyr
80                  85                  90                  95

acc aat gtc acc tac ccc atc act gtg aac ccc cct ttt gtg ccc act      335
Thr Asn Val Thr Tyr Pro Ile Thr Val Asn Pro Pro Phe Val Pro Thr
            100                 105                 110

gag aac ccc act ggc tgc tac agc ctg acc ttc aat gtt gat gag agc      383
Glu Asn Pro Thr Gly Cys Tyr Ser Leu Thr Phe Asn Val Asp Glu Ser
        115                 120                 125

tgg ctg caa gaa ggc cag acc agg atc atc ttt gat gga gtc aac tct      431
Trp Leu Gln Glu Gly Gln Thr Arg Ile Ile Phe Asp Gly Val Asn Ser
    130                 135                 140

gcc ttc cac ctc tgg tgc aat ggc agg tgg gtt ggc tat ggc caa gac      479
Ala Phe His Leu Trp Cys Asn Gly Arg Trp Val Gly Tyr Gly Gln Asp
    145                 150                 155

agc agg ctg ccc tct gag ttt gac ctc tct gcc ttc ctc aga gct gga      527
Ser Arg Leu Pro Ser Glu Phe Asp Leu Ser Ala Phe Leu Arg Ala Gly
160                 165                 170                 175

gag aac agg ctg gct gtc atg gtg ctc agg tgg tct gat ggc agc tac      575
Glu Asn Arg Leu Ala Val Met Val Leu Arg Trp Ser Asp Gly Ser Tyr
            180                 185                 190

ctg gaa gac caa gac atg tgg agg atg tct ggc atc ttc agg gat gtg      623
Leu Glu Asp Gln Asp Met Trp Arg Met Ser Gly Ile Phe Arg Asp Val
        195                 200                 205

agc ctg ctg cac aag ccc acc acc cag att tct gac ttc cat gtt gcc      671
Ser Leu Leu His Lys Pro Thr Thr Gln Ile Ser Asp Phe His Val Ala
    210                 215                 220

acc agg ttc aat gat gac ttc agc aga gct gtg ctg gag gct gag gtg      719
Thr Arg Phe Asn Asp Asp Phe Ser Arg Ala Val Leu Glu Ala Glu Val
    225                 230                 235

cag atg tgt gga gaa ctc aga gac tac ctg aga gtc aca gtg agc ctc      767
Gln Met Cys Gly Glu Leu Arg Asp Tyr Leu Arg Val Thr Val Ser Leu
240                 245                 250                 255

tgg caa ggt gag acc cag gtg gcc tct ggc aca gcc ccc ttt gga gga      815
Trp Gln Gly Glu Thr Gln Val Ala Ser Gly Thr Ala Pro Phe Gly Gly
            260                 265                 270

gag atc att gat gag aga gga ggc tat gct gac aga gtc acc ctg agg      863
Glu Ile Ile Asp Glu Arg Gly Gly Tyr Ala Asp Arg Val Thr Leu Arg
        275                 280                 285

ctc aat gtg gag aac ccc aag ctg tgg tct gct gag atc ccc aac ctc      911
Leu Asn Val Glu Asn Pro Lys Leu Trp Ser Ala Glu Ile Pro Asn Leu
    290                 295                 300

tac agg gct gtt gtg gag ctg cac act gct gat ggc acc ctg att gaa      959
Tyr Arg Ala Val Val Glu Leu His Thr Ala Asp Gly Thr Leu Ile Glu
    305                 310                 315

gct gaa gcc tgt gat gtt gga ttc aga gaa gtc agg att gag aat ggc     1007
Ala Glu Ala Cys Asp Val Gly Phe Arg Glu Val Arg Ile Glu Asn Gly
```

-continued

```
320                 325                 330                 335

ctg ctg ctg ctc aat ggc aag cct ctg ctc atc agg gga gtc aac agg      1055
Leu Leu Leu Leu Asn Gly Lys Pro Leu Leu Ile Arg Gly Val Asn Arg
                340                 345                 350

cat gag cac cac cct ctg cat gga caa gtg atg gat gaa cag aca atg      1103
His Glu His His Pro Leu His Gly Gln Val Met Asp Glu Gln Thr Met
            355                 360                 365

gtg caa gat atc ctg cta atg aag cag aac aac ttc aat gct gtc agg      1151
Val Gln Asp Ile Leu Leu Met Lys Gln Asn Asn Phe Asn Ala Val Arg
        370                 375                 380

tgc tct cac tac ccc aac cac cct ctc tgg tac acc ctg tgt gac agg      1199
Cys Ser His Tyr Pro Asn His Pro Leu Trp Tyr Thr Leu Cys Asp Arg
    385                 390                 395

tat ggc ctg tat gtt gtt gat gaa gcc aac att gag aca cat ggc atg      1247
Tyr Gly Leu Tyr Val Val Asp Glu Ala Asn Ile Glu Thr His Gly Met
400                 405                 410                 415

gtg ccc atg aac agg ctc aca gat gac ccc agg tgg ctg cct gcc atg      1295
Val Pro Met Asn Arg Leu Thr Asp Asp Pro Arg Trp Leu Pro Ala Met
                420                 425                 430

tct gag aga gtg acc agg atg gtg cag aga gac agg aac cac ccc tct      1343
Ser Glu Arg Val Thr Arg Met Val Gln Arg Asp Arg Asn His Pro Ser
            435                 440                 445

gtg atc atc tgg tct ctg ggc aat gag tct gga cat gga gcc aac cat      1391
Val Ile Ile Trp Ser Leu Gly Asn Glu Ser Gly His Gly Ala Asn His
        450                 455                 460

gat gct ctc tac agg tgg atc aag tct gtt gac ccc agc aga cct gtg      1439
Asp Ala Leu Tyr Arg Trp Ile Lys Ser Val Asp Pro Ser Arg Pro Val
    465                 470                 475

cag tat gaa gga ggt gga gca gac acc aca gcc aca gac atc atc tgc      1487
Gln Tyr Glu Gly Gly Gly Ala Asp Thr Thr Ala Thr Asp Ile Ile Cys
480                 485                 490                 495

ccc atg tat gcc agg gtt gat gag gac cag ccc ttc cct gct gtg ccc      1535
Pro Met Tyr Ala Arg Val Asp Glu Asp Gln Pro Phe Pro Ala Val Pro
                500                 505                 510

aag tgg agc atc aag aag tgg ctc tct ctg cct gga gag acc aga cct      1583
Lys Trp Ser Ile Lys Lys Trp Leu Ser Leu Pro Gly Glu Thr Arg Pro
            515                 520                 525

ctg atc ctg tgt gaa tat gca cat gca atg ggc aac tct ctg gga ggc      1631
Leu Ile Leu Cys Glu Tyr Ala His Ala Met Gly Asn Ser Leu Gly Gly
        530                 535                 540

ttt gcc aag tac tgg caa gcc ttc aga cag tac ccc agg ctg caa gga      1679
Phe Ala Lys Tyr Trp Gln Ala Phe Arg Gln Tyr Pro Arg Leu Gln Gly
    545                 550                 555

gga ttt gtg tgg gac tgg gtg gac caa tct ctc atc aag tat gat gag      1727
Gly Phe Val Trp Asp Trp Val Asp Gln Ser Leu Ile Lys Tyr Asp Glu
560                 565                 570                 575

aat ggc aac ccc tgg tct gcc tat gga gga gac ttt ggt gac acc ccc      1775
Asn Gly Asn Pro Trp Ser Ala Tyr Gly Gly Asp Phe Gly Asp Thr Pro
                580                 585                 590

aat gac agg cag ttc tgc atg aat ggc ctg gtc ttt gca gac agg acc      1823
Asn Asp Arg Gln Phe Cys Met Asn Gly Leu Val Phe Ala Asp Arg Thr
            595                 600                 605

cct cac cct gcc ctc aca gag gcc aag cac cag caa cag ttc ttc cag      1871
Pro His Pro Ala Leu Thr Glu Ala Lys His Gln Gln Gln Phe Phe Gln
        610                 615                 620

ttc agg ctg tct gga cag acc att gag gtg aca tct gag tac ctc ttc      1919
Phe Arg Leu Ser Gly Gln Thr Ile Glu Val Thr Ser Glu Tyr Leu Phe
    625                 630                 635

agg cac tct gac aat gag ctc ctg cac tgg atg gtg gcc ctg gat ggc      1967
```

-continued

```
Arg His Ser Asp Asn Glu Leu Leu His Trp Met Val Ala Leu Asp Gly
640                 645                 650                 655

aag cct ctg gct tct ggt gag gtg cct ctg gat gtg gcc cct caa gga      2015
Lys Pro Leu Ala Ser Gly Glu Val Pro Leu Asp Val Ala Pro Gln Gly
                660                 665                 670

aag cag ctg att gaa ctg cct gag ctg cct cag cca gag tct gct gga      2063
Lys Gln Leu Ile Glu Leu Pro Glu Leu Pro Gln Pro Glu Ser Ala Gly
            675                 680                 685

caa ctg tgg cta aca gtg agg gtg gtt cag ccc aat gca aca gct tgg      2111
Gln Leu Trp Leu Thr Val Arg Val Val Gln Pro Asn Ala Thr Ala Trp
        690                 695                 700

tct gag gca ggc cac atc tct gca tgg cag cag tgg agg ctg gct gag      2159
Ser Glu Ala Gly His Ile Ser Ala Trp Gln Gln Trp Arg Leu Ala Glu
    705                 710                 715

aac ctc tct gtg acc ctg cct gct gcc tct cat gcc atc cct cac ctg      2207
Asn Leu Ser Val Thr Leu Pro Ala Ala Ser His Ala Ile Pro His Leu
720                 725                 730                 735

aca aca tct gaa atg gac ttc tgc att gag ctg ggc aac aag aga tgg      2255
Thr Thr Ser Glu Met Asp Phe Cys Ile Glu Leu Gly Asn Lys Arg Trp
                740                 745                 750

cag ttc aac agg cag tct ggc ttc ctg tct cag atg tgg att gga gac      2303
Gln Phe Asn Arg Gln Ser Gly Phe Leu Ser Gln Met Trp Ile Gly Asp
            755                 760                 765

aag aag cag ctc ctc acc cct ctc agg gac caa ttc acc agg gct cct      2351
Lys Lys Gln Leu Leu Thr Pro Leu Arg Asp Gln Phe Thr Arg Ala Pro
        770                 775                 780

ctg gac aat gac att gga gtg tct gag gcc acc agg att gac cca aat      2399
Leu Asp Asn Asp Ile Gly Val Ser Glu Ala Thr Arg Ile Asp Pro Asn
    785                 790                 795

gct tgg gtg gag agg tgg aag gct gct gga cac tac cag gct gag gct      2447
Ala Trp Val Glu Arg Trp Lys Ala Ala Gly His Tyr Gln Ala Glu Ala
800                 805                 810                 815

gcc ctg ctc cag tgc aca gca gac acc ctg gct gat gct gtt ctg atc      2495
Ala Leu Leu Gln Cys Thr Ala Asp Thr Leu Ala Asp Ala Val Leu Ile
                820                 825                 830

acc aca gcc cat gct tgg cag cac caa ggc aag acc ctg ttc atc agc      2543
Thr Thr Ala His Ala Trp Gln His Gln Gly Lys Thr Leu Phe Ile Ser
            835                 840                 845

aga aag acc tac agg att gat ggc tct gga cag atg gca atc aca gtg      2591
Arg Lys Thr Tyr Arg Ile Asp Gly Ser Gly Gln Met Ala Ile Thr Val
        850                 855                 860

gat gtg gag gtt gcc tct gac aca cct cac cct gca agg att ggc ctg      2639
Asp Val Glu Val Ala Ser Asp Thr Pro His Pro Ala Arg Ile Gly Leu
    865                 870                 875

aac tgt caa ctg gca cag gtg gct gag agg gtg aac tgg ctg ggc tta      2687
Asn Cys Gln Leu Ala Gln Val Ala Glu Arg Val Asn Trp Leu Gly Leu
880                 885                 890                 895

ggc cct cag gag aac tac cct gac agg ctg aca gct gcc tgc ttt gac      2735
Gly Pro Gln Glu Asn Tyr Pro Asp Arg Leu Thr Ala Ala Cys Phe Asp
                900                 905                 910

agg tgg gac ctg cct ctg tct gac atg tac acc cct tat gtg ttc cct      2783
Arg Trp Asp Leu Pro Leu Ser Asp Met Tyr Thr Pro Tyr Val Phe Pro
            915                 920                 925

tct gag aat ggc ctg agg tgt ggc acc agg gag ctg aac tat ggt cct      2831
Ser Glu Asn Gly Leu Arg Cys Gly Thr Arg Glu Leu Asn Tyr Gly Pro
        930                 935                 940

cac cag tgg agg gga gac ttc cag ttc aac atc tcc agg tac tct cag      2879
His Gln Trp Arg Gly Asp Phe Gln Phe Asn Ile Ser Arg Tyr Ser Gln
    945                 950                 955
```

-continued

```
caa cag ctc atg gaa acc tct cac agg cac ctg ctc cat gca gag gag     2927
Gln Gln Leu Met Glu Thr Ser His Arg His Leu Leu His Ala Glu Glu
960                 965                 970                 975

gga acc tgg ctg aac att gat ggc ttc cac atg ggc att gga gga gat     2975
Gly Thr Trp Leu Asn Ile Asp Gly Phe His Met Gly Ile Gly Gly Asp
                980                 985                 990

gac tct tgg tct cct tct gtg tct gct  gag ttc cag tta tct  gct ggc   3023
Asp Ser Trp Ser Pro Ser Val Ser Ala  Glu Phe Gln Leu Ser  Ala Gly
            995                 1000                 1005

agg tac cac  tat cag ctg gtg tgg  tgc cag aag taaacctgag ctagc      3071
Arg Tyr His  Tyr Gln Leu Val Trp  Cys Gln Lys
        1010                 1015


<210> SEQ ID NO 10
<211> LENGTH: 1018
<212> TYPE: PRT
<213> ORGANISM: Artificial Sequence
<220> FEATURE:
<223> OTHER INFORMATION: CpG-Free LacZ

<400> SEQUENCE: 10

Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Trp Arg
            20                  25                  30

Asn Ser Glu Glu Ala Arg Thr Asp Arg Pro Ser Gln Gln Leu Arg Ser
        35                  40                  45

Leu Asn Gly Glu Trp Arg Phe Ala Trp Phe Pro Ala Pro Glu Ala Val
    50                  55                  60

Pro Glu Ser Trp Leu Glu Cys Asp Leu Pro Glu Ala Asp Thr Val Val
65                  70                  75                  80

Val Pro Ser Asn Trp Gln Met His Gly Tyr Asp Ala Pro Ile Tyr Thr
                85                  90                  95

Asn Val Thr Tyr Pro Ile Thr Val Asn Pro Pro Phe Val Pro Thr Glu
            100                 105                 110

Asn Pro Thr Gly Cys Tyr Ser Leu Thr Phe Asn Val Asp Glu Ser Trp
        115                 120                 125

Leu Gln Glu Gly Gln Thr Arg Ile Ile Phe Asp Gly Val Asn Ser Ala
    130                 135                 140

Phe His Leu Trp Cys Asn Gly Arg Trp Val Gly Tyr Gly Gln Asp Ser
145                 150                 155                 160

Arg Leu Pro Ser Glu Phe Asp Leu Ser Ala Phe Leu Arg Ala Gly Glu
                165                 170                 175

Asn Arg Leu Ala Val Met Val Leu Arg Trp Ser Asp Gly Ser Tyr Leu
            180                 185                 190

Glu Asp Gln Asp Met Trp Arg Met Ser Gly Ile Phe Arg Asp Val Ser
        195                 200                 205

Leu Leu His Lys Pro Thr Thr Gln Ile Ser Asp Phe His Val Ala Thr
    210                 215                 220

Arg Phe Asn Asp Asp Phe Ser Arg Ala Val Leu Glu Ala Glu Val Gln
225                 230                 235                 240

Met Cys Gly Glu Leu Arg Asp Tyr Leu Arg Val Thr Val Ser Leu Trp
                245                 250                 255

Gln Gly Glu Thr Gln Val Ala Ser Gly Thr Ala Pro Phe Gly Gly Glu
            260                 265                 270

Ile Ile Asp Glu Arg Gly Gly Tyr Ala Asp Arg Val Thr Leu Arg Leu
        275                 280                 285
```

-continued

```
Asn Val Glu Asn Pro Lys Leu Trp Ser Ala Glu Ile Pro Asn Leu Tyr
    290                 295                 300

Arg Ala Val Val Glu Leu His Thr Ala Asp Gly Thr Leu Ile Glu Ala
305                 310                 315                 320

Glu Ala Cys Asp Val Gly Phe Arg Glu Val Arg Ile Glu Asn Gly Leu
                325                 330                 335

Leu Leu Leu Asn Gly Lys Pro Leu Leu Ile Arg Gly Val Asn Arg His
            340                 345                 350

Glu His His Pro Leu His Gly Gln Val Met Asp Glu Gln Thr Met Val
        355                 360                 365

Gln Asp Ile Leu Leu Met Lys Gln Asn Asn Phe Asn Ala Val Arg Cys
    370                 375                 380

Ser His Tyr Pro Asn His Pro Leu Trp Tyr Thr Leu Cys Asp Arg Tyr
385                 390                 395                 400

Gly Leu Tyr Val Val Asp Glu Ala Asn Ile Glu Thr His Gly Met Val
                405                 410                 415

Pro Met Asn Arg Leu Thr Asp Asp Pro Arg Trp Leu Pro Ala Met Ser
            420                 425                 430

Glu Arg Val Thr Arg Met Val Gln Arg Asp Arg Asn His Pro Ser Val
        435                 440                 445

Ile Ile Trp Ser Leu Gly Asn Glu Ser Gly His Gly Ala Asn His Asp
    450                 455                 460

Ala Leu Tyr Arg Trp Ile Lys Ser Val Asp Pro Ser Arg Pro Val Gln
465                 470                 475                 480

Tyr Glu Gly Gly Gly Ala Asp Thr Thr Ala Thr Asp Ile Ile Cys Pro
                485                 490                 495

Met Tyr Ala Arg Val Asp Glu Asp Gln Pro Phe Pro Ala Val Pro Lys
            500                 505                 510

Trp Ser Ile Lys Lys Trp Leu Ser Leu Pro Gly Glu Thr Arg Pro Leu
        515                 520                 525

Ile Leu Cys Glu Tyr Ala His Ala Met Gly Asn Ser Leu Gly Gly Phe
    530                 535                 540

Ala Lys Tyr Trp Gln Ala Phe Arg Gln Tyr Pro Arg Leu Gln Gly Gly
545                 550                 555                 560

Phe Val Trp Asp Trp Val Asp Gln Ser Leu Ile Lys Tyr Asp Glu Asn
                565                 570                 575

Gly Asn Pro Trp Ser Ala Tyr Gly Gly Asp Phe Gly Asp Thr Pro Asn
            580                 585                 590

Asp Arg Gln Phe Cys Met Asn Gly Leu Val Phe Ala Asp Arg Thr Pro
        595                 600                 605

His Pro Ala Leu Thr Glu Ala Lys His Gln Gln Gln Phe Phe Gln Phe
    610                 615                 620

Arg Leu Ser Gly Gln Thr Ile Glu Val Thr Ser Glu Tyr Leu Phe Arg
625                 630                 635                 640

His Ser Asp Asn Glu Leu Leu His Trp Met Val Ala Leu Asp Gly Lys
                645                 650                 655

Pro Leu Ala Ser Gly Glu Val Pro Leu Asp Val Ala Pro Gln Gly Lys
            660                 665                 670

Gln Leu Ile Glu Leu Pro Glu Leu Pro Gln Pro Glu Ser Ala Gly Gln
        675                 680                 685

Leu Trp Leu Thr Val Arg Val Val Gln Pro Asn Ala Thr Ala Trp Ser
    690                 695                 700
```

-continued

```
Glu Ala Gly His Ile Ser Ala Trp Gln Gln Trp Arg Leu Ala Glu Asn
705                 710                 715                 720

Leu Ser Val Thr Leu Pro Ala Ala Ser His Ala Ile Pro His Leu Thr
                725                 730                 735

Thr Ser Glu Met Asp Phe Cys Ile Glu Leu Gly Asn Lys Arg Trp Gln
            740                 745                 750

Phe Asn Arg Gln Ser Gly Phe Leu Ser Gln Met Trp Ile Gly Asp Lys
        755                 760                 765

Lys Gln Leu Leu Thr Pro Leu Arg Asp Gln Phe Thr Arg Ala Pro Leu
    770                 775                 780

Asp Asn Asp Ile Gly Val Ser Glu Ala Thr Arg Ile Asp Pro Asn Ala
785                 790                 795                 800

Trp Val Glu Arg Trp Lys Ala Ala Gly His Tyr Gln Ala Glu Ala Ala
                805                 810                 815

Leu Leu Gln Cys Thr Ala Asp Thr Leu Ala Asp Ala Val Leu Ile Thr
            820                 825                 830

Thr Ala His Ala Trp Gln His Gln Gly Lys Thr Leu Phe Ile Ser Arg
        835                 840                 845

Lys Thr Tyr Arg Ile Asp Gly Ser Gly Gln Met Ala Ile Thr Val Asp
    850                 855                 860

Val Glu Val Ala Ser Asp Thr Pro His Pro Ala Arg Ile Gly Leu Asn
865                 870                 875                 880

Cys Gln Leu Ala Gln Val Ala Glu Arg Val Asn Trp Leu Gly Leu Gly
                885                 890                 895

Pro Gln Glu Asn Tyr Pro Asp Arg Leu Thr Ala Ala Cys Phe Asp Arg
            900                 905                 910

Trp Asp Leu Pro Leu Ser Asp Met Tyr Thr Pro Tyr Val Phe Pro Ser
        915                 920                 925

Glu Asn Gly Leu Arg Cys Gly Thr Arg Glu Leu Asn Tyr Gly Pro His
    930                 935                 940

Gln Trp Arg Gly Asp Phe Gln Phe Asn Ile Ser Arg Tyr Ser Gln Gln
945                 950                 955                 960

Gln Leu Met Glu Thr Ser His Arg His Leu Leu His Ala Glu Glu Gly
                965                 970                 975

Thr Trp Leu Asn Ile Asp Gly Phe His Met Gly Ile Gly Gly Asp Asp
            980                 985                 990

Ser Trp Ser Pro Ser Val Ser Ala  Glu Phe Gln Leu Ser  Ala Gly Arg
        995                 1000                1005

Tyr His  Tyr Gln Leu Val Trp  Cys Gln Lys
    1010                1015
```

```
<210> SEQ ID NO 11
<211> LENGTH: 66
<212> TYPE: DNA
<213> ORGANISM: Artificial Sequence
<220> FEATURE:
<223> OTHER INFORMATION: CpG-Free constitutive promotor

<400> SEQUENCE: 11

caattaaaca ttggcatagt atatctgcat agtataatac aactcactat aggagggcca     60

ccatgg                                                                66


<210> SEQ ID NO 12
<211> LENGTH: 320
<212> TYPE: DNA
<213> ORGANISM: Artificial Sequence
```

```
<220> FEATURE:
<223> OTHER INFORMATION: CpG-Free replication origin

<400> SEQUENCE: 12

gcaggactga ggcttaatta aaccttaaaa cctttaaaag ccttatatat tctttttttt      60

cttataaaac ttaaaacctt agaggctatt taagttgctg atttatatta attttattgt     120

tcaaacatga gagcttagta catgaaacat gagagcttag tacattagcc atgagagctt     180

agtacattag ccatgagggt ttagttcatt aaacatgaga gcttagtaca ttaaacatga     240

gagcttagta catgaaacat gagagcttag tacatactat caacaggttg aactgctgat     300

cttaattaac ctggagactt                                                 320


<210> SEQ ID NO 13
<211> LENGTH: 273
<212> TYPE: DNA
<213> ORGANISM: Artificial Sequence
<220> FEATURE:
<223> OTHER INFORMATION: CpG-Free replication origin

<400> SEQUENCE: 13

ttaattaacc ttaaaacctt taaaagcctt atatattctt tttttctta taaaacttaa      60

aaccttagag gctatttaag ttgctgattt atattaattt tattgttcaa acatgagagc     120

ttagtacatg aaacatgaga gcttagtaca ttagccatga gagcttagta cattagccat     180

gagggtttag ttcattaaac atgagagctt agtacattaa acatgagagc ttagtacata     240

ctatcaacag gttgaactgc tgatcttaat taa                                  273


<210> SEQ ID NO 14
<211> LENGTH: 3852
<212> TYPE: DNA
<213> ORGANISM: Artificial Sequence
<220> FEATURE:
<223> OTHER INFORMATION: SEQ ID NO:14 = CpG-Free pSh-LacZ plasmid ; SEQ
      ID NO:15= SEQ ID NO:14 CDS from 83 to 454 (SEQ ID NO:2) + SEQ ID
      NO:14 CDS from 483 to 3536 (SEQ ID NO:10)
<220> FEATURE:
<221> NAME/KEY: CDS
<222> LOCATION: (83)..(454)
<223> OTHER INFORMATION:
<220> FEATURE:
<221> NAME/KEY: CDS
<222> LOCATION: (483)..(3536)
<223> OTHER INFORMATION:

<400> SEQUENCE: 14

ttaattaaaa cagtagttga caattaaaca ttggcatagt atatctgcat agtataatac      60

aactcactat aggagggcca cc atg gcc aag ttg acc agt gct gtc cca gtg     112
                         Met Ala Lys Leu Thr Ser Ala Val Pro Val
                         1               5                   10

ctc aca gcc agg gat gtg gct gga gct gtt gag ttc tgg act gac agg      160
Leu Thr Ala Arg Asp Val Ala Gly Ala Val Glu Phe Trp Thr Asp Arg
                15                  20                  25

ttg ggg ttc tcc aga gat ttt gtg gag gat gac ttt gca ggt gtg gtc      208
Leu Gly Phe Ser Arg Asp Phe Val Glu Asp Asp Phe Ala Gly Val Val
            30                  35                  40

aga gat gat gtc acc ctg ttc atc tca gca gtc cag gac cag gtg gtg      256
Arg Asp Asp Val Thr Leu Phe Ile Ser Ala Val Gln Asp Gln Val Val
        45                  50                  55

cct gac aac acc ctg gct tgg gtg tgg gtg aga gga ctg gat gag ctg      304
Pro Asp Asn Thr Leu Ala Trp Val Trp Val Arg Gly Leu Asp Glu Leu
    60                  65                  70
```

-continued

```
tat gct gag tgg agt gag gtg gtc tcc acc aac ttc agg gat gcc agt      352
Tyr Ala Glu Trp Ser Glu Val Val Ser Thr Asn Phe Arg Asp Ala Ser
75                  80                  85                  90

ggc cct gcc atg aca gag att gga gag cag ccc tgg ggg aga gag ttt      400
Gly Pro Ala Met Thr Glu Ile Gly Glu Gln Pro Trp Gly Arg Glu Phe
                95                  100                 105

gcc ctg aga gac cca gca ggc aac tgt gtg cac ttt gtg gca gag gag      448
Ala Leu Arg Asp Pro Ala Gly Asn Cys Val His Phe Val Ala Glu Glu
            110                 115                 120

cag gac tgaggataag aattctgagg agaagctc atg gac cct gtt gtg ctg      500
Gln Asp                                Met Asp Pro Val Val Leu
                                       125                 130

caa agg aga gac tgg gag aac cct gga gtg acc cag ctc aac aga ctg      548
Gln Arg Arg Asp Trp Glu Asn Pro Gly Val Thr Gln Leu Asn Arg Leu
                135                 140                 145

gct gcc cac cct ccc ttt gcc tct tgg agg aac tct gag gaa gcc agg      596
Ala Ala His Pro Pro Phe Ala Ser Trp Arg Asn Ser Glu Glu Ala Arg
            150                 155                 160

aca gac agg ccc agc cag cag ctc agg tct ctc aat gga gag tgg agg      644
Thr Asp Arg Pro Ser Gln Gln Leu Arg Ser Leu Asn Gly Glu Trp Arg
        165                 170                 175

ttt gcc tgg ttc cct gcc cct gaa gct gtg cct gag tct tgg ctg gag      692
Phe Ala Trp Phe Pro Ala Pro Glu Ala Val Pro Glu Ser Trp Leu Glu
    180                 185                 190

tgt gac ctc cca gag gct gac act gtt gtg gtg ccc agc aac tgg cag      740
Cys Asp Leu Pro Glu Ala Asp Thr Val Val Val Pro Ser Asn Trp Gln
195                 200                 205                 210

atg cat ggc tat gat gcc ccc atc tac acc aat gtc acc tac ccc atc      788
Met His Gly Tyr Asp Ala Pro Ile Tyr Thr Asn Val Thr Tyr Pro Ile
                215                 220                 225

act gtg aac ccc cct ttt gtg ccc act gag aac ccc act ggc tgc tac      836
Thr Val Asn Pro Pro Phe Val Pro Thr Glu Asn Pro Thr Gly Cys Tyr
            230                 235                 240

agc ctg acc ttc aat gtt gat gag agc tgg ctg caa gaa ggc cag acc      884
Ser Leu Thr Phe Asn Val Asp Glu Ser Trp Leu Gln Glu Gly Gln Thr
        245                 250                 255

agg atc atc ttt gat gga gtc aac tct gcc ttc cac ctc tgg tgc aat      932
Arg Ile Ile Phe Asp Gly Val Asn Ser Ala Phe His Leu Trp Cys Asn
    260                 265                 270

ggc agg tgg gtt ggc tat ggc caa gac agc agg ctg ccc tct gag ttt      980
Gly Arg Trp Val Gly Tyr Gly Gln Asp Ser Arg Leu Pro Ser Glu Phe
275                 280                 285                 290

gac ctc tct gcc ttc ctc aga gct gga gag aac agg ctg gct gtc atg     1028
Asp Leu Ser Ala Phe Leu Arg Ala Gly Glu Asn Arg Leu Ala Val Met
                295                 300                 305

gtg ctc agg tgg tct gat ggc agc tac ctg gaa gac caa gac atg tgg     1076
Val Leu Arg Trp Ser Asp Gly Ser Tyr Leu Glu Asp Gln Asp Met Trp
            310                 315                 320

agg atg tct ggc atc ttc agg gat gtg agc ctg ctg cac aag ccc acc     1124
Arg Met Ser Gly Ile Phe Arg Asp Val Ser Leu Leu His Lys Pro Thr
        325                 330                 335

acc cag att tct gac ttc cat gtt gcc acc agg ttc aat gat gac ttc     1172
Thr Gln Ile Ser Asp Phe His Val Ala Thr Arg Phe Asn Asp Asp Phe
    340                 345                 350

agc aga gct gtg ctg gag gct gag gtg cag atg tgt gga gaa ctc aga     1220
Ser Arg Ala Val Leu Glu Ala Glu Val Gln Met Cys Gly Glu Leu Arg
355                 360                 365                 370

gac tac ctg aga gtc aca gtg agc ctc tgg caa ggt gag acc cag gtg     1268
Asp Tyr Leu Arg Val Thr Val Ser Leu Trp Gln Gly Glu Thr Gln Val
                375                 380                 385
```

-continued

```
gcc tct ggc aca gcc ccc ttt gga gga gag atc att gat gag aga gga      1316
Ala Ser Gly Thr Ala Pro Phe Gly Gly Glu Ile Ile Asp Glu Arg Gly
            390                 395                 400

ggc tat gct gac aga gtc acc ctg agg ctc aat gtg gag aac ccc aag      1364
Gly Tyr Ala Asp Arg Val Thr Leu Arg Leu Asn Val Glu Asn Pro Lys
        405                 410                 415

ctg tgg tct gct gag atc ccc aac ctc tac agg gct gtt gtg gag ctg      1412
Leu Trp Ser Ala Glu Ile Pro Asn Leu Tyr Arg Ala Val Val Glu Leu
    420                 425                 430

cac act gct gat ggc acc ctg att gaa gct gaa gcc tgt gat gtt gga      1460
His Thr Ala Asp Gly Thr Leu Ile Glu Ala Glu Ala Cys Asp Val Gly
435                 440                 445                 450

ttc aga gaa gtc agg att gag aat ggc ctg ctg ctg ctc aat ggc aag      1508
Phe Arg Glu Val Arg Ile Glu Asn Gly Leu Leu Leu Leu Asn Gly Lys
                455                 460                 465

cct ctg ctc atc agg gga gtc aac agg cat gag cac cac cct ctg cat      1556
Pro Leu Leu Ile Arg Gly Val Asn Arg His Glu His His Pro Leu His
            470                 475                 480

gga caa gtg atg gat gaa cag aca atg gtg caa gat atc ctg cta atg      1604
Gly Gln Val Met Asp Glu Gln Thr Met Val Gln Asp Ile Leu Leu Met
        485                 490                 495

aag cag aac aac ttc aat gct gtc agg tgc tct cac tac ccc aac cac      1652
Lys Gln Asn Asn Phe Asn Ala Val Arg Cys Ser His Tyr Pro Asn His
    500                 505                 510

cct ctc tgg tac acc ctg tgt gac agg tat ggc ctg tat gtt gtt gat      1700
Pro Leu Trp Tyr Thr Leu Cys Asp Arg Tyr Gly Leu Tyr Val Val Asp
515                 520                 525                 530

gaa gcc aac att gag aca cat ggc atg gtg ccc atg aac agg ctc aca      1748
Glu Ala Asn Ile Glu Thr His Gly Met Val Pro Met Asn Arg Leu Thr
                535                 540                 545

gat gac ccc agg tgg ctg cct gcc atg tct gag aga gtg acc agg atg      1796
Asp Asp Pro Arg Trp Leu Pro Ala Met Ser Glu Arg Val Thr Arg Met
            550                 555                 560

gtg cag aga gac agg aac cac ccc tct gtg atc atc tgg tct ctg ggc      1844
Val Gln Arg Asp Arg Asn His Pro Ser Val Ile Ile Trp Ser Leu Gly
        565                 570                 575

aat gag tct gga cat gga gcc aac cat gat gct ctc tac agg tgg atc      1892
Asn Glu Ser Gly His Gly Ala Asn His Asp Ala Leu Tyr Arg Trp Ile
    580                 585                 590

aag tct gtt gac ccc agc aga cct gtg cag tat gaa gga ggt gga gca      1940
Lys Ser Val Asp Pro Ser Arg Pro Val Gln Tyr Glu Gly Gly Gly Ala
595                 600                 605                 610

gac acc aca gcc aca gac atc atc tgc ccc atg tat gcc agg gtt gat      1988
Asp Thr Thr Ala Thr Asp Ile Ile Cys Pro Met Tyr Ala Arg Val Asp
                615                 620                 625

gag gac cag ccc ttc cct gct gtg ccc aag tgg agc atc aag aag tgg      2036
Glu Asp Gln Pro Phe Pro Ala Val Pro Lys Trp Ser Ile Lys Lys Trp
            630                 635                 640

ctc tct ctg cct gga gag acc aga cct ctg atc ctg tgt gaa tat gca      2084
Leu Ser Leu Pro Gly Glu Thr Arg Pro Leu Ile Leu Cys Glu Tyr Ala
        645                 650                 655

cat gca atg ggc aac tct ctg gga ggc ttt gcc aag tac tgg caa gcc      2132
His Ala Met Gly Asn Ser Leu Gly Gly Phe Ala Lys Tyr Trp Gln Ala
    660                 665                 670

ttc aga cag tac ccc agg ctg caa gga gga ttt gtg tgg gac tgg gtg      2180
Phe Arg Gln Tyr Pro Arg Leu Gln Gly Gly Phe Val Trp Asp Trp Val
675                 680                 685                 690

gac caa tct ctc atc aag tat gat gag aat ggc aac ccc tgg tct gcc      2228
Asp Gln Ser Leu Ile Lys Tyr Asp Glu Asn Gly Asn Pro Trp Ser Ala
```

-continued

```
            695                 700                 705

tat gga gga gac ttt ggt gac acc ccc aat gac agg cag ttc tgc atg     2276
Tyr Gly Gly Asp Phe Gly Asp Thr Pro Asn Asp Arg Gln Phe Cys Met
            710                 715                 720

aat ggc ctg gtc ttt gca gac agg acc cct cac cct gcc ctc aca gag     2324
Asn Gly Leu Val Phe Ala Asp Arg Thr Pro His Pro Ala Leu Thr Glu
        725                 730                 735

gcc aag cac cag caa cag ttc ttc cag ttc agg ctg tct gga cag acc     2372
Ala Lys His Gln Gln Gln Phe Phe Gln Phe Arg Leu Ser Gly Gln Thr
    740                 745                 750

att gag gtg aca tct gag tac ctc ttc agg cac tct gac aat gag ctc     2420
Ile Glu Val Thr Ser Glu Tyr Leu Phe Arg His Ser Asp Asn Glu Leu
755                 760                 765                 770

ctg cac tgg atg gtg gcc ctg gat ggc aag cct ctg gct tct ggt gag     2468
Leu His Trp Met Val Ala Leu Asp Gly Lys Pro Leu Ala Ser Gly Glu
            775                 780                 785

gtg cct ctg gat gtg gcc cct caa gga aag cag ctg att gaa ctg cct     2516
Val Pro Leu Asp Val Ala Pro Gln Gly Lys Gln Leu Ile Glu Leu Pro
            790                 795                 800

gag ctg cct cag cca gag tct gct gga caa ctg tgg cta aca gtg agg     2564
Glu Leu Pro Gln Pro Glu Ser Ala Gly Gln Leu Trp Leu Thr Val Arg
        805                 810                 815

gtg gtt cag ccc aat gca aca gct tgg tct gag gca ggc cac atc tct     2612
Val Val Gln Pro Asn Ala Thr Ala Trp Ser Glu Ala Gly His Ile Ser
    820                 825                 830

gca tgg cag cag tgg agg ctg gct gag aac ctc tct gtg acc ctg cct     2660
Ala Trp Gln Gln Trp Arg Leu Ala Glu Asn Leu Ser Val Thr Leu Pro
835                 840                 845                 850

gct gcc tct cat gcc atc cct cac ctg aca aca tct gaa atg gac ttc     2708
Ala Ala Ser His Ala Ile Pro His Leu Thr Thr Ser Glu Met Asp Phe
            855                 860                 865

tgc att gag ctg ggc aac aag aga tgg cag ttc aac agg cag tct ggc     2756
Cys Ile Glu Leu Gly Asn Lys Arg Trp Gln Phe Asn Arg Gln Ser Gly
            870                 875                 880

ttc ctg tct cag atg tgg att gga gac aag aag cag ctc ctc acc cct     2804
Phe Leu Ser Gln Met Trp Ile Gly Asp Lys Lys Gln Leu Leu Thr Pro
        885                 890                 895

ctc agg gac caa ttc acc agg gct cct ctg gac aat gac att gga gtg     2852
Leu Arg Asp Gln Phe Thr Arg Ala Pro Leu Asp Asn Asp Ile Gly Val
    900                 905                 910

tct gag gcc acc agg att gac cca aat gct tgg gtg gag agg tgg aag     2900
Ser Glu Ala Thr Arg Ile Asp Pro Asn Ala Trp Val Glu Arg Trp Lys
915                 920                 925                 930

gct gct gga cac tac cag gct gag gct gcc ctg ctc cag tgc aca gca     2948
Ala Ala Gly His Tyr Gln Ala Glu Ala Ala Leu Leu Gln Cys Thr Ala
            935                 940                 945

gac acc ctg gct gat gct gtt ctg atc acc aca gcc cat gct tgg cag     2996
Asp Thr Leu Ala Asp Ala Val Leu Ile Thr Thr Ala His Ala Trp Gln
            950                 955                 960

cac caa ggc aag acc ctg ttc atc agc aga aag acc tac agg att gat     3044
His Gln Gly Lys Thr Leu Phe Ile Ser Arg Lys Thr Tyr Arg Ile Asp
        965                 970                 975

ggc tct gga cag atg gca atc aca gtg gat gtg gag gtt gcc tct gac     3092
Gly Ser Gly Gln Met Ala Ile Thr Val Asp Val Glu Val Ala Ser Asp
    980                 985                 990

aca cct cac cct gca agg  att ggc ctg aac tgt  caa ctg gca cag      3137
Thr Pro His Pro Ala Arg  Ile Gly Leu Asn Cys  Gln Leu Ala Gln
995                 1000                1005

gtg  gct gag agg gtg aac  tgg ctg ggc tta ggc  cct cag gag aac     3182
```

-continued

```
Val  Ala Glu Arg Val Asn  Trp Leu Gly Leu Gly  Pro Gln Glu Asn
1010                 1015                 1020

tac  cct gac agg ctg aca  gct gcc tgc ttt gac  agg tgg gac ctg      3227
Tyr  Pro Asp Arg Leu Thr  Ala Ala Cys Phe Asp  Arg Trp Asp Leu
1025                 1030                 1035

cct  ctg tct gac atg tac  acc cct tat gtg ttc  cct tct gag aat      3272
Pro  Leu Ser Asp Met Tyr  Thr Pro Tyr Val Phe  Pro Ser Glu Asn
1040                 1045                 1050

ggc  ctg agg tgt ggc acc  agg gag ctg aac tat  ggt cct cac cag      3317
Gly  Leu Arg Cys Gly Thr  Arg Glu Leu Asn Tyr  Gly Pro His Gln
1055                 1060                 1065

tgg  agg gga gac ttc cag  ttc aac atc tcc agg  tac tct cag caa      3362
Trp  Arg Gly Asp Phe Gln  Phe Asn Ile Ser Arg  Tyr Ser Gln Gln
1070                 1075                 1080

cag  ctc atg gaa acc tct  cac agg cac ctg ctc  cat gca gag gag      3407
Gln  Leu Met Glu Thr Ser  His Arg His Leu Leu  His Ala Glu Glu
1085                 1090                 1095

gga  acc tgg ctg aac att  gat ggc ttc cac atg  ggc att gga gga      3452
Gly  Thr Trp Leu Asn Ile  Asp Gly Phe His Met  Gly Ile Gly Gly
1100                 1105                 1110

gat  gac tct tgg tct cct  tct gtg tct gct gag  ttc cag tta tct      3497
Asp  Asp Ser Trp Ser Pro  Ser Val Ser Ala Glu  Phe Gln Leu Ser
1115                 1120                 1125

gct  ggc agg tac cac tat  cag ctg gtg tgg tgc  cag aag taagctagct   3546
Ala  Gly Arg Tyr His Tyr  Gln Leu Val Trp Cys  Gln Lys
1130                 1135                 1140

gagtttcaga aaagggggcc tgagtggccc ctttttttcaa cttaattaac cttaaaacct   3606

ttaaaagcct tatatattct tttttttctt ataaaactta aaaccttaga ggctatttaa   3666

gttgctgatt tatattaatt ttattgttca aacatgagag cttagtacat gaaacatgag   3726

agcttagtac attagccatg agagcttagt acattagcca tgagggttta gttcattaaa   3786

catgagagct tagtacatta aacatgagag cttagtacat actatcaaca ggttgaactg   3846

ctgatc                                                              3852
```

<210> SEQ ID NO 15
<211> LENGTH: 1142
<212> TYPE: PRT
<213> ORGANISM: Artificial Sequence
<220> FEATURE:
<223> OTHER INFORMATION: SEQ ID NO:14 = CpG-Free pSh-LacZ plasmid ; SEQ ID NO:15= SEQ ID NO:14 CDS from 83 to 454 (SEQ ID NO:2) + SEQ ID NO:14 CDS from 483 to 3536 (SEQ ID NO:10)

<400> SEQUENCE: 15

```
Met Ala Lys Leu Thr Ser Ala Val Pro Val Leu Thr Ala Arg Asp Val
1               5                   10                  15

Ala Gly Ala Val Glu Phe Trp Thr Asp Arg Leu Gly Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110
```

-continued

```
Gly Asn Cys Val His Phe Val Ala Glu Glu Gln Asp Met Asp Pro Val
        115                 120                 125

Val Leu Gln Arg Arg Asp Trp Glu Asn Pro Gly Val Thr Gln Leu Asn
    130                 135                 140

Arg Leu Ala Ala His Pro Pro Phe Ala Ser Trp Arg Asn Ser Glu Glu
145                 150                 155                 160

Ala Arg Thr Asp Arg Pro Ser Gln Gln Leu Arg Ser Leu Asn Gly Glu
                165                 170                 175

Trp Arg Phe Ala Trp Phe Pro Ala Pro Glu Ala Val Pro Glu Ser Trp
            180                 185                 190

Leu Glu Cys Asp Leu Pro Glu Ala Asp Thr Val Val Val Pro Ser Asn
        195                 200                 205

Trp Gln Met His Gly Tyr Asp Ala Pro Ile Tyr Thr Asn Val Thr Tyr
    210                 215                 220

Pro Ile Thr Val Asn Pro Pro Phe Val Pro Thr Glu Asn Pro Thr Gly
225                 230                 235                 240

Cys Tyr Ser Leu Thr Phe Asn Val Asp Glu Ser Trp Leu Gln Glu Gly
                245                 250                 255

Gln Thr Arg Ile Ile Phe Asp Gly Val Asn Ser Ala Phe His Leu Trp
            260                 265                 270

Cys Asn Gly Arg Trp Val Gly Tyr Gly Gln Asp Ser Arg Leu Pro Ser
        275                 280                 285

Glu Phe Asp Leu Ser Ala Phe Leu Arg Ala Gly Glu Asn Arg Leu Ala
    290                 295                 300

Val Met Val Leu Arg Trp Ser Asp Gly Ser Tyr Leu Glu Asp Gln Asp
305                 310                 315                 320

Met Trp Arg Met Ser Gly Ile Phe Arg Asp Val Ser Leu Leu His Lys
                325                 330                 335

Pro Thr Thr Gln Ile Ser Asp Phe His Val Ala Thr Arg Phe Asn Asp
            340                 345                 350

Asp Phe Ser Arg Ala Val Leu Glu Ala Glu Val Gln Met Cys Gly Glu
        355                 360                 365

Leu Arg Asp Tyr Leu Arg Val Thr Val Ser Leu Trp Gln Gly Glu Thr
    370                 375                 380

Gln Val Ala Ser Gly Thr Ala Pro Phe Gly Gly Glu Ile Ile Asp Glu
385                 390                 395                 400

Arg Gly Gly Tyr Ala Asp Arg Val Thr Leu Arg Leu Asn Val Glu Asn
                405                 410                 415

Pro Lys Leu Trp Ser Ala Glu Ile Pro Asn Leu Tyr Arg Ala Val Val
            420                 425                 430

Glu Leu His Thr Ala Asp Gly Thr Leu Ile Glu Ala Glu Ala Cys Asp
        435                 440                 445

Val Gly Phe Arg Glu Val Arg Ile Glu Asn Gly Leu Leu Leu Leu Asn
    450                 455                 460

Gly Lys Pro Leu Leu Ile Arg Gly Val Asn Arg His Glu His His Pro
465                 470                 475                 480

Leu His Gly Gln Val Met Asp Glu Gln Thr Met Val Gln Asp Ile Leu
                485                 490                 495

Leu Met Lys Gln Asn Asn Phe Asn Ala Val Arg Cys Ser His Tyr Pro
            500                 505                 510

Asn His Pro Leu Trp Tyr Thr Leu Cys Asp Arg Tyr Gly Leu Tyr Val
        515                 520                 525
```

-continued

```
Val Asp Glu Ala Asn Ile Glu Thr His Gly Met Val Pro Met Asn Arg
    530                 535                 540

Leu Thr Asp Asp Pro Arg Trp Leu Pro Ala Met Ser Glu Arg Val Thr
545                 550                 555                 560

Arg Met Val Gln Arg Asp Arg Asn His Pro Ser Val Ile Ile Trp Ser
                565                 570                 575

Leu Gly Asn Glu Ser Gly His Gly Ala Asn His Asp Ala Leu Tyr Arg
            580                 585                 590

Trp Ile Lys Ser Val Asp Pro Ser Arg Pro Val Gln Tyr Glu Gly Gly
        595                 600                 605

Gly Ala Asp Thr Thr Ala Thr Asp Ile Ile Cys Pro Met Tyr Ala Arg
    610                 615                 620

Val Asp Glu Asp Gln Pro Phe Pro Ala Val Pro Lys Trp Ser Ile Lys
625                 630                 635                 640

Lys Trp Leu Ser Leu Pro Gly Glu Thr Arg Pro Leu Ile Leu Cys Glu
                645                 650                 655

Tyr Ala His Ala Met Gly Asn Ser Leu Gly Gly Phe Ala Lys Tyr Trp
            660                 665                 670

Gln Ala Phe Arg Gln Tyr Pro Arg Leu Gln Gly Gly Phe Val Trp Asp
        675                 680                 685

Trp Val Asp Gln Ser Leu Ile Lys Tyr Asp Glu Asn Gly Asn Pro Trp
    690                 695                 700

Ser Ala Tyr Gly Gly Asp Phe Gly Asp Thr Pro Asn Asp Arg Gln Phe
705                 710                 715                 720

Cys Met Asn Gly Leu Val Phe Ala Asp Arg Thr Pro His Pro Ala Leu
                725                 730                 735

Thr Glu Ala Lys His Gln Gln Gln Phe Phe Gln Phe Arg Leu Ser Gly
            740                 745                 750

Gln Thr Ile Glu Val Thr Ser Glu Tyr Leu Phe Arg His Ser Asp Asn
        755                 760                 765

Glu Leu Leu His Trp Met Val Ala Leu Asp Gly Lys Pro Leu Ala Ser
    770                 775                 780

Gly Glu Val Pro Leu Asp Val Ala Pro Gln Gly Lys Gln Leu Ile Glu
785                 790                 795                 800

Leu Pro Glu Leu Pro Gln Pro Glu Ser Ala Gly Gln Leu Trp Leu Thr
                805                 810                 815

Val Arg Val Val Gln Pro Asn Ala Thr Ala Trp Ser Glu Ala Gly His
            820                 825                 830

Ile Ser Ala Trp Gln Gln Trp Arg Leu Ala Glu Asn Leu Ser Val Thr
        835                 840                 845

Leu Pro Ala Ala Ser His Ala Ile Pro His Leu Thr Thr Ser Glu Met
    850                 855                 860

Asp Phe Cys Ile Glu Leu Gly Asn Lys Arg Trp Gln Phe Asn Arg Gln
865                 870                 875                 880

Ser Gly Phe Leu Ser Gln Met Trp Ile Gly Asp Lys Lys Gln Leu Leu
                885                 890                 895

Thr Pro Leu Arg Asp Gln Phe Thr Arg Ala Pro Leu Asp Asn Asp Ile
            900                 905                 910

Gly Val Ser Glu Ala Thr Arg Ile Asp Pro Asn Ala Trp Val Glu Arg
        915                 920                 925

Trp Lys Ala Ala Gly His Tyr Gln Ala Glu Ala Ala Leu Leu Gln Cys
    930                 935                 940

Thr Ala Asp Thr Leu Ala Asp Ala Val Leu Ile Thr Thr Ala His Ala
```

-continued

```
945                 950                 955                 960

Trp Gln His Gln Gly Lys Thr Leu Phe Ile Ser Arg Lys Thr Tyr Arg
                965                 970                 975

Ile Asp Gly Ser Gly Gln Met Ala Ile Thr Val Asp Val Glu Val Ala
            980                 985                 990

Ser Asp Thr Pro His Pro Ala Arg  Ile Gly Leu Asn Cys  Gln Leu Ala
        995                 1000                 1005

Gln Val  Ala Glu Arg Val Asn  Trp Leu Gly Leu Gly  Pro Gln Glu
    1010                 1015                 1020

Asn Tyr  Pro Asp Arg Leu Thr  Ala Ala Cys Phe Asp  Arg Trp Asp
    1025                 1030                 1035

Leu Pro  Leu Ser Asp Met Tyr  Thr Pro Tyr Val Phe  Pro Ser Glu
    1040                 1045                 1050

Asn Gly  Leu Arg Cys Gly Thr  Arg Glu Leu Asn Tyr  Gly Pro His
    1055                 1060                 1065

Gln Trp  Arg Gly Asp Phe Gln  Phe Asn Ile Ser Arg  Tyr Ser Gln
    1070                 1075                 1080

Gln Gln  Leu Met Glu Thr Ser  His Arg His Leu Leu  His Ala Glu
    1085                 1090                 1095

Glu Gly  Thr Trp Leu Asn Ile  Asp Gly Phe His Met  Gly Ile Gly
    1100                 1105                 1110

Gly Asp  Asp Ser Trp Ser Pro  Ser Val Ser Ala Glu  Phe Gln Leu
    1115                 1120                 1125

Ser Ala  Gly Arg Tyr His Tyr  Gln Leu Val Trp Cys  Gln Lys
    1130                 1135                 1140
```

<210> SEQ ID NO 16
<211> LENGTH: 40
<212> TYPE: DNA
<213> ORGANISM: Artificial Sequence
<220> FEATURE:
<223> OTHER INFORMATION: assembling oligo for CpG-Free Sh ble

<400> SEQUENCE: 16
aactcagctg aggaggcaga ccatggccaa gttgaccagt 40

<210> SEQ ID NO 17
<211> LENGTH: 40
<212> TYPE: DNA
<213> ORGANISM: Artificial Sequence
<220> FEATURE:
<223> OTHER INFORMATION: assembling oligo for CpG-Free Sh ble

<400> SEQUENCE: 17
gctgtcccag tgctcacagc cagggatgtg gctggagctg 40

<210> SEQ ID NO 18
<211> LENGTH: 40
<212> TYPE: DNA
<213> ORGANISM: Artificial Sequence
<220> FEATURE:
<223> OTHER INFORMATION: assembling oligo for CpG-Free Sh ble

<400> SEQUENCE: 18
ttgagttctg gactgacagg ttggggttct ccagagattt 40

<210> SEQ ID NO 19
<211> LENGTH: 40
<212> TYPE: DNA
<213> ORGANISM: Artificial Sequence
<220> FEATURE:
<223> OTHER INFORMATION: assembling oligo for CpG-Free Sh ble

<400> SEQUENCE: 19
tgtggaggat gactttgcag gtgtggtcag agatgatgtc 40

<210> SEQ ID NO 20
<211> LENGTH: 40
<212> TYPE: DNA
<213> ORGANISM: Artificial Sequence
<220> FEATURE:
<223> OTHER INFORMATION: assembling oligo for CpG-Free Sh ble

<400> SEQUENCE: 20
accctgttca tctcagcagt ccaggaccag gtggtgcctg 40

<210> SEQ ID NO 21
<211> LENGTH: 40
<212> TYPE: DNA
<213> ORGANISM: Artificial Sequence
<220> FEATURE:
<223> OTHER INFORMATION: assembling oligo for CpG-Free Sh ble

<400> SEQUENCE: 21
acaacaccct ggcttgggtg tgggtgagag gactggatga 40

<210> SEQ ID NO 22
<211> LENGTH: 40
<212> TYPE: DNA
<213> ORGANISM: Artificial Sequence
<220> FEATURE:
<223> OTHER INFORMATION: assembling oligo for CpG-Free Sh ble

<400> SEQUENCE: 22
gctgtatgct gagtggagtg aggtggtctc caccaacttc 40

<210> SEQ ID NO 23
<211> LENGTH: 40
<212> TYPE: DNA
<213> ORGANISM: Artificial Sequence
<220> FEATURE:
<223> OTHER INFORMATION: assembling oligo for CpG-Free Sh ble

<400> SEQUENCE: 23
agggatgcca gtggccctgc catgacagag attggagagc 40

<210> SEQ ID NO 24
<211> LENGTH: 40
<212> TYPE: DNA
<213> ORGANISM: Artificial Sequence
<220> FEATURE:
<223> OTHER INFORMATION: assembling oligo for CpG-Free Sh ble

<400> SEQUENCE: 24
agccctgggg gagagagttt gccctgagag acccagcagg 40

<210> SEQ ID NO 25
<211> LENGTH: 40
<212> TYPE: DNA
<213> ORGANISM: Artificial Sequence
<220> FEATURE:
<223> OTHER INFORMATION: assembling oligo for CpG-Free Sh ble

<400> SEQUENCE: 25
caactgtgtg cactttgtgg cagaggagca ggactgagga 40

<210> SEQ ID NO 26
<211> LENGTH: 21
<212> TYPE: DNA
<213> ORGANISM: Artificial Sequence
<220> FEATURE:
<223> OTHER INFORMATION: assembling oligo for CpG-Free Sh ble

<400> SEQUENCE: 26
taagaattca gctagctcga c 21

<210> SEQ ID NO 27
<211> LENGTH: 41
<212> TYPE: DNA
<213> ORGANISM: Artificial Sequence
<220> FEATURE:
<223> OTHER INFORMATION: assembling oligo for CpG-Free Sh ble

<400> SEQUENCE: 27
gtcgagctag ctgaattctt atcctcagtc ctgctcctct g 41

<210> SEQ ID NO 28
<211> LENGTH: 40
<212> TYPE: DNA
<213> ORGANISM: Artificial Sequence
<220> FEATURE:
<223> OTHER INFORMATION: assembling oligo for CpG-Free Sh ble

<400> SEQUENCE: 28
ccacaaagtg cacacagttg cctgctgggt ctctcagggc 40

<210> SEQ ID NO 29
<211> LENGTH: 40
<212> TYPE: DNA
<213> ORGANISM: Artificial Sequence
<220> FEATURE:
<223> OTHER INFORMATION: assembling oligo for CpG-Free Sh ble

<400> SEQUENCE: 29
aaactctctc ccccagggct gctctccaat ctctgtcatg 40

<210> SEQ ID NO 30
<211> LENGTH: 40
<212> TYPE: DNA
<213> ORGANISM: Artificial Sequence
<220> FEATURE:
<223> OTHER INFORMATION: assembling oligo for CpG-Free Sh ble

<400> SEQUENCE: 30
gcagggccac tggcatccct gaagttggtg gagaccacct 40

<210> SEQ ID NO 31
<211> LENGTH: 40
<212> TYPE: DNA
<213> ORGANISM: Artificial Sequence
<220> FEATURE:
<223> OTHER INFORMATION: assembling oligo for CpG-Free Sh ble

<400> SEQUENCE: 31
cactccactc agcatacagc tcatccagtc ctctcaccca 40

<210> SEQ ID NO 32
<211> LENGTH: 40
<212> TYPE: DNA
<213> ORGANISM: Artificial Sequence
<220> FEATURE:
<223> OTHER INFORMATION: assembling oligo for CpG-Free Sh ble -continued

<400> SEQUENCE: 32
cacccaagcc agggtgttgt caggcaccac ctggtcctgg 40

<210> SEQ ID NO 33
<211> LENGTH: 40
<212> TYPE: DNA
<213> ORGANISM: Artificial Sequence
<220> FEATURE:
<223> OTHER INFORMATION: assembling oligo for CpG-Free Sh ble

<400> SEQUENCE: 33
actgctgaga tgaacagggt gacatcatct ctgaccacac 40

<210> SEQ ID NO 34
<211> LENGTH: 40
<212> TYPE: DNA
<213> ORGANISM: Artificial Sequence
<220> FEATURE:
<223> OTHER INFORMATION: assembling oligo for CpG-Free Sh ble

<400> SEQUENCE: 34
ctgcaaagtc atcctccaca aaatctctgg agaaccccaa 40

<210> SEQ ID NO 35
<211> LENGTH: 40
<212> TYPE: DNA
<213> ORGANISM: Artificial Sequence
<220> FEATURE:
<223> OTHER INFORMATION: assembling oligo for CpG-Free Sh ble

<400> SEQUENCE: 35
cctgtcagtc cagaactcaa cagctccagc cacatccctg 40

<210> SEQ ID NO 36
<211> LENGTH: 40
<212> TYPE: DNA
<213> ORGANISM: Artificial Sequence
<220> FEATURE:
<223> OTHER INFORMATION: assembling oligo for CpG-Free Sh ble

<400> SEQUENCE: 36
gctgtgagca ctgggacagc actggtcaac ttggccatgg 40

<210> SEQ ID NO 37
<211> LENGTH: 20
<212> TYPE: DNA
<213> ORGANISM: Artificial Sequence
<220> FEATURE:
<223> OTHER INFORMATION: assembling oligo for CpG-Free Sh ble

<400> SEQUENCE: 37
tctgcctcct cagctgagtt 20

<210> SEQ ID NO 38
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 38
tgagatcacc ggttcagctg aggaggcaca tcatgaagaa acctgaactg acagcaactt 60

<210> SEQ ID NO 39

<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 39
ctgttgagaa gtttctcatt gaaaaatttg attctgtttc tgatctcatg cagctgtctg 60

<210> SEQ ID NO 40
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 40
aaggtgaaga aagcagagcc ttttcttttg atgttggagg aagaggttat gttctgaggg 60

<210> SEQ ID NO 41
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 41
tcaattcttg tgctgatggt ttttacaaag acagatatgt ttacagacac tttgcctctg 60

<210> SEQ ID NO 42
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 42
ctgctctgcc aattccagaa gttctggaca ttggagaatt ttctgaatct ctcacctact 60

<210> SEQ ID NO 43
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 43
gcatcagcag aagagcacaa ggagtcactc tccaggatct ccctgaaact gagctgccag 60

<210> SEQ ID NO 44
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 44
ctgttctgca acctgttgct gaagcaatgg atgccattgc agcagctgat ctgagccaaa 60

<210> SEQ ID NO 45
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 45
cctctggatt tggtcctttt ggtccccaag gcattggtca gtacaccact tggagggatt 60

<210> SEQ ID NO 46
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 46
tcatttgtgc cattgctgat cctcatgtct atcactggca gactgtgatg gatgacacag 60

<210> SEQ ID NO 47
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 47
tttctgcttc tgttgctcag gcactggatg aactcatgct gtgggcagaa gattgtcctg 60

<210> SEQ ID NO 48
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 48
aagtcagaca cctggtccat gctgattttg gaagcaacaa tgttctgaca gacaatggca 60

<210> SEQ ID NO 49
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 49
gaatcactgc agtcattgac tggtctgaag ccatgtttgg agattctcaa tatgaggttg 60

<210> SEQ ID NO 50
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 50
ccaacatttt tttttggaga ccttggctgg cttgcatgga acaacaaaca agatattttg 60

<210> SEQ ID NO 51
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 51
aaagaagaca cccagaactg gctggttccc ccagactgag agcctacatg ctcagaattg 60

<210> SEQ ID NO 52
<211> LENGTH: 60
<212> TYPE: DNA

<213> ORGANISM: Artificial Sequence
<220> FEATURE:
<223> OTHER INFORMATION: assembling oligo for CpG-Free Hph

<400> SEQUENCE: 52
gcctggacca actgtatcaa tctctggttg atggaaactt tgatgatgct gcttgggcac 60

<210> SEQ ID NO 53
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 53
aaggaagatg tgatgccatt gtgaggtctg gtgctggaac tgttggaaga actcaaattg 60

<210> SEQ ID NO 54
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 54
caagaaggtc tgctgctgtt tggactgatg gatgtgttga agttctggct gactctggaa 60

<210> SEQ ID NO 55
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 55
acaggagacc ctccacaaga cccagagcca aggaatgaat attagctagc ggatcctgag 60

<210> SEQ ID NO 56
<211> LENGTH: 30
<212> TYPE: DNA
<213> ORGANISM: Artificial Sequence
<220> FEATURE:
<223> OTHER INFORMATION: assembling oligo for CpG-Free Hph

<400> SEQUENCE: 56
ctcaggatcc gctagctaat attcattcct 30

<210> SEQ ID NO 57
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 57
tggctctggg tcttgtggag ggtctcctgt ttccagagtc agccagaact tcaacacatc 60

<210> SEQ ID NO 58
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 58
catcagtcca aacagcagca gaccttcttg caatttgagt tcttccaaca gttccagcac 60

<210> SEQ ID NO 59
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 59
cagacctcac aatggcatca catcttcctt gtgcccaagc agcatcatca aagtttccat 60

<210> SEQ ID NO 60
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 60
caaccagaga ttgatacagt tggtccaggc caattctgag catgtaggct ctcagtctgg 60

<210> SEQ ID NO 61
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 61
gggaaccagc cagttctggg tgtcttcttt caaaatatct tgtttgttgt tccatgcaag 60

<210> SEQ ID NO 62
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 62
ccagccaagg tctccaaaaa aaaatgttgg caacctcata ttgagaatct ccaaacatgg 60

<210> SEQ ID NO 63
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 63
cttcagacca gtcaatgact gcagtgattc tgccattgtc tgtcagaaca ttgttgcttc 60

<210> SEQ ID NO 64
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 64
caaaatcagc atggaccagg tgtctgactt caggacaatc ttctgcccac agcatgagtt 60

<210> SEQ ID NO 65
<211> LENGTH: 60
<212> TYPE: DNA
<213> ORGANISM: Artificial Sequence
<220> FEATURE:

-continued

<223> OTHER INFORMATION: assembling oligo for CpG-Free Hph

<400> SEQUENCE: 65
catccagtgc ctgagcaaca gaagcagaaa ctgtgtcatc catcacagtc tgccagtgat 60

<210> SEQ ID NO 66
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 66
agacatgagg atcagcaatg gcacaaatga aatccctcca agtggtgtac tgaccaatgc 60

<210> SEQ ID NO 67
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 67
cttggggacc aaaaggacca aatccagagg tttggctcag atcagctgct gcaatggcat 60

<210> SEQ ID NO 68
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 68
ccattgcttc agcaacaggt tgcagaacag ctggcagctc agtttcaggg agatcctgga 60

<210> SEQ ID NO 69
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 69
gagtgactcc ttgtgctctt ctgctgatgc agtaggtgag agattcagaa aattctccaa 60

<210> SEQ ID NO 70
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 70
tgtccagaac ttctggaatt ggcagagcag cagaggcaaa gtgtctgtaa acatatctgt 60

<210> SEQ ID NO 71
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 71
ctttgtaaaa accatcagca caagaattga ccctcagaac ataacctctt cctccaacat 60

-continued

<210> SEQ ID NO 72
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 72
caaaagaaaa ggctctgctt tcttcacctt cagacagctg catgagatca gaaacagaat 60

<210> SEQ ID NO 73
<211> LENGTH: 60
<212> TYPE: DNA
<213> ORGANISM: Artificial Sequence
<220> FEATURE:
<223> OTHER INFORMATION: assembling oligo for CpG-Free Hph

<400> SEQUENCE: 73
caaatttttc aatgagaaac ttctcaacag aagttgctgt cagttcaggt ttcttcatga 60

<210> SEQ ID NO 74
<211> LENGTH: 30
<212> TYPE: DNA
<213> ORGANISM: Artificial Sequence
<220> FEATURE:
<223> OTHER INFORMATION: assembling oligo for CpG-Free Hph

<400> SEQUENCE: 74
tgtgcctcct cagctgaacc ggtgatctca 30

<210> SEQ ID NO 75
<211> LENGTH: 40
<212> TYPE: DNA
<213> ORGANISM: Artificial Sequence
<220> FEATURE:
<223> OTHER INFORMATION: assembling oligo for CpG-Free Bsr

<400> SEQUENCE: 75
aggaggcaca tcatgaagac cttcaacatc tctcagcagg 40

<210> SEQ ID NO 76
<211> LENGTH: 40
<212> TYPE: DNA
<213> ORGANISM: Artificial Sequence
<220> FEATURE:
<223> OTHER INFORMATION: assembling oligo for CpG-Free Bsr

<400> SEQUENCE: 76
atctggagct ggtggaggtc gccactgaga agatcaccat 40

<210> SEQ ID NO 77
<211> LENGTH: 40
<212> TYPE: DNA
<213> ORGANISM: Artificial Sequence
<220> FEATURE:
<223> OTHER INFORMATION: assembling oligo for CpG-Free Bsr

<400> SEQUENCE: 77
gctctatgag gacaacaagc accatgtcgg ggcggccatc 40

<210> SEQ ID NO 78
<211> LENGTH: 40
<212> TYPE: DNA
<213> ORGANISM: Artificial Sequence
<220> FEATURE:
<223> OTHER INFORMATION: assembling oligo for CpG-Free Bsr

<400> SEQUENCE: 78
aggaccaaga ctggggagat catctctgct gtccacattg 40

<210> SEQ ID NO 79
<211> LENGTH: 40
<212> TYPE: DNA
<213> ORGANISM: Artificial Sequence
<220> FEATURE:
<223> OTHER INFORMATION: assembling oligo for CpG-Free Bsr

<400> SEQUENCE: 79
aggcctacat tggcagggtc actgtctgtg ctgaagccat 40

<210> SEQ ID NO 80
<211> LENGTH: 40
<212> TYPE: DNA
<213> ORGANISM: Artificial Sequence
<220> FEATURE:
<223> OTHER INFORMATION: assembling oligo for CpG-Free Bsr

<400> SEQUENCE: 80
tgccattggg tctgctgtga gcaacgggca gaaggacttt 40

<210> SEQ ID NO 81
<211> LENGTH: 40
<212> TYPE: DNA
<213> ORGANISM: Artificial Sequence
<220> FEATURE:
<223> OTHER INFORMATION: assembling oligo for CpG-Free Bsr

<400> SEQUENCE: 81
gacaccattg tggctgtcag gcacccctac tctgatgagg 40

<210> SEQ ID NO 82
<211> LENGTH: 40
<212> TYPE: DNA
<213> ORGANISM: Artificial Sequence
<220> FEATURE:
<223> OTHER INFORMATION: assembling oligo for CpG-Free Bsr

<400> SEQUENCE: 82
tggacagatc catcagggtg gtcagcccct gtggcatgtg 40

<210> SEQ ID NO 83
<211> LENGTH: 40
<212> TYPE: DNA
<213> ORGANISM: Artificial Sequence
<220> FEATURE:
<223> OTHER INFORMATION: assembling oligo for CpG-Free Bsr

<400> SEQUENCE: 83
cagagagctc atctctgact atgctcctga ctgctttgtg 40

<210> SEQ ID NO 84
<211> LENGTH: 40
<212> TYPE: DNA
<213> ORGANISM: Artificial Sequence
<220> FEATURE:
<223> OTHER INFORMATION: assembling oligo for CpG-Free Bsr

<400> SEQUENCE: 84
ctcattgaga tgaatggcaa gctggtcaaa accaccattg 40

<210> SEQ ID NO 85
<211> LENGTH: 40

<212> TYPE: DNA
<213> ORGANISM: Artificial Sequence
<220> FEATURE:
<223> OTHER INFORMATION: assembling oligo for CpG-Free Bsr

<400> SEQUENCE: 85
aggaactcat ccccctcaag tacaccagga actaaacctg 40

<210> SEQ ID NO 86
<211> LENGTH: 21
<212> TYPE: DNA
<213> ORGANISM: Artificial Sequence
<220> FEATURE:
<223> OTHER INFORMATION: assembling oligo for CpG-Free Bsr

<400> SEQUENCE: 86
aattcagcta gctcgacatg a 21

<210> SEQ ID NO 87
<211> LENGTH: 41
<212> TYPE: DNA
<213> ORGANISM: Artificial Sequence
<220> FEATURE:
<223> OTHER INFORMATION: assembling oligo for CpG-Free Bsr

<400> SEQUENCE: 87
tcatgtcgag ctagctgaat tcaggtttag ttcctggtgt a 41

<210> SEQ ID NO 88
<211> LENGTH: 40
<212> TYPE: DNA
<213> ORGANISM: Artificial Sequence
<220> FEATURE:
<223> OTHER INFORMATION: assembling oligo for CpG-Free Bsr

<400> SEQUENCE: 88
cttgaggggg atgagttcct caatggtggt tttgaccagc 40

<210> SEQ ID NO 89
<211> LENGTH: 40
<212> TYPE: DNA
<213> ORGANISM: Artificial Sequence
<220> FEATURE:
<223> OTHER INFORMATION: assembling oligo for CpG-Free Bsr

<400> SEQUENCE: 89
ttgccattca tctcaatgag cacaaagcag tcaggagcat 40

<210> SEQ ID NO 90
<211> LENGTH: 40
<212> TYPE: DNA
<213> ORGANISM: Artificial Sequence
<220> FEATURE:
<223> OTHER INFORMATION: assembling oligo for CpG-Free Bsr

<400> SEQUENCE: 90
agtcagagat gagctctctg cacatgccac aggggctgac 40

<210> SEQ ID NO 91
<211> LENGTH: 40
<212> TYPE: DNA
<213> ORGANISM: Artificial Sequence
<220> FEATURE:
<223> OTHER INFORMATION: assembling oligo for CpG-Free Bsr

<400> SEQUENCE: 91

-continued

```
caccctgatg gatctgtcca cctcatcaga gtaggggtgc                            40


<210> SEQ ID NO 92
<211> LENGTH: 40
<212> TYPE: DNA
<213> ORGANISM: Artificial Sequence
<220> FEATURE:
<223> OTHER INFORMATION: assembling oligo for CpG-Free Bsr

<400> SEQUENCE: 92

ctgacagcca caatggtgtc aaagtccttc tgcccgttgc                            40


<210> SEQ ID NO 93
<211> LENGTH: 40
<212> TYPE: DNA
<213> ORGANISM: Artificial Sequence
<220> FEATURE:
<223> OTHER INFORMATION: assembling oligo for CpG-Free Bsr

<400> SEQUENCE: 93

tcacagcaga cccaatggca atggcttcag cacagacagt                            40


<210> SEQ ID NO 94
<211> LENGTH: 40
<212> TYPE: DNA
<213> ORGANISM: Artificial Sequence
<220> FEATURE:
<223> OTHER INFORMATION: assembling oligo for CpG-Free Bsr

<400> SEQUENCE: 94

gaccctgcca atgtaggcct caatgtggac agcagagatg                            40


<210> SEQ ID NO 95
<211> LENGTH: 40
<212> TYPE: DNA
<213> ORGANISM: Artificial Sequence
<220> FEATURE:
<223> OTHER INFORMATION: assembling oligo for CpG-Free Bsr

<400> SEQUENCE: 95

atctccccag tcttggtcct gatggccgcc ccgacatggt                            40


<210> SEQ ID NO 96
<211> LENGTH: 40
<212> TYPE: DNA
<213> ORGANISM: Artificial Sequence
<220> FEATURE:
<223> OTHER INFORMATION: assembling oligo for CpG-Free Bsr

<400> SEQUENCE: 96

gcttgttgtc ctcatagagc atggtgatct tctcagtggc                            40


<210> SEQ ID NO 97
<211> LENGTH: 40
<212> TYPE: DNA
<213> ORGANISM: Artificial Sequence
<220> FEATURE:
<223> OTHER INFORMATION: assembling oligo for CpG-Free Bsr

<400> SEQUENCE: 97

gacctccacc agctccagat cctgctgaga gatgttgaag                            40


<210> SEQ ID NO 98
<211> LENGTH: 20
<212> TYPE: DNA
<213> ORGANISM: Artificial Sequence
```

<220> FEATURE:
<223> OTHER INFORMATION: assembling oligo for CpG-Free Bsr

<400> SEQUENCE: 98
gtcttcatga tgtgcctcct 20

<210> SEQ ID NO 99
<211> LENGTH: 60
<212> TYPE: DNA
<213> ORGANISM: Artificial Sequence
<220> FEATURE:
<223> OTHER INFORMATION: assembling oligo for CpG-Free Pac

<400> SEQUENCE: 99
ctcactatag gaggaccatc atgactgagt acaaacccac agtgaggctg gcaaccagag 60

<210> SEQ ID NO 100
<211> LENGTH: 60
<212> TYPE: DNA
<213> ORGANISM: Artificial Sequence
<220> FEATURE:
<223> OTHER INFORMATION: assembling oligo for CpG-Free Pac

<400> SEQUENCE: 100
atgatgttcc aagagctgtg agaacactgg ctgctgcttt tgcagactac cctgcaacaa 60

<210> SEQ ID NO 101
<211> LENGTH: 60
<212> TYPE: DNA
<213> ORGANISM: Artificial Sequence
<220> FEATURE:
<223> OTHER INFORMATION: assembling oligo for CpG-Free Pac

<400> SEQUENCE: 101
ggcacacagt tgaccctgac aggcacattg agagggtgac agaactgcaa gaactcttcc 60

<210> SEQ ID NO 102
<211> LENGTH: 60
<212> TYPE: DNA
<213> ORGANISM: Artificial Sequence
<220> FEATURE:
<223> OTHER INFORMATION: assembling oligo for CpG-Free Pac

<400> SEQUENCE: 102
tcaccagagt gggactggac attggaaaag tttgggttgc agatgatgga gctgctgttg 60

<210> SEQ ID NO 103
<211> LENGTH: 60
<212> TYPE: DNA
<213> ORGANISM: Artificial Sequence
<220> FEATURE:
<223> OTHER INFORMATION: assembling oligo for CpG-Free Pac

<400> SEQUENCE: 103
cagtttggac aacacctgag tctgttgaag ctggtgctgt ttttgctgaa attggaccaa 60

<210> SEQ ID NO 104
<211> LENGTH: 60
<212> TYPE: DNA
<213> ORGANISM: Artificial Sequence
<220> FEATURE:
<223> OTHER INFORMATION: assembling oligo for CpG-Free Pac

<400> SEQUENCE: 104
gaatggctga gctctctgga agcaggctgg cagcacaaca acaaatggaa ggtctgctgg 60

<210> SEQ ID NO 105
<211> LENGTH: 60
<212> TYPE: DNA
<213> ORGANISM: Artificial Sequence
<220> FEATURE:
<223> OTHER INFORMATION: assembling oligo for CpG-Free Pac

<400> SEQUENCE: 105
caccacacag gccaaaagag ccagcttggt ttctggcaac tgttggagtg agccctgacc 60

<210> SEQ ID NO 106
<211> LENGTH: 60
<212> TYPE: DNA
<213> ORGANISM: Artificial Sequence
<220> FEATURE:
<223> OTHER INFORMATION: assembling oligo for CpG-Free Pac

<400> SEQUENCE: 106
accagggaaa gggtctggga tctgctgttg ttctgcctgg agttgaagct gctgaaaggg 60

<210> SEQ ID NO 107
<211> LENGTH: 60
<212> TYPE: DNA
<213> ORGANISM: Artificial Sequence
<220> FEATURE:
<223> OTHER INFORMATION: assembling oligo for CpG-Free Pac

<400> SEQUENCE: 107
ctggagttcc tgcctttctg gaaacttctg ctcccagaaa cctgcctttt tatgaaagac 60

<210> SEQ ID NO 108
<211> LENGTH: 60
<212> TYPE: DNA
<213> ORGANISM: Artificial Sequence
<220> FEATURE:
<223> OTHER INFORMATION: assembling oligo for CpG-Free Pac

<400> SEQUENCE: 108
tgggattcac tgtgacagct gatgttgagg ttccagaagg cccaagaact tggtgcatga 60

<210> SEQ ID NO 109
<211> LENGTH: 60
<212> TYPE: DNA
<213> ORGANISM: Artificial Sequence
<220> FEATURE:
<223> OTHER INFORMATION: assembling oligo for CpG-Free Pac

<400> SEQUENCE: 109
caaggaagcc tggagcttaa acctgagcta gctcgacatg ataagataca ttgatgagtt 60

<210> SEQ ID NO 110
<211> LENGTH: 30
<212> TYPE: DNA
<213> ORGANISM: Artificial Sequence
<220> FEATURE:
<223> OTHER INFORMATION: assembling oligo for CpG-Free Pac

<400> SEQUENCE: 110
aactcatcaa tgtatcttat catgtcgagc 30

<210> SEQ ID NO 111
<211> LENGTH: 60
<212> TYPE: DNA
<213> ORGANISM: Artificial Sequence
<220> FEATURE:
<223> OTHER INFORMATION: assembling oligo for CpG-Free Pac

<400> SEQUENCE: 111
tagctcaggt ttaagctcca ggcttccttg tcatgcacca agttcttggg ccttctggaa 60

<210> SEQ ID NO 112
<211> LENGTH: 60
<212> TYPE: DNA
<213> ORGANISM: Artificial Sequence
<220> FEATURE:
<223> OTHER INFORMATION: assembling oligo for CpG-Free Pac

<400> SEQUENCE: 112
cctcaacatc agctgtcaca gtgaatccca gtctttcata aaaaggcagg tttctgggag 60

<210> SEQ ID NO 113
<211> LENGTH: 60
<212> TYPE: DNA
<213> ORGANISM: Artificial Sequence
<220> FEATURE:
<223> OTHER INFORMATION: assembling oligo for CpG-Free Pac

<400> SEQUENCE: 113
cagaagtttc cagaaaggca ggaactccag ccctttcagc agcttcaact ccaggcagaa 60

<210> SEQ ID NO 114
<211> LENGTH: 60
<212> TYPE: DNA
<213> ORGANISM: Artificial Sequence
<220> FEATURE:
<223> OTHER INFORMATION: assembling oligo for CpG-Free Pac

<400> SEQUENCE: 114
caacagcaga tcccagaccc tttccctggt ggtcagggct cactccaaca gttgccagaa 60

<210> SEQ ID NO 115
<211> LENGTH: 60
<212> TYPE: DNA
<213> ORGANISM: Artificial Sequence
<220> FEATURE:
<223> OTHER INFORMATION: assembling oligo for CpG-Free Pac

<400> SEQUENCE: 115
accaagctgg ctcttttggc ctgtgtggtg ccagcagacc ttccatttgt tgttgtgctg 60

<210> SEQ ID NO 116
<211> LENGTH: 60
<212> TYPE: DNA
<213> ORGANISM: Artificial Sequence
<220> FEATURE:
<223> OTHER INFORMATION: assembling oligo for CpG-Free Pac

<400> SEQUENCE: 116
ccagcctgct tccagagagc tcagccattc ttggtccaat ttcagcaaaa acagcaccag 60

<210> SEQ ID NO 117
<211> LENGTH: 60
<212> TYPE: DNA
<213> ORGANISM: Artificial Sequence
<220> FEATURE:
<223> OTHER INFORMATION: assembling oligo for CpG-Free Pac

<400> SEQUENCE: 117
cttcaacaga ctcaggtgtt gtccaaactg caacagcagc tccatcatct gcaacccaaa 60

<210> SEQ ID NO 118

<211> LENGTH: 60
<212> TYPE: DNA
<213> ORGANISM: Artificial Sequence
<220> FEATURE:
<223> OTHER INFORMATION: assembling oligo for CpG-Free Pac

<400> SEQUENCE: 118
cttttccaat gtccagtccc actctggtga ggaagagttc ttgcagttct gtcaccctct 60

<210> SEQ ID NO 119
<211> LENGTH: 60
<212> TYPE: DNA
<213> ORGANISM: Artificial Sequence
<220> FEATURE:
<223> OTHER INFORMATION: assembling oligo for CpG-Free Pac

<400> SEQUENCE: 119
caatgtgcct gtcagggtca actgtgtgcc ttgttgcagg gtagtctgca aaagcagcag 60

<210> SEQ ID NO 120
<211> LENGTH: 60
<212> TYPE: DNA
<213> ORGANISM: Artificial Sequence
<220> FEATURE:
<223> OTHER INFORMATION: assembling oligo for CpG-Free Pac

<400> SEQUENCE: 120
ccagtgttct cacagctctt ggaacatcat ctctggttgc cagcctcact gtgggtttgt 60

<210> SEQ ID NO 121
<211> LENGTH: 30
<212> TYPE: DNA
<213> ORGANISM: Artificial Sequence
<220> FEATURE:
<223> OTHER INFORMATION: assembling oligo for CpG-Free Pac

<400> SEQUENCE: 121
actcagtcat gatggtcctc ctatagtgag 30

<210> SEQ ID NO 122
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 122
atcactatag gagggccacc atggaccctg ttgtgctgca 40

<210> SEQ ID NO 123
<211> LENGTH: 20
<212> TYPE: DNA
<213> ORGANISM: Artificial Sequence
<220> FEATURE:
<223> OTHER INFORMATION: assembling oligo for CpG-free LacZ

<400> SEQUENCE: 123
ggtggccctc ctatagtgat 20

<210> SEQ ID NO 124
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 124
aaggagagac tgggagaacc ctggagtgac ccagctcaac 40

<210> SEQ ID NO 125
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 125
ggttctccca gtctctcctt tgcagcacaa cagggtccat 40

<210> SEQ ID NO 126
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 126
agactggctg cccaccctcc ctttgcctct tggaggaact 40

<210> SEQ ID NO 127
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 127
ggagggtggg cagccagtct gttgagctgg gtcactccag 40

<210> SEQ ID NO 128
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 128
ctgaggaagc caggacagac aggcccagcc agcagctcag 40

<210> SEQ ID NO 129
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 129
gtctgtcctg gcttcctcag agttcctcca agaggcaaag 40

<210> SEQ ID NO 130
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 130
gtctctcaat ggagagtgga ggtttgcctg gttccctgcc 40

<210> SEQ ID NO 131
<211> LENGTH: 40
<212> TYPE: DNA

<213> ORGANISM: Artificial Sequence
<220> FEATURE:
<223> OTHER INFORMATION: assembling oligo for CpG-free LacZ

<400> SEQUENCE: 131
tccactctcc attgagagac ctgagctgct ggctgggcct 40

<210> SEQ ID NO 132
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 132
cctgaagctg tgcctgagtc ttggctggag tgtgacctcc 40

<210> SEQ ID NO 133
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 133
gactcaggca cagcttcagg ggcagggaac caggcaaacc 40

<210> SEQ ID NO 134
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 134
cagaggctga cactgttgtg gtgcccagca actggcagat 40

<210> SEQ ID NO 135
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 135
cacaacagtg tcagcctctg ggaggtcaca ctccagccaa 40

<210> SEQ ID NO 136
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 136
gcatggctat gatgccccca tctacaccaa tgtcacctac 40

<210> SEQ ID NO 137
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 137
tgggggcatc atagccatgc atctgccagt tgctgggcac 40

<210> SEQ ID NO 138
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 138
cccatcactg tgaacccccc ttttgtgccc actgagaacc 40

<210> SEQ ID NO 139
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 139
ggggggttca cagtgatggg gtaggtgaca ttggtgtaga 40

<210> SEQ ID NO 140
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 140
ccactggctg ctacagcctg accttcaatg ttgatgagag 40

<210> SEQ ID NO 141
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 141
caggctgtag cagccagtgg ggttctcagt gggcacaaaa 40

<210> SEQ ID NO 142
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 142
ctggctgcaa gaaggccaga ccaggatcat ctttgatgga 40

<210> SEQ ID NO 143
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 143
tctggccttc ttgcagccag ctctcatcaa cattgaaggt 40

<210> SEQ ID NO 144
<211> LENGTH: 40
<212> TYPE: DNA
<213> ORGANISM: Artificial Sequence
<220> FEATURE:

<223> OTHER INFORMATION: assembling oligo for CpG-free LacZ

<400> SEQUENCE: 144
gtcaactctg ccttccacct ctggtgcaat ggcaggtggg 40

<210> SEQ ID NO 145
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 145
aggtggaagg cagagttgac tccatcaaag atgatcctgg 40

<210> SEQ ID NO 146
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 146
ttggctatgg ccaagacagc aggctgccct ctgagtttga 40

<210> SEQ ID NO 147
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 147
gctgtcttgg ccatagccaa cccacctgcc attgcaccag 40

<210> SEQ ID NO 148
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 148
cctctctgcc ttcctcagag ctggagagaa caggctggct 40

<210> SEQ ID NO 149
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 149
ctctgaggaa ggcagagagg tcaaactcag agggcagcct 40

<210> SEQ ID NO 150
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 150
gtcatggtgc tcaggtggtc tgatggcagc tacctggaag 40

<210> SEQ ID NO 151
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 151
gaccacctga gcaccatgac agccagcctg ttctctccag 40

<210> SEQ ID NO 152
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 152
accaagacat gtggaggatg tctggcatct tcagggatgt 40

<210> SEQ ID NO 153
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 153
catcctccac atgtcttggt cttccaggta gctgccatca 40

<210> SEQ ID NO 154
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 154
gagcctgctg cacaagccca ccacccagat ttctgacttc 40

<210> SEQ ID NO 155
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 155
tgggcttgtg cagcaggctc acatccctga agatgccaga 40

<210> SEQ ID NO 156
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 156
catgttgcca ccaggttcaa tgatgacttc agcagagctg 40

<210> SEQ ID NO 157
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 157
ttgaacctgg tggcaacatg gaagtcagaa atctgggtgg 40

<210> SEQ ID NO 158
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 158
tgctggaggc tgaggtgcag atgtgtggag aactcagaga 40

<210> SEQ ID NO 159
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 159
ctgcacctca gcctccagca cagctctgct gaagtcatca 40

<210> SEQ ID NO 160
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 160
ctacctgaga gtcacagtga gcctctggca aggtgagacc 40

<210> SEQ ID NO 161
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 161
tcactgtgac tctcaggtag tctctgagtt ctccacacat 40

<210> SEQ ID NO 162
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 162
caggtggcct ctggcacagc cccctttgga ggagagatca 40

<210> SEQ ID NO 163
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 163
gctgtgccag aggccacctg ggtctcacct tgccagaggc 40

<210> SEQ ID NO 164
<211> LENGTH: 40

<212> TYPE: DNA
<213> ORGANISM: Artificial Sequence
<220> FEATURE:
<223> OTHER INFORMATION: assembling oligo for CpG-free LacZ

<400> SEQUENCE: 164
ttgatgagag aggaggctat gctgacagag tcaccctgag 40

<210> SEQ ID NO 165
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 165
atagcctcct ctctcatcaa tgatctctcc tccaaagggg 40

<210> SEQ ID NO 166
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 166
gctcaatgtg gagaacccca agctgtggtc tgctgagatc 40

<210> SEQ ID NO 167
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 167
tggggttctc cacattgagc ctcagggtga ctctgtcagc 40

<210> SEQ ID NO 168
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 168
cccaacctct acagggctgt tgtggagctg cacactgctg 40

<210> SEQ ID NO 169
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 169
acagccctgt agaggttggg gatctcagca gaccacagct 40

<210> SEQ ID NO 170
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 170
atggcaccct gattgaagct gaagcctgtg atgttggatt 40

<210> SEQ ID NO 171
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 171
agcttcaatc agggtgccat cagcagtgtg cagctccaca 40

<210> SEQ ID NO 172
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 172
cagagaagtc aggattgaga atggcctgct gctgctcaat 40

<210> SEQ ID NO 173
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 173
tctcaatcct gacttctctg aatccaacat cacaggcttc 40

<210> SEQ ID NO 174
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 174
ggcaagcctc tgctcatcag gggagtcaac aggcatgagc 40

<210> SEQ ID NO 175
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 175
ctgatgagca gaggcttgcc attgagcagc agcaggccat 40

<210> SEQ ID NO 176
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 176
accaccctct gcatggacaa gtgatggatg aacagacaat 40

<210> SEQ ID NO 177
<211> LENGTH: 40
<212> TYPE: DNA
<213> ORGANISM: Artificial Sequence -continued
<220> FEATURE:
<223> OTHER INFORMATION: assembling oligo for CpG-free LacZ

<400> SEQUENCE: 177
ttgtccatgc agagggtggt gctcatgcct gttgactccc 40

<210> SEQ ID NO 178
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 178
ggtgcaagat atcctgctga tgaagcagaa ctccgcctac 40

<210> SEQ ID NO 179
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 179
tcagcaggat atcttgcacc attgtctgtt catccatcac 40

<210> SEQ ID NO 180
<211> LENGTH: 20
<212> TYPE: DNA
<213> ORGANISM: Artificial Sequence
<220> FEATURE:
<223> OTHER INFORMATION: assembling oligo for CpG-free LacZ

<400> SEQUENCE: 180
gtaggcggag ttctgcttca 20

<210> SEQ ID NO 181
<211> LENGTH: 20
<212> TYPE: DNA
<213> ORGANISM: Artificial Sequence
<220> FEATURE:
<223> OTHER INFORMATION: assembling oligo for CpG-free LacZ

<400> SEQUENCE: 181
tcattagcag gatatcttgc 20

<210> SEQ ID NO 182
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 182
gcaagatatc ctgctaatga agcagaacaa cttcaatgct 40

<210> SEQ ID NO 183
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 183
gggtagtgag agcacctgac agcattgaag ttgttctgct 40

<210> SEQ ID NO 184
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 184
gtcaggtgct ctcactaccc caaccaccct ctctggtaca 40

<210> SEQ ID NO 185
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 185
gccatacctg tcacacaggg tgtaccagag agggtggttg 40

<210> SEQ ID NO 186
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 186
ccctgtgtga caggtatggc ctgtatgttg ttgatgaagc 40

<210> SEQ ID NO 187
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 187
tgccatgtgt ctcaatgttg gcttcatcaa caacatacag 40

<210> SEQ ID NO 188
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 188
caacattgag acacatggca tggtgcccat gaacaggctc 40

<210> SEQ ID NO 189
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 189
agccacctgg ggtcatctgt gagcctgttc atgggcacca 40

<210> SEQ ID NO 190
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 190
acagatgacc ccaggtggct gcctgccatg tctgagagag 40

<210> SEQ ID NO 191
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 191
tctctgcacc atcctggtca ctctctcaga catggcaggc 40

<210> SEQ ID NO 192
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 192
tgaccaggat ggtgcagaga gacaggaacc acccctctgt 40

<210> SEQ ID NO 193
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 193
tgcccagaga ccagatgatc acagaggggt ggttcctgtc 40

<210> SEQ ID NO 194
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 194
gatcatctgg tctctgggca atgagtctgg acatggagcc 40

<210> SEQ ID NO 195
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 195
ctgtagagag catcatggtt ggctccatgt ccagactcat 40

<210> SEQ ID NO 196
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 196
aaccatgatg ctctctacag gtggatcaag tctgttgacc 40

<210> SEQ ID NO 197

<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 197
atactgcaca ggtctgctgg ggtcaacaga cttgatccac 40

<210> SEQ ID NO 198
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 198
ccagcagacc tgtgcagtat gaaggaggtg gagcagacac 40

<210> SEQ ID NO 199
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 199
agatgatgtc tgtggctgtg gtgtctgctc cacctccttc 40

<210> SEQ ID NO 200
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 200
cacagccaca gacatcatct gccccatgta tgccagggtt 40

<210> SEQ ID NO 201
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 201
gggaagggct ggtcctcatc aaccctggca tacatggggc 40

<210> SEQ ID NO 202
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 202
gatgaggacc agcccttccc tgctgtgccc aagtggagca 40

<210> SEQ ID NO 203
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 203
cagagagagc cacttcttga tgctccactt gggcacagca 40

<210> SEQ ID NO 204
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 204
tcaagaagtg gctctctctg cctggagaga ccagacctct 40

<210> SEQ ID NO 205
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 205
gtgcatattc acacaggatc agaggtctgg tctctccagg 40

<210> SEQ ID NO 206
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 206
gatcctgtgt gaatatgcac atgcaatggg caactctctg 40

<210> SEQ ID NO 207
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 207
cagtacttgg caaagcctcc cagagagttg cccattgcat 40

<210> SEQ ID NO 208
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 208
ggaggctttg ccaagtactg gcaagccttc agacagtacc 40

<210> SEQ ID NO 209
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 209
aaatcctcct tgcagcctgg ggtactgtct gaaggcttgc 40

<210> SEQ ID NO 210
<211> LENGTH: 40
<212> TYPE: DNA

<213> ORGANISM: Artificial Sequence
<220> FEATURE:
<223> OTHER INFORMATION: assembling oligo for CpG-free LacZ

<400> SEQUENCE: 210
ccaggctgca aggaggattt gtgtgggact gggtggacca 40

<210> SEQ ID NO 211
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 211
catcatactt gatgagagat tggtccaccc agtcccacac 40

<210> SEQ ID NO 212
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 212
atctctcatc aagtatgatg agaatggcaa cccctggtct 40

<210> SEQ ID NO 213
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 213
ccaaagtctc ctccataggc agaccagggg ttgccattct 40

<210> SEQ ID NO 214
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 214
gcctatggag gagactttgg tgacaccccc aatgacaggc 40

<210> SEQ ID NO 215
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 215
caggccattc atgcagaact gcctgtcatt gggggtgtca 40

<210> SEQ ID NO 216
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 216
agttctgcat gaatggcctg gtctttgcag acaggacccc 40

<210> SEQ ID NO 217
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 217
cctctgtgag ggcagggtga ggggtcctgt ctgcaaagac 40

<210> SEQ ID NO 218
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 218
tcaccctgcc ctcacagagg ccaagcacca gcaacagttc 40

<210> SEQ ID NO 219
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 219
ccagacagcc tgaactggaa gaactgttgc tggtgcttgg 40

<210> SEQ ID NO 220
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 220
ttccagttca ggctgtctgg acagaccatt gaggtgacat 40

<210> SEQ ID NO 221
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 221
gtgcctgaag aggtactcag atgtcacctc aatggtctgt 40

<210> SEQ ID NO 222
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 222
ctgagtacct cttcaggcac tctgacaatg agctcctgca 40

<210> SEQ ID NO 223
<211> LENGTH: 20
<212> TYPE: DNA
<213> ORGANISM: Artificial Sequence
<220> FEATURE:

<223> OTHER INFORMATION: assembling oligo for CpG-free LacZ

<400> SEQUENCE: 223
tgcaggagct cattgtcaga 20

<210> SEQ ID NO 224
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 224
gtaatttaac aatgagctcc tgcactggat ggtggccctg 40

<210> SEQ ID NO 225
<211> LENGTH: 20
<212> TYPE: DNA
<213> ORGANISM: Artificial Sequence
<220> FEATURE:
<223> OTHER INFORMATION: assembling oligo for CpG-free LacZ

<400> SEQUENCE: 225
ggagctcatt gttaaattac 20

<210> SEQ ID NO 226
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 226
gatggcaagc ctctggcttc tggtgaggtg cctctggatg 40

<210> SEQ ID NO 227
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 227
gaagccagag gcttgccatc cagggccacc atccagtgca 40

<210> SEQ ID NO 228
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 228
tggcccctca aggaaagcag ctgattgaac tgcctgagct 40

<210> SEQ ID NO 229
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 229
ctgctttcct tgaggggcca catccagagg cacctcacca 40

-continued

<210> SEQ ID NO 230
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 230
gcctcagcca gagtctgctg gacaactgtg gctaacagtg 40

<210> SEQ ID NO 231
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 231
cagcagactc tggctgaggc agctcaggca gttcaatcag 40

<210> SEQ ID NO 232
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 232
agggtggttc agcccaatgc aacagcttgg tctgaggcag 40

<210> SEQ ID NO 233
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 233
gcattgggct gaaccaccct cactgttagc cacagttgtc 40

<210> SEQ ID NO 234
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 234
gccacatctc tgcatggcag cagtggaggc tggctgagaa 40

<210> SEQ ID NO 235
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 235
ctgccatgca gagatgtggc ctgcctcaga ccaagctgtt 40

<210> SEQ ID NO 236
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 236
cctctctgtg accctgcctg ctgcctctca tgccatccct 40

<210> SEQ ID NO 237
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 237
caggcagggt cacagagagg ttctcagcca gcctccactg 40

<210> SEQ ID NO 238
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 238
cacctgacaa catctgaaat ggacttctgc attgagctgg 40

<210> SEQ ID NO 239
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 239
atttcagatg ttgtcaggtg agggatggca tgagaggcag 40

<210> SEQ ID NO 240
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 240
gcaacaagag atggcagttc aacaggcagt ctggcttcct 40

<210> SEQ ID NO 241
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 241
gaactgccat ctcttgttgc ccagctcaat gcagaagtcc 40

<210> SEQ ID NO 242
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 242
gtctcagatg tggattggag acaagaagca gctcctcacc 40

<210> SEQ ID NO 243
<211> LENGTH: 40

<212> TYPE: DNA
<213> ORGANISM: Artificial Sequence
<220> FEATURE:
<223> OTHER INFORMATION: assembling oligo for CpG-free LacZ

<400> SEQUENCE: 243
ctccaatcca catctgagac aggaagccag actgcctgtt 40

<210> SEQ ID NO 244
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 244
cctctcaggg accaattcac cagggctcct ctggacaatg 40

<210> SEQ ID NO 245
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 245
gtgaattggt ccctgagagg ggtgaggagc tgcttcttgt 40

<210> SEQ ID NO 246
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 246
acattggagt gtctgaggcc accaggattg acccaaatgc 40

<210> SEQ ID NO 247
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 247
ggcctcagac actccaatgt cattgtccag aggagccctg 40

<210> SEQ ID NO 248
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 248
ttgggtggag aggtggaagg ctgctggaca ctaccaggct 40

<210> SEQ ID NO 249
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 249
ccttccacct ctccacccaa gcatttgggt caatcctggt 40

<210> SEQ ID NO 250
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 250
gaggctgccc tgctccagtg cacagcagac accctggctg 40

<210> SEQ ID NO 251
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 251
cactggagca gggcagcctc agcctggtag tgtccagcag 40

<210> SEQ ID NO 252
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 252
atgctgttct gatcaccaca gcccatgctt ggcagcacca 40

<210> SEQ ID NO 253
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 253
tgtggtgatc agaacagcat cagccagggt gtctgctgtg 40

<210> SEQ ID NO 254
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 254
aggcaagacc ctgttcatca gcagaaagac ctacaggatt 40

<210> SEQ ID NO 255
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 255
tgatgaacag ggtcttgcct tggtgctgcc aagcatgggc 40

<210> SEQ ID NO 256
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 256
gatggctctg gacagatggc aatcacagtg gatgtggagg 40

<210> SEQ ID NO 257
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 257
gccatctgtc cagagccatc aatcctgtag gtctttctgc 40

<210> SEQ ID NO 258
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 258
ttgcctctga cacacctcac cctgcaagga ttggcctgaa 40

<210> SEQ ID NO 259
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 259
gtgaggtgtg tcagaggcaa cctccacatc cactgtgatt 40

<210> SEQ ID NO 260
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 260
ctgtcaactg gcacaggtgg ctgagagggt gaactggctg 40

<210> SEQ ID NO 261
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 261
ccacctgtgc cagttgacag ttcaggccaa tccttgcagg 40

<210> SEQ ID NO 262
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 262
ggcttaggcc ctcaggagaa ctaccctgac aggctgacag 40

<210> SEQ ID NO 263
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 263
ttctcctgag ggcctaagcc cagccagttc accctctcag 40

<210> SEQ ID NO 264
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 264
ctgcctgctt tgacaggtgg gacctgcctc tgtctgacat 40

<210> SEQ ID NO 265
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 265
ccacctgtca aagcaggcag ctgtcagcct gtcagggtag 40

<210> SEQ ID NO 266
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 266
gtacacccct tatgtgttcc cttctgagaa tggcctgagg 40

<210> SEQ ID NO 267
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 267
ggaacacata aggggtgtac atgtcagaca gaggcaggtc 40

<210> SEQ ID NO 268
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 268
tgtggcacca gggagctgaa ctatggtcct caccagtgga 40

<210> SEQ ID NO 269
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 269
ttcagctccc tggtgccaca cctcaggcca ttctcagaag 40

<210> SEQ ID NO 270
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 270
ggggagactt ccagttcaac atctccaggt actctcagca 40

<210> SEQ ID NO 271
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 271
gttgaactgg aagtctcccc tccactggtg aggaccatag 40

<210> SEQ ID NO 272
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 272
acagctcatg gaaacctctc acaggcacct gctccatgca 40

<210> SEQ ID NO 273
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 273
gagaggtttc catgagctgt tgctgagagt acctggagat 40

<210> SEQ ID NO 274
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 274
gaggagggaa cctggctgaa cattgatggc ttccacatgg 40

<210> SEQ ID NO 275
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 275
ttcagccagg ttccctcctc tgcatggagc aggtgcctgt 40

<210> SEQ ID NO 276

<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 276
gcattggagg agatgactct tggtctcctt ctgtgtctgc 40

<210> SEQ ID NO 277
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 277
agagtcatct cctccaatgc ccatgtggaa gccatcaatg 40

<210> SEQ ID NO 278
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 278
tgagttccag ttatctgctg gcaggtacca ctatcagctg 40

<210> SEQ ID NO 279
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 279
cagcagataa ctggaactca gcagacacag aaggagacca 40

<210> SEQ ID NO 280
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 280
gtgtggtgcc agaagtaaac ctgagctagc agtccatgat 40

<210> SEQ ID NO 281
<211> LENGTH: 40
<212> TYPE: DNA
<213> ORGANISM: Artificial Sequence
<220> FEATURE:
<223> OTHER INFORMATION: assembling oligo for CpG-free LacZ

<400> SEQUENCE: 281
gtttacttct ggcaccacac cagctgatag tggtacctgc 40

<210> SEQ ID NO 282
<211> LENGTH: 20
<212> TYPE: DNA
<213> ORGANISM: Artificial Sequence
<220> FEATURE:
<223> OTHER INFORMATION: assembling oligo for CpG-free LacZ

<400> SEQUENCE: 282
atcatggact gctagctcag 20

<210> SEQ ID NO 283
<211> LENGTH: 40
<212> TYPE: DNA
<213> ORGANISM: Artificial Sequence
<220> FEATURE:
<223> OTHER INFORMATION: assembling oligo for R6K gamma M2A replication origin

<400> SEQUENCE: 283
gcaggactga ggcttaatta aaccttaaaa cctttaaaag 40

<210> SEQ ID NO 284
<211> LENGTH: 40
<212> TYPE: DNA
<213> ORGANISM: Artificial Sequence
<220> FEATURE:
<223> OTHER INFORMATION: assembling oligo for R6K gamma M2A replication origin

<400> SEQUENCE: 284
ccttatatat tcttttttt cttataaaac ttaaaacctt 40

<210> SEQ ID NO 285
<211> LENGTH: 40
<212> TYPE: DNA
<213> ORGANISM: Artificial Sequence
<220> FEATURE:
<223> OTHER INFORMATION: assembling oligo for R6K gamma M2A replication origin

<400> SEQUENCE: 285
agaggctatt taagttgctg atttatatta attttattgt 40

<210> SEQ ID NO 286
<211> LENGTH: 50
<212> TYPE: DNA
<213> ORGANISM: Artificial Sequence
<220> FEATURE:
<223> OTHER INFORMATION: assembling oligo for R6K gamma M2A replication origin

<400> SEQUENCE: 286
tcaaacatga gagcttagta catgaaacat gagagcttag tacattagcc 50

<210> SEQ ID NO 287
<211> LENGTH: 60
<212> TYPE: DNA
<213> ORGANISM: Artificial Sequence
<220> FEATURE:
<223> OTHER INFORMATION: assembling oligo for R6K gamma M2A replication origin

<400> SEQUENCE: 287
atgagagctt agtacattag ccatgagggt ttagttcatt aaacatgaga gcttagtaca 60

<210> SEQ ID NO 288
<211> LENGTH: 60
<212> TYPE: DNA
<213> ORGANISM: Artificial Sequence
<220> FEATURE:
<223> OTHER INFORMATION: assembling oligo for R6K gamma M2A replication origin

<400> SEQUENCE: 288
ttaaacatga gagcttagta catgaaacat gagagcttag tacatactat caacaggttg 60

<210> SEQ ID NO 289
<211> LENGTH: 30
<212> TYPE: DNA
<213> ORGANISM: Artificial Sequence
<220> FEATURE:
<223> OTHER INFORMATION: assembling oligo for R6K gamma M2A replication origin

<400> SEQUENCE: 289
aactgctgat cttaattaac ctggagactt 30

<210> SEQ ID NO 290
<211> LENGTH: 60
<212> TYPE: DNA
<213> ORGANISM: Artificial Sequence
<220> FEATURE:
<223> OTHER INFORMATION: assembling oligo for R6K gamma M2A replication origin

<400> SEQUENCE: 290
aagtctccag gttaattaag atcagcagtt caacctgttg atagtatgta ctaagctctc 60

<210> SEQ ID NO 291
<211> LENGTH: 60
<212> TYPE: DNA
<213> ORGANISM: Artificial Sequence
<220> FEATURE:
<223> OTHER INFORMATION: assembling oligo for R6K gamma M2A replication origin

<400> SEQUENCE: 291
atgtttcatg tactaagctc tcatgtttaa tgtactaagc tctcatgttt aatgaactaa 60

<210> SEQ ID NO 292
<211> LENGTH: 60
<212> TYPE: DNA
<213> ORGANISM: Artificial Sequence
<220> FEATURE:
<223> OTHER INFORMATION: assembling oligo for R6K gamma M2A replication origin

<400> SEQUENCE: 292
accctcatgg ctaatgtact aagctctcat ggctaatgta ctaagctctc atgtttcatg 60

<210> SEQ ID NO 293
<211> LENGTH: 40
<212> TYPE: DNA
<213> ORGANISM: Artificial Sequence
<220> FEATURE:
<223> OTHER INFORMATION: assembling oligo for R6K gamma M2A replication origin

<400> SEQUENCE: 293
tactaagctc tcatgtttga acaataaaat taatataaat 40

<210> SEQ ID NO 294
<211> LENGTH: 40
<212> TYPE: DNA
<213> ORGANISM: Artificial Sequence
<220> FEATURE:
<223> OTHER INFORMATION: assembling oligo for R6K gamma M2A replication origin

<400> SEQUENCE: 294
cagcaactta aatagcctct aaggttttaa gttttataag 40

<210> SEQ ID NO 295
<211> LENGTH: 40
<212> TYPE: DNA
<213> ORGANISM: Artificial Sequence
<220> FEATURE:
<223> OTHER INFORMATION: assembling oligo for R6K gamma M2A replication origin

<400> SEQUENCE: 295
aaaaaaaaga atatataagg cttttaaagg ttttaaggtt 40

<210> SEQ ID NO 296
<211> LENGTH: 20
<212> TYPE: DNA
<213> ORGANISM: Artificial Sequence
<220> FEATURE:
<223> OTHER INFORMATION: assembling oligo for R6K gamma M2A replication origin

<400> SEQUENCE: 296
taattaagcc tcagtcctgc 20

<210> SEQ ID NO 297
<211> LENGTH: 66
<212> TYPE: DNA
<213> ORGANISM: Artificial Sequence
<220> FEATURE:
<223> OTHER INFORMATION: EM7 promotor

<400> SEQUENCE: 297
caattaatca tcggcatagt atatcggcat agtataatac gactcactat aggagggcca 60
ccatgg 66

<210> SEQ ID NO 298
<211> LENGTH: 66
<212> TYPE: DNA
<213> ORGANISM: Artificial Sequence
<220> FEATURE:
<223> OTHER INFORMATION: degenerated oligo for assembling the GpG-Free EM2K promotor

<400> SEQUENCE: 298
caattaawca tdggcatagt atatcwgcat agtataatac hactcactat aggagggcca 60
ccatgg 66

<210> SEQ ID NO 299
<211> LENGTH: 20
<212> TYPE: DNA
<213> ORGANISM: Artificial Sequence
<220> FEATURE:
<223> OTHER INFORMATION: sense oligo for the assembly of SEQ ID NO: 38-74 oligos

<400> SEQUENCE: 299
ttcagctgag gaggcacatc 20

<210> SEQ ID NO 300
<211> LENGTH: 20
<212> TYPE: DNA
<213> ORGANISM: Artificial Sequence
<220> FEATURE:
<223> OTHER INFORMATION: reverse oligo for the assembly of SEQ ID NO: 38-74 oligos

<400> SEQUENCE: 300

-continued

```
ctcaggatcc gctagctaat                                          20


<210> SEQ ID NO 301
<211> LENGTH: 18
<212> TYPE: DNA
<213> ORGANISM: Artificial Sequence
<220> FEATURE:
<223> OTHER INFORMATION: sense primer pur 24

<400> SEQUENCE: 301

aggaccatca tgactgag                                            18


<210> SEQ ID NO 302
<211> LENGTH: 18
<212> TYPE: DNA
<213> ORGANISM: Artificial Sequence
<220> FEATURE:
<223> OTHER INFORMATION: reverse primer pur 25

<400> SEQUENCE: 302

atcatgtcga gctagctc                                            18


<210> SEQ ID NO 303
<211> LENGTH: 31
<212> TYPE: DNA
<213> ORGANISM: Artificial Sequence
<220> FEATURE:
<223> OTHER INFORMATION: RK15 primer

<400> SEQUENCE: 303

gcaggactga ggcttaatta aaccttaaaa c                             31


<210> SEQ ID NO 304
<211> LENGTH: 31
<212> TYPE: DNA
<213> ORGANISM: Artificial Sequence
<220> FEATURE:
<223> OTHER INFORMATION: RK16 primer

<400> SEQUENCE: 304

aagtctccag gttaattaag atcagcagtt c                             31


<210> SEQ ID NO 305
<211> LENGTH: 52
<212> TYPE: DNA
<213> ORGANISM: Artificial Sequence
<220> FEATURE:
<223> OTHER INFORMATION: rps0-1 linker oligo

<400> SEQUENCE: 305

ctagctgagt ttcagaaaag ggggcctgag tggccccttt tttcaactta at      52


<210> SEQ ID NO 306
<211> LENGTH: 46
<212> TYPE: DNA
<213> ORGANISM: Artificial Sequence
<220> FEATURE:
<223> OTHER INFORMATION: rps0-2 linker oligo

<400> SEQUENCE: 306

taagttgaaa aaaggggcca ctcaggcccc cttttctgaa actcag             46


<210> SEQ ID NO 307
<211> LENGTH: 39
<212> TYPE: DNA
```

```
<213> ORGANISM: Artificial Sequence
<220> FEATURE:
<223> OTHER INFORMATION: PACI-UP primer

<400> SEQUENCE: 307

atcgttaatt aaaacagtag ttgacaatta aacattggc                             39


<210> SEQ ID NO 308
<211> LENGTH: 28
<212> TYPE: DNA
<213> ORGANISM: Artificial Sequence
<220> FEATURE:
<223> OTHER INFORMATION: PACI-DOWN primer

<400> SEQUENCE: 308

atcgttaatt aagttgaaaa aaggggcc                                         28


<210> SEQ ID NO 309
<211> LENGTH: 17
<212> TYPE: DNA
<213> ORGANISM: Artificial Sequence
<220> FEATURE:
<223> OTHER INFORMATION: rbs-1 linker oligo

<400> SEQUENCE: 309

aattctgagg agaagct                                                     17


<210> SEQ ID NO 310
<211> LENGTH: 17
<212> TYPE: DNA
<213> ORGANISM: Artificial Sequence
<220> FEATURE:
<223> OTHER INFORMATION: rbs-2 linker oligo

<400> SEQUENCE: 310

catgagcttc tcctcag                                                     17


<210> SEQ ID NO 311
<211> LENGTH: 36
<212> TYPE: DNA
<213> ORGANISM: Artificial Sequence
<220> FEATURE:
<223> OTHER INFORMATION: OL dcm AF primer

<400> SEQUENCE: 311

ttttgcggcc gcttgctgcg ccagcaacta ataacg                                36


<210> SEQ ID NO 312
<211> LENGTH: 41
<212> TYPE: DNA
<213> ORGANISM: Artificial Sequence
<220> FEATURE:
<223> OTHER INFORMATION: OL dcm AR primer

<400> SEQUENCE: 312

ccttggatcc tggtaaacac gcactgtccg ccaatcgatt c                          41


<210> SEQ ID NO 313
<211> LENGTH: 30
<212> TYPE: DNA
<213> ORGANISM: Artificial Sequence
<220> FEATURE:
<223> OTHER INFORMATION: OL dcm BF primer

<400> SEQUENCE: 313

ttttggatcc tcagcaagag gcacaacatg                                       30
```

<210> SEQ ID NO 314
<211> LENGTH: 35
<212> TYPE: DNA
<213> ORGANISM: Artificial Sequence
<220> FEATURE:
<223> OTHER INFORMATION: OL dcm BR primer

<400> SEQUENCE: 314
ttttctcgag aaacggcagc tctgatactt gcttc 35

<210> SEQ ID NO 315
<211> LENGTH: 32
<212> TYPE: DNA
<213> ORGANISM: Artificial Sequence
<220> FEATURE:
<223> OTHER INFORMATION: OL dcm CF primer

<400> SEQUENCE: 315
ttttgcggcc gcgttgcggt attacccttg tc 32

<210> SEQ ID NO 316
<211> LENGTH: 795
<212> TYPE: DNA
<213> ORGANISM: Artificial Sequence
<220> FEATURE:
<223> OTHER INFORMATION: Neo DeltaCpG
<220> FEATURE:
<221> NAME/KEY: CDS
<222> LOCATION: (1)..(795)
<223> OTHER INFORMATION: neo gene without CpG

<400> SEQUENCE: 316

```
atg att gaa caa gat ggc cta cat gca ggt tct cca gct gcc tgg gtt      48
Met Ile Glu Gln Asp Gly Leu His Ala Gly Ser Pro Ala Ala Trp Val
1               5                   10                  15

gag aga ctg ttt ggc tat gac tgg gca cag cag acc att ggt tgc tct      96
Glu Arg Leu Phe Gly Tyr Asp Trp Ala Gln Gln Thr Ile Gly Cys Ser
            20                  25                  30

gat gca gca gtt ttc aga ctt tca gcc caa ggc agg cca gtc ctt ttt     144
Asp Ala Ala Val Phe Arg Leu Ser Ala Gln Gly Arg Pro Val Leu Phe
        35                  40                  45

gta aag aca gac ctc agt ggg gct ctc aat gag ctc cag gat gag gct     192
Val Lys Thr Asp Leu Ser Gly Ala Leu Asn Glu Leu Gln Asp Glu Ala
    50                  55                  60

gcc aga ctc tcc tgg ttg gca aca act ggg gtc ccc tgt gca gct gtc     240
Ala Arg Leu Ser Trp Leu Ala Thr Thr Gly Val Pro Cys Ala Ala Val
65                  70                  75                  80

ctt gat gtg gtc aca gaa gct gga agg gac tgg ctc cta cta ggt gag     288
Leu Asp Val Val Thr Glu Ala Gly Arg Asp Trp Leu Leu Leu Gly Glu
                85                  90                  95

gtg cct ggg cag gac ctc ctt tcc tct cac cta gct cca gct gag aaa     336
Val Pro Gly Gln Asp Leu Leu Ser Ser His Leu Ala Pro Ala Glu Lys
            100                 105                 110

gtg tca atc atg gct gat gcc atg aga aga ctc cac acc ctt gac cca     384
Val Ser Ile Met Ala Asp Ala Met Arg Arg Leu His Thr Leu Asp Pro
        115                 120                 125

gcc acc tgc ccc ttt gac cac cag gcc aag cac agg ata gag agg gcc     432
Ala Thr Cys Pro Phe Asp His Gln Ala Lys His Arg Ile Glu Arg Ala
    130                 135                 140

aga acc agg atg gag gct ggc ctg gtg gac caa gat gac ttg gat gaa     480
Arg Thr Arg Met Glu Ala Gly Leu Val Asp Gln Asp Asp Leu Asp Glu
145                 150                 155                 160
```

-continued

```
gaa cac cag ggc ctg gcc cct gct gaa cta ttt gcc agg ctc aag gca      528
Glu His Gln Gly Leu Ala Pro Ala Glu Leu Phe Ala Arg Leu Lys Ala
                165                 170                 175

tcc atg cca gat ggt gag gac cta gtg gtg act cat ggg gat gcc tgc      576
Ser Met Pro Asp Gly Glu Asp Leu Val Val Thr His Gly Asp Ala Cys
            180                 185                 190

ctt ccc aac atc atg gtt gaa aat gga agg ttc tct ggc ttc ata gac      624
Leu Pro Asn Ile Met Val Glu Asn Gly Arg Phe Ser Gly Phe Ile Asp
        195                 200                 205

tgt ggc agg ctg gga gtg gct gac agg tac cag gac att gcc cta gca      672
Cys Gly Arg Leu Gly Val Ala Asp Arg Tyr Gln Asp Ile Ala Leu Ala
    210                 215                 220

acc agg gac ata gca gaa gag cta ggg gga gag tgg gca gac agg ttc      720
Thr Arg Asp Ile Ala Glu Glu Leu Gly Gly Glu Trp Ala Asp Arg Phe
225                 230                 235                 240

cta gtg ctc tat ggc att gca gcc cct gac tcc cag aga att gcc ttc      768
Leu Val Leu Tyr Gly Ile Ala Ala Pro Asp Ser Gln Arg Ile Ala Phe
                245                 250                 255

tac aga ctt ctt gat gag ttc ttc taa                                  795
Tyr Arg Leu Leu Asp Glu Phe Phe
            260


<210> SEQ ID NO 317
<211> LENGTH: 264
<212> TYPE: PRT
<213> ORGANISM: Artificial Sequence
<220> FEATURE:
<223> OTHER INFORMATION: Neo DeltaCpG

<400> SEQUENCE: 317

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Ser Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220
```

Thr Arg Asp Ile Ala Glu Glu Leu Gly Gly Glu Trp Ala Asp Arg Phe
225 230 235 240

Leu Val Leu Tyr Gly Ile Ala Ala Pro Asp Ser Gln Arg Ile Ala Phe
245 250 255

Tyr Arg Leu Leu Asp Glu Phe Phe
260

<210> SEQ ID NO 318
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 318
cattaccggt aggcacatca tgattgaaca agatggccta 40

<210> SEQ ID NO 319
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 319
catgcaggtt ctccagctgc ctgggttgag agactgtttg 40

<210> SEQ ID NO 320
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 320
gctatgactg ggcacagcag accattggtt gctctgatgc 40

<210> SEQ ID NO 321
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 321
agcagttttc agactttcag cccaaggcag gccagtcctt 40

<210> SEQ ID NO 322
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 322
tttgtaaaga cagacctcag tggggctctc aatgagctcc 40

<210> SEQ ID NO 323
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 323

-continued aggatgaggc tgccagactc tcctggttgg caacaactgg 40

<210> SEQ ID NO 324
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 324
ggtcccctgt gcagctgtcc ttgatgtggt cacagaagct 40

<210> SEQ ID NO 325
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 325
ggaagggact ggctcctact aggtgaggtg cctgggcagg 40

<210> SEQ ID NO 326
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 326
acctcctttc ctctcaccta gctccagctg agaaagtgtc 40

<210> SEQ ID NO 327
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 327
aatcatggct gatgccatga gaagactcca cacccttgac 40

<210> SEQ ID NO 328
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 328
ccagccacct gcccctttga ccaccaggcc aagcacagga 40

<210> SEQ ID NO 329
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 329
tagagagggc cagaaccagg atggaggctg gcctggtgga 40

<210> SEQ ID NO 330
<211> LENGTH: 40
<212> TYPE: DNA

<213> ORGANISM: Artificial Sequence
<220> FEATURE:
<223> OTHER INFORMATION: oligo for construction of Neo DeltaCpG

<400> SEQUENCE: 330
ccaagatgac ttggatgaag aacaccaggg cctggcccct 40

<210> SEQ ID NO 331
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 331
gctgaactat ttgccaggct caaggcatcc atgccagatg 40

<210> SEQ ID NO 332
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 332
gtgaggacct agtggtgact catggggatg cctgccttcc 40

<210> SEQ ID NO 333
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 333
caacatcatg gttgaaaatg gaaggttctc tggcttcata 40

<210> SEQ ID NO 334
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 334
gactgtggca ggctgggagt ggctgacagg taccaggaca 40

<210> SEQ ID NO 335
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 335
ttgccctagc aaccagggac atagcagaag agctaggggg 40

<210> SEQ ID NO 336
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 336
agagtgggca gacaggttcc tagtgctcta tggcattgca 40

<210> SEQ ID NO 337
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 337
gcccctgact cccagagaat tgccttctac agacttcttg 40

<210> SEQ ID NO 338
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 338
atgagttctt ctaaagctag ctgatcctga tagctgttcg 40

<210> SEQ ID NO 339
<211> LENGTH: 20
<212> TYPE: DNA
<213> ORGANISM: Artificial Sequence
<220> FEATURE:
<223> OTHER INFORMATION: oligo for construction of Neo DeltaCpG

<400> SEQUENCE: 339
cgaacagcta tcaggatcag 20

<210> SEQ ID NO 340
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 340
ctagctttag aagaactcat caagaagtct gtagaaggca 40

<210> SEQ ID NO 341
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 341
attctctggg agtcaggggc tgcaatgcca tagagcacta 40

<210> SEQ ID NO 342
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 342
ggaacctgtc tgcccactct ccccctagct cttctgctat 40

<210> SEQ ID NO 343
<211> LENGTH: 40
<212> TYPE: DNA
<213> ORGANISM: Artificial Sequence
<220> FEATURE:

<223> OTHER INFORMATION: oligo for construction of Neo DeltaCpG

<400> SEQUENCE: 343
gtccctggtt gctagggcaa tgtcctggta cctgtcagcc 40

<210> SEQ ID NO 344
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 344
actcccagcc tgccacagtc tatgaagcca gagaaccttc 40

<210> SEQ ID NO 345
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 345
cattttcaac catgatgttg ggaaggcagg catccccatg 40

<210> SEQ ID NO 346
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 346
agtcaccact aggtcctcac catctggcat ggatgccttg 40

<210> SEQ ID NO 347
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 347
agcctggcaa atagttcagc aggggccagg ccctggtgtt 40

<210> SEQ ID NO 348
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 348
cttcatccaa gtcatcttgg tccaccaggc cagcctccat 40

<210> SEQ ID NO 349
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 349
cctggttctg gccctctcta tcctgtgctt ggcctggtgg 40

-continued

<210> SEQ ID NO 350
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 350
tcaaaggggc aggtggctgg gtcaagggtg tggagtcttc 40

<210> SEQ ID NO 351
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 351
tcatggcatc agccatgatt gacactttct cagctggagc 40

<210> SEQ ID NO 352
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 352
taggtgagag gaaaggaggt cctgcccagg cacctcacct 40

<210> SEQ ID NO 353
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 353
agtaggagcc agtcccttcc agcttctgtg accacatcaa 40

<210> SEQ ID NO 354
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 354
ggacagctgc acaggggacc ccagttgttg ccaaccagga 40

<210> SEQ ID NO 355
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 355
gagtctggca gcctcatcct ggagctcatt gagagcccca 40

<210> SEQ ID NO 356
<211> LENGTH: 40
<212> TYPE: DNA
<213> ORGANISM: Artificial Sequence
<220> FEATURE:
<223> OTHER INFORMATION: oligo for construction of Neo DeltaCpG -continued

```
<400> SEQUENCE: 356

ctgaggtctg tctttacaaa aaggactggc ctgccttggg                    40


<210> SEQ ID NO 357
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 357

ctgaaagtct gaaaactgct gcatcagagc aaccaatggt                    40


<210> SEQ ID NO 358
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 358

ctgctgtgcc cagtcatagc caaacagtct ctcaacccag                    40


<210> SEQ ID NO 359
<211> LENGTH: 40
<212> TYPE: DNA
<213> ORGANISM: Artificial Sequence
<220> FEATURE:
<223> OTHER INFORMATION: oligo for construction of Neo DeltaCpG

<400> SEQUENCE: 359

gcagctggag aacctgcatg taggccatct tgttcaatca                    40


<210> SEQ ID NO 360
<211> LENGTH: 20
<212> TYPE: DNA
<213> ORGANISM: Artificial Sequence
<220> FEATURE:
<223> OTHER INFORMATION: oligo for construction of Neo DeltaCpG

<400> SEQUENCE: 360

tgatgtgcct accggtaatg                                          20
```

SYNTHETIC GENES AND BACTERIAL PLASMIDS DEVOID OF CPG

This application is the US national phase of international application PCT/FR02/00862 filed 11 Mar. 2002, which designated the US.

FIELD OF THE INVENTION

The present application relates to synthetic genes and to plasmids entirely devoid of CpG.

TECHNOLOGICAL BACKGROUND

Plasmids are genetic elements essentially found in bacteria, made up of a molecule of deoxyribonucleic acid, which is most commonly circular and the replication of which is autonomous and independent from that of genomic DNA. Natural plasmids isolated from a very broad variety of bacteria are capable of accomplishing several cellular functions. The first, which is vital for all plasmids, is that responsible for their replication, generally carried out in a manner which is synchronized with replication of the genomic DNA and cell division. Besides the region required for replication of the plasmid, all natural plasmids carry genes which encode proteins, the function of which most commonly remains unknown due to a lack of scientific investigation with regard to these genes. The number of genes present on a plasmid determines the size of this plasmid, the smallest natural plasmids containing only two to three genes. The properties of plasmids attracted research scientists to them very early on, to make them vehicles for transporting and expressing genes in prokaryotic cells, as well as in eukaryotic cells. The very rapid progress observed in the fields of the molecular biology of nucleic acids and proteins, over the past two decades, can in part be attributed to the exploitation of recombined plasmids constructed from fragments of natural DNA of plasmid origin or other cellular DNAs, and even chemically synthesized.

The four bases adenine (A), guanine (G), cytosine (C) and thymine (T) which constitute deoxyribonucleic acid (DNA) are distributed in 16 dinucleotide configurations, namely CG, GC, TA, AT, CC, GG, TT, AA, TG, CA, AG, CT, AC, GT, GA and TC. Analysis of the qualitative distribution of the dinucleotides of the DNA of thousands of plasmids for which sequences are known reveals that the 16 dinucleotides are always present in all natural plasmids or plasmids constructed in the laboratory. However, analysis of the quantitative distribution of the dinucleotides of plasmids shows great disparities which depend, only partly, on the percentage of each one of the four bases of the DNA. Specifically, comparison of the frequencies observed for each one of the dinucleotides with those of the frequencies calculated on the basis of a random association between two bases, for a given plasmid, can demonstrate major differences for several dinucelotides in terms of an over representation, or, on the contrary, an under representation (Campbell A., Mrazek J. and Karlin S. (1999) *Proc Natl Acad Sci USA* 96, 9184-9). The differences observed in the distribution of certain dinucleotides, not always the same, of natural plasmids isolated from bacteria of phylogenically distant species have been explained by differences in specificity in the mechanisms of repair, recombination and replication acting on the cellular DNAs.

Gene transfers in vitro into cells in culture and in vivo into various animals are common practices undergoing great development, on the one hand, for the purpose of gaining a better understanding of cell function and, on the other hand, in order to apply these techniques to cell and gene therapies. None of the viral vectors and plasmid vectors among the panoply of vectors available for gene transfer in animals has taken a decisive advantage over the others, since each one has advantages, but also disadvantages. There is, however, an application in which naked plasmid DNA or plasmid DNA complexed with various substances to facilitate DNA transport to the nucleus is the subject of intense research activity, namely that of immunizing DNA. The principle of immunizing DNA is based on the immune responses observed in laboratory animals treated, by intramuscular or intradermal injection or by inhalation, with plasmid DNA encoding an antigenic peptide. It is now well established that a first consequence of introducing a plasmid DNA derived from the bacteria *E. coli* into the body of an experimental animal intravenously and intramuscularly is the rapid production of various cytokines by the guard cells of the immune system (Krieg A. M. and Kline J. N. (2000) *Immunopharmacology* 48, 303-305). This response is extremely specific for bacterial DNA since DNA extracted from animal cells does not cause such an induction of cytokines under the same conditions. The cellular mechanisms involved in this immune response are far from being fully understood. However, it is known that the recognition which discriminates between bacterial DNA and DNA of animal origin takes place at the level of structural differences relating to the methylation of certain cytosines of the molecule. Specifically, mammalian DNA is naturally methylated at the cytosine of all CG dinucleotides (subsequently written CpG), with the exception of short regions of high CpG density, called CpG islands, present in functional regions in some promoters. DNA extracted from *E. coli* does not exhibit this type of methylation due to the absence of the enzyme activity capable of accomplishing this modification in this bacterium. It is, however, possible to methylate the CpGs of plasmid DNA extracted from *E. coli* in a test tube with an appropriate enzyme. Under these conditions, DNA methylated in vitro loses a great deal of its immunostimulant activity compared to control nonmethylated DNA. The *E. coli* strain K12, from which virtually all the mutant strains used to produce plasmid DNAs are derived, contains an enzyme activity (DNA methylase dcm (Palmer B. R. and Marinus M. G. (1994) *Gene* 143, 1-12)) which leads to methylation of cytosine occurring in the nucleic acid context CC(A/T)GG. All plasmid vectors for gene transfer contain this sequence in varying number and, as a result, their DNA molecule contains methylated cytosines which are not found in mammalian DNA. This form of methylation specific to *E. coli* thus introduces another difference into the cytosine methylations between bacterial DNA and that of mammals, which might contribute to the immunostimulant capacity of plasmid DNA.

The CpG frequency in primate and rodent DNAs is, overall, much lower than that expected on the basis of the frequency of cytosines and guanines. The CpG deficiency is dependent, for a given DNA fragment, on the biological role of this fragment, intergenic regions containing only a fifth of the expected frequency, while exons have a less marked deficiency and, at the other extreme, some promoters containing a large CpG island exhibit a CpG percentage close to that expected. Analysis of the data from sequencing human cDNAs and chromosomes reveals, however, broad heterogeneities in the CpG frequency for promoter regions and cDNAs. This observation is illustrated by the cDNA of the human gene encoding interleukin 2, which has just one CpG. Similarly, a portion of the promoter of this gene containing the TATA box does not contain any CpG, but, on the other hand, the upstream portion rich in transcription factor recognition sites contains CpGs. The regions positioned 3' of the genes, formed by the 3' UTRs (untranslated regions) and the polyadenylation and end of transcription sequences are rather poor in CpG. In humans, it is not unusual to find regions immediately downstream of the genes, which are devoid of CpG. However, the human sequencing data available at the end of 2000 have not made it possible to demonstrate a single transcriptional unit, made up of the transcription promoter regions, a gene with or without an intron and the polyadenylation region, which is completely devoid of CpG. The situation of the CpGs in *E. coli* is quite different from that of animal cells since the frequency of CpGs in the genomic DNA of this bacterium is slightly greater compared to the calculated frequency. The same is true for the CpGs of natural plasmids isolated from hospital strains of *E. coli*. The recombined plasmids resulting from genetic manipulations, used for gene transfer, exhibit variations in their CpG numbers which depend on the origin of the fragments inserted into the vector. Analysis of the sequences of several tens of recombined *E. coli* plasmids randomly taken from the GenBank databank shows that the plasmids most lacking in CpG have, at the very most, a 50% deficiency in the number of their CpGs.

As regards the present invention, it provides products and methods for synthesizing plasmid DNA in *E. coli* which is completely devoid of CpG and in which the cytosines placed in the context CC(A/T)GG are not methylated. To the applicant's knowledge, this is the first description of such products which exhibit such a structure while at the same time having conserved their function.

DESCRIPTION OF THE INVENTION

The present invention provides means for producing plasmids which are functional in a prokaryotic organism such as *Escherichia coli*, but which are nevertheless completely devoid of CpG. More particularly it provides means for producing plasmids which are completely devoid of CpG, and which are also free of cytosine methylation in the nucleic acid context CC(A/T)GG.

The present application thus relates to methods for producing such plasmids, and also to the elements constituting these plasmids, namely genes devoid of CpG which can be expressed in *E. coli*, promoters devoid of CpG which are suitable for the expression of said genes, and origins of replication devoid of CpG which are suitable for the bacterial transformation of said plasmids. The present application is also directed towards the biotechnological and medical applications of these products. Each one of these products has the particular characteristic of being completely devoid of CpG, while at the same time having conserved its functionality in a prokaryote such as *E. coli*. The present application also provides an *E. coli* strain specially suited to the production of the plasmids according to the invention, this strain having the particular characteristic of allowing stable replication of these plasmids and of the genetic material which they transport, without impairing their function, and without, however, inducing methylation at CC(A/T)GG sites (strain comprising an inactivated dcm gene).

One of the common concepts linking the various aspects of the invention is therefore to make it possible to produce plasmids which are completely devoid of CpG and which have, despite everything, conserved their functional properties in a prokaryote such as *E. coli*. To the applicant's knowledge, this is the first description of such means.

The present application is thus directed toward a method for producing a plasmid which is a vector of at least one gene, and which is completely devoid of CpG characterized in that a plasmid is constructed by assembling, by enzyme ligation, DNA fragments, all devoid of CpG, corresponding to an origin of replication for the plasmid and to elements constituting a transcriptional unit for said at least one gene, and in that this plasmid is transferred into an *Escherichia coli* strain expressing the pi protein for replication of the plasmid.

Plasmids isolated from wild-type bacterial strains generally accomplish three functions in relation to replication, namely initiation of DNA replication, control of replication and stable maintenance of the plasmid during successive divisions. Plasmids constructed in the laboratory do not always exhibit all of these functions. The number of copies of the plasmids is, for example, quite often increased compared to the parent plasmid, denoting that replication control elements have been modified. The plasmid R6K contains three origins of replication, alpha, gamma and beta, linked on the same DNA fragment (Filutowicz M. and Rakowski S. A. (1998) *Gene* 223, 195-204). Each one of the origins is activated by the R6K specific pi initiation protein encoded by the R6K pir gene. In order to be functional, the three origins need a 277 bp sequence, known by those skilled in the art as "core", located at the center of the fragment carrying the three origins, and also an additional single fragment positioned in cis, i.e. present on the same DNA molecule. When the sequences of the alpha and beta origins are deleted, the remaining gamma origin allows autonomous duplication of the plasmid on the condition that the pir gene is present in cis on the plasmid or in trans on the chromosome of the bacterium. The inventors chose to focus more particularly on the smallest of the three origins, namely the gamma origin, which has the advantage of containing all the elements required for controlled replication of the plasmid, namely the core and an adjacent activating sequence. The core is made up of a pi protein-binding sequence repeated 7 times, and an AT-rich sequence. The activating region contains binding sites for several cellular proteins of the bacterium, required for stably maintaining the plasmid. The number of copies of the plasmids containing only the gamma origin depends on the pi protein; mutant forms of pi leading to a large increase in the number of copies of the plasmid have been isolated and characterized. As shown in greater detail in the examples below, the inventors have succeeded in constructing, from the gamma origin of replication of the plasmid R6K, origins of replication which no longer exhibit any CpG, while at the same time having conserved their functionality intact. It may be noted that the specific choice of R6K gamma as starting material, namely the choice of a small replicon which exhibits only a small number of CpG, is a particularly relevant choice insofar as, when other plasmids such as those of the pUC series are used as starting material, CpG-free plasmids which remain functional are not successfully obtained: all the attempts made by the inventors to chemically reconstitute the minimum pUC sequence by replacing the cytosines of CpGs with guanine or adenine resulted in DNA fragments which had lost all functional replication activity. As regards the plasmids which comprise a CpG-free origin of replication according to the invention, they have conserved their ability to replicate stably within a prokaryote cell such as *E. coli*, and *E. coli* K12 in particular, provided, of course, that they are provided with the pi protein required to activate the replication (wild-type pir or mutated pir such as pir 116 in cis or in trans). An origin of replication for plasmid according to the invention is characterized in that its sequence corresponds to that of the R6K gamma origin of replication in which each G of the CpGs of the repeat-region of the core has been replaced with an A, a C or a T, or each C of the CpGs has been replaced with a G, an A or a T. Various CpG-free origins of replication have thus been obtained, which, surprisingly, are still capable of performing the functions of origin of replication of plasmids in *E. coli* and, what is more, are capable of performing these functions for genes and transcriptional units which are themselves devoid of CpG. The examples below give some illustrations thereof (cf. origins R6K gamma M2A, R6K gamma M2C, R6K gamma M2T in examples 7-10). The present application is directed more particularly toward any origin of replication whose sequence comprises the sequence SEQ ID No. 12 or SEQ ID No. 13 (FIGS. 12 and 14). It has also been demonstrated that the pi protein-binding sequence can be not repeated 7 times, as is observed in the standard R6K gamma origin with CpG, but that the number thereof can be limited to 5 or 6, without however impairing the functions of the origin of replication. The present application is thus directed toward any origin of replication according to the invention as defined above, which would comprise only 5 or 6 repeats of the pi protein-binding sequence. By virtue of these CpG-free functional origins of replication, the inventors have been able to construct various plasmids which, notably, have conserved their transfection vector functions.

The creation of *E. coli* plasmids devoid of CpG necessarily requires having functional genes (which can be expressed in prokaryotes such as *E. coli*) which do not contain any CpG. Thus, selection of the bacteria transformed with a recombined plasmid DNA involves a gene whose protein confers a dominant advantage on the bacterium. Most commonly, the selective marker is introduced by a gene for resistance to an antibiotic which is active on the *E. coli* bacterium. Analysis of the wide variety of resistance genes used in *E. coli* shows that, without exception, they all contain CpGs, very often in very high numbers for resistance genes originating from *Streptomyces* which produce the antibiotic for selection. Similarly, it is necessary to have reporter genes which are CpG-free while at the same time remaining functional.

Analysis of several hundred chromosomal and plasmid genes of the *E. coli* bacterium, the well-characterized sequences of which are available in several databanks, reveals that all genes greater than 250 pb in size, without exception, consist of 16 dinucleotides.

The present invention demonstrates that it is, despite everything, possible to construct genes which are functional in *E. coli* and which are devoid of CpG. The inventors have in fact developed a method for obtaining genes devoid of CpG while at the same time being able to be expressed in *E. coli*. This method is based on the synthesis of a polynucleotide chain by following the amino acid chain of a protein which can be expressed in *E. coli*, assigning to each amino acid a nucleotide codon chosen from those which, according to the genetic code, and taking into account the degeneracy of this code, correspond to this amino acid, but eliminating from this choice:

i. all codons containing a CpG in their sequence: this concerns the codons ACG (Thr), CCG (Pro), GCG (Ala), TCG (Ser), CGA (Arg), CGC (Arg), CGG (Arg) and CGT (Arg), and ii. codons which finish with a C when the codon which follows it directly begins with a G. Examples of a gene thus obtained comprise the NeoΔCpG gene (SEQ ID No 316; cf. example 11).

According to one variant of implementation of the invention, the codons for which the frequencies are low in proteins of human origin will also be eliminated from said choice: this concerns the codons ATA (Ile), CTA (Leu), GTA (Val) and TTA (Leu). The set of possible codons therefore, according to this variant, corresponds to the following set:

GCA (Ala), GCC (Ala), GCT (Ala), AGA (Arg), AGG (Arg), AAC (Asn), AAT (Asn), GAC (Asp), GAT (Asp), TGC (Cys), TGT (Cys), CAA (Gln), CAG (Gln), GAA (Glu), GAG (Glu), GGA (Gly), GGC (Gly), GGG (Gly), GGT (Gly), CAC (His), CAT (His), ATC (Ile), ATT (Ile), CTC (Leu), CTG (Leu), CTT (Leu), TTG (Leu), AAA (Lys), AAG (Lys), TTC (Phe), TTT (Phe), CCA (Pro), CCC (Pro), CCT (Pro), TCA (Ser), TCC (Ser), TCT (Ser), AGC (Ser), AGT (Ser), ACA (Thr), ACC (Thr), ACT (Thr), TAC (Tyr), TAT (Tyr), GTC (Val), GTG (Val), GTT (Val), to which rule ii. above should of course be applied. Examples of a gene obtained in accordance with this variant of implementation comprise in particular the LacZΔCpG gene (positions 3 to 3056 of SEQ ID No 9; cf. example 5).

Preferably, said choice of codon will also be made so as to avoid structures which are unfavorable for the messenger RNA, such as the presence of splice sequences, of direct or inverted repeat sequences, of stem-loop structures or of polyadenylation signals. The number and the size variety of the genes synthesized by this method are illustrated in the examples below, which show that it is thus possible to envision the synthesis of genes completely devoid of CpG which nevertheless remain functional in *E. coli*. As a reference protein, any protein which can be expressed by *E. coli* can be chosen, for example a protein encoded by a gene for resistance to an antibiotic, such as the genes for resistance to zeocin® (phleomycin), to hygromycin, to blasticidin or to puromycin, or a protein encoded by reporter genes such as lacZ.

The present application is also directed toward such a method for obtaining genes devoid of CpG, which can be expressed in *E. coli*, and also any gene of at least 250 bp which can be obtained using this method. More particularly, the present application is directed toward:

- any gene the sequence of which comprises the sequence SEQ ID No. 1 from position 3 to position 374 (FIG. 1), the sequence SEQ ID No. 3 from position 3 to position 1025 (FIG. 3), the sequence SEQ ID No. 5 from position 3 to position 422 (FIG. 5), the sequence SEQ ID No. 7 from position 3 to position 599 (FIG. 7), and also any use of these genes as selection markers, and
- any gene the sequence of which comprises the sequence SEQ ID No. 9 from position 3 to position 3056 (cf. FIG. 9), and any gene the sequence of which comprises the sequence SEQ ID No. 316 (positions 3 to 797 of the DNA sequence presented in FIG. 18 (encoding SEQ ID No. 317)), and also any use of such a gene as a reporter gene.

The expression of a plasmid gene also requires having promoters suitable for the cell harboring the plasmid. The fact that the *E. coli* genome has been entirely known for a few years has facilitated the study of various noncoding elements exhibiting specific functions. Results from studies relating to the nature of the *E. coli* promoters are continually being updated and made public on the PromEC site accessible via the Internet (http://bioinfo.md.huji.ac.il/marg/promec). An analysis of the 471 well-defined promoters from base −75 to +25 relative to the transcription initiation point +1 reveals that only 6 of them do not possess CpG. The addition of each one of the 6 promoters synthesized chemically and placed upstream of the lacZ gene encoding *E. coli* β-galactosidase has proved to be negative for detection of the activity of this reporter gene. The lack of strong homology with the consensus sequences of the −10 and −35 canonic boxes suggests that these promoters are low strength promoters and, alternatively, that said promoters might be regulated by induction conditions yet to be defined for each one of them. An analysis of the well-characterized promoters of *E. coli* has revealed that only about 10 do not contain any CpG in the specific boxes for recognition by RNA polymerase. A bibliographical search has also revealed that these promoters are all inducible by various stimuli, a situation which is sometimes desired but most often relinquished for expression which is constitutive in nature. As regards the inventors, they have succeeded, by random PCR assembly of fragments exhibiting short consensus sequences devoid of CpG, drawn from several strong promoters, in developing novel promoters which are suitable for the expression of genes without CpG in *E. coli*, and which have the particular advantage of being very strong constitutive promoters and of being completely devoid of CpG. Example 6 below illustrates the construction of the novel promoter EM2K using this technology. The present application is more particularly directed toward any promoter, the sequence of which comprises the sequence SEQ ID No. 11 (cf. FIG. 11).

The characterized transcription terminators in *E. coli* are made of short sequences, several of which do not possess any CpG, and the inventors have been able to verify that such terminators effectively perform their function when they are associated, in *E. coli*, with a CpG-free promoter and gene according to the invention.

The present application is thus directed toward any transcriptional unit which comprises at least one CpG-free gene according to the invention, and at least one CpG-free promoter according to the invention. Such a transcriptional unit may also comprise at least one CpG-free terminator. The invention thus provides, for the first time, a nucleotide group which is completely devoid of CpG, and which can nevertheless be expressed in *E. coli*, performing its normal functions therein.

The present application is thus directed toward any plasmid which comprises an origin of replication according to the invention. Such plasmids may also comprise a CpG-free gene according to the invention and/or a CpG-free promoter according to the invention and/or a CpG-free transcription terminator, or a transcriptional unit according to the invention. The plasmids according to the invention therefore have the advantage of being able to exhibit no CpG in their structure, while at the same time still being capable of performing expression vector functions. Examples of such plasmids are given in the examples below.

The present application is more particularly directed toward any plasmid of SEQ ID No. 14 (FIG. 15).

Any cell transformed with at least one element selected from the group consisting of the CpG-free genes according to the invention, the CpG-free promoters according to the invention, the CpG-free origins of replication according to the invention and the CpG-free plasmids according to the invention also falls within the field of the present application. Such a cell according to the invention may also comprise a gene encoding a pi protein, such as wild-type pir or mutated pir, pir 116. Advantageously, a transformed cell according to the invention is an *E. coli* cell.

To replicate a sufficient number of functional copies of a plasmid according to the invention, those skilled in the art have at their disposal many bacteria, such as, for example, *E. coli* K12 bacteria which are conventionally used for the purposes of plasmid replication. The original K12 strain of *E. coli* has a DNA methylase which introduces a methyl group onto all the cytosines placed in the context CC(A/T)GG of the genomic and plasmid DNAs of the bacterium. All of the various strains of the K12 line have this activity due to a methylase encoded by the dcm gene (Palmer B. R. and Marinus M. G. (1994) *Gene* 143, 1-12). Since methylation of the plasmid DNAs prepared from $dcm^+$ strains of *E. coli* leads to a modification of the DNA molecule which is undesirable for the transfer of genes into eukaryote cells, the inventors have developed a strain which makes it possible both for plasmids with the CpG-free R6K gamma origin in accordance with the invention to function, and plasmid DNA devoid of methylation on the dcm sites to be obtained. For this, a new gene was constructed by the inventors, by deleting the dcm gene from position +3 after the ATG to position −14 before the TGA in the dcm gene of a pir 116 strain (cf. Example 10 below).

The dcm gene is located in a chromosomal region the sequence of which can be obtained via GenBank with the accession number D90835 (cloneKohara #344: 43.5-43.9 min).

A deletion in the gene (−) introduces the additional advantage of avoiding any reversion of the gene to the wild-type form. $dcm^-$ mutant strains have thus been produced by the inventors; they exhibit no negative phenotype which might impair bacterial growth or modify the quality and quantity of the plasmid DNA. More particularly, an optimized strain of *E. coli* has been constructed by targeted inactivation of the dcm gene using a parent strain expressing a mutated pi protein at a site leading to an increase in the number of copies of CpG-free plasmids. This optimized strain allows quality and abundant production of the plasmid DNAs which are the subjects of this invention, and which are devoid of CpG and free of methylation on the cytosines of the dcm sites. The present application is therefore directed toward any cell comprising a gene encoding the pi protein, which is transformed with the deleted dcm gene according to the invention, and any method of replicating plasmids, which comprises transforming such a cell with a plasmid, and culturing the transformed cell under conditions suitable for replication of this plasmid.

The present application is thus directed toward a method for producing a plasmid completely devoid of CpG and free of methylation on cytosine in the nucleic acid context CC(A/T)GG, characterized in that a plasmid according to the invention is produced by replication in an *Escherichia coli* strain expressing the pi protein, which is deficient for the dcm methylation system.

Any kit for producing plasmids, which comprises at least one cell according to the invention, also falls within the field of the present application. These kits are particularly suitable for the replication of plasmids according to the invention, in order to avoid these plasmids, the structure of which is devoid of CpG, being, moreover, methylated on CC(A/T)GG during their replication.

The invention thus provides a complete set of transformation means devoid of CpG; CpG-free genes, CpG-free promoters, CpG-free transcriptional units, CpG-free origins of replication for plasmid, CpG-free plasmids, cells specially suited to replication of plasmids without methylation of cytosines. These novel means find direct applications for genetic transformation of cells for biotechnological or medical purposes. Such products are in fact exceptionally well suited to the production of DNA vaccine compositions intended for humans or animals.

BRIEF DESCRIPTION OF THE DRAWINGS

The invention is illustrated by the following examples, in which reference is made to the figures:

FIG. 1: Sequence of the Sh ble ΔCpG gene (CpG-free),

FIG. 2: List of the oligonucleotides used for assembling the Sh ble ΔCpG gene, FIG. 3: Sequence of the Hph ΔCpG gene, FIG. 4: List of the oligonucleotides used to assemble the Hph ΔCpG gene, FIG. 5: Sequence of the Bsr ΔCpG gene, FIG. 6: List of the oligonucleotides used to assemble the Bsr ΔCpG gene, FIG. 7: Sequence of the Pac ΔCpG gene, FIGS. 8*a* , 8*b* and 8*c*: List of the oligonucleotides used to assemble the Pac ΔCpG gene, FIGS. 9*a* and 9*b*: Sequence of the LacZ ΔCpG gene, FIG. 10A: List of the oligonucleotides used to assemble the first third of the LacZ ΔCpG gene, FIGS. 10*b*-1 and 10*b*-2: List of the oligonucleotides used to assemble the second third of the LacZ ΔCpG gene, FIG. 10C: List of the oligonucleotides used to assemble the third third of the LacZ ΔCpG gene, FIG. 11: Sequence of the EM7 promoter (1−), and of the degenerative oligonucleotides (2−) used to construct the EM2K promoter devoid of CpG (3−), FIG. 12: Sequence of the R6K gamma M2A origin of replication, FIG. 13: List of the oligonucleotides used to assemble the R6K gamma M2A origin of replication, FIGS. 14*a*, 14*b* and 14*c*: Sequence of the R6K gamma origin of the plasmid pGTR6Kneoc9 delimited by the PacI sites, FIG. 15: Sequence of the plasmid pSh-LacZΔCpG gene, FIG. 18: Sequence of the NeoΔCpG gene (CpG-free) [position 3 to 797 of DNA sequence =SEQ ID No. 316; protein sequence =SEQ ID No. 317), FIG. 19: Sequence of the oligonucleotides SEQ ID No. 318 to SEQ ID No. X used to assemble the NeoΔCpG gene.

EXAMPLE 1

Figure 16:
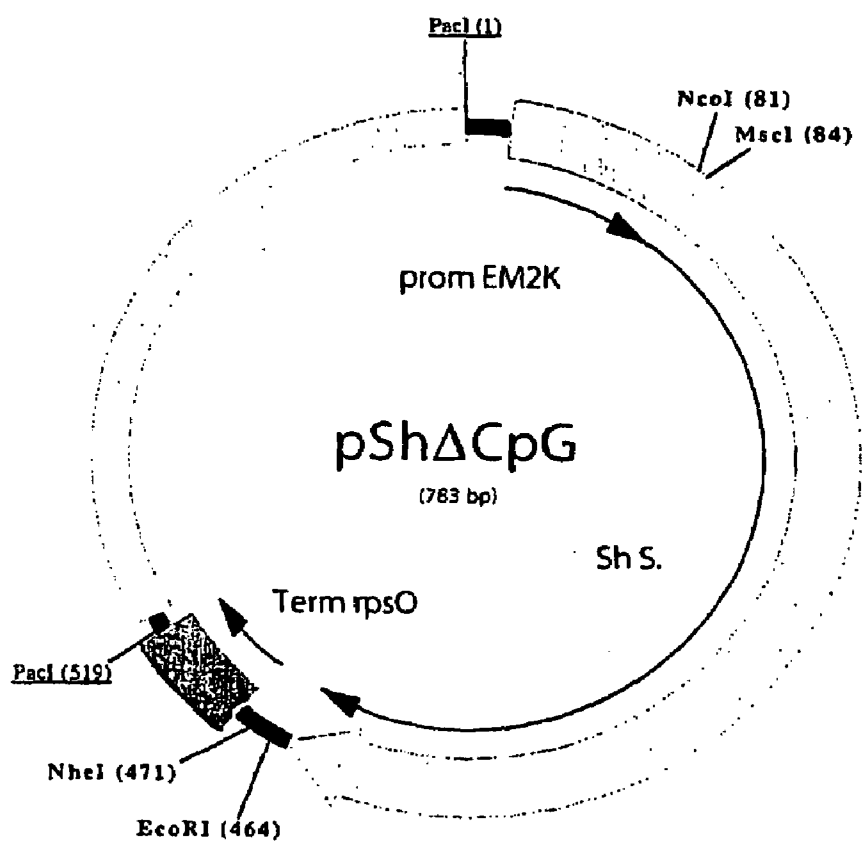
FIG. 16: Map of the plasmid pShΔCpG.

Construction of the Sh ble Gene for Resistance to Zeocin Devoid of CpG

The Sh ble ΔCpG gene, the sequence of which is given in FIG. 1 (positions 3 to 377 of SEQ ID No. 1) was synthesized from an assembly of overlapping oligonucleotides (20-40 pb in size), the sequences of which are given in FIG. 2. The assembly method is carried out in three steps; the first step consists of phosphorylation of the oligonucleotides of the coding strand, in a second step, all the oligonucleotides of both strands are combined by hybridization and ligation and, in the final step, the gene is amplified by PCR. This method was successfully used to synthesize all the synthetic genes mentioned in Examples 1, 2, 3, 4 and 5. Details of the method are given for the Sh ble ΔCpG gene:

The 10 oligonucleotides, from OL26199 to OL27099 (FIG. 2), corresponding to the coding strand, are phosphorylated according to the following procedure: 1 μl of each one of the oligonucleotides taken up in water at 250 μM are mixed in a microtube containing 15 μl of water so as to bring the final solution to a concentration of 100 picomol per microliter. 5 μl of this solution are then mixed with 10 μl of 0.10-times concentrated polynucleotide kinase buffer, 0.4 μl of a 50 mM ATP solution, 85 μl of water and 1 μl of the enzyme (at 10 μ/μl), and the entire mixture is incubated for 4 hours at 37° C. (solution A).

A solution of the oligonucleotides of the noncoding strand is made up by mixing 1 μl of each oligonucleotide (OL27199 to OL28199; cf. FIG. 2) and 1 μl of the oligonucleotide OL26099 (FIG. 2), to which solution 43 μl of water are added in order to obtain a final solution at 54 picomol per μl (solution B).

Assembly of the gene is carried out first by mixing 10 μl of solution A, 1 μl of solution B, 6 μl of a 100 mM KCl solution, 3 μl of a 0.5% NP-40 solution, 4 μl of a 50 mM $MgCl_2$ solution, 3 μl of a 10 mM ATP solution and 7.5 μl of Pfu ligase (30 units), and the mixture is then heated in a programmable thermocycler for 3 minutes at 95° C. and then 3 minutes at 80° C., before undergoing 3 cycles of one minute at 95° C., followed by a change from 95° C. to 70° C. in 1 minute, and then a change from 70° C. to 55° C. in 1 hour and, finally, 2 hours at 55° C. The mixture of the assembled oligonucleotides is then amplified with the primers OL26099 and OL27199. The amplification product is purified on a promega column, digested with the NcoI and NheI restriction enzymes, and cloned into the plasmid pMOD1LacZ(wt) linearized with NcoI and NheI. The sequences of the plasmid DNA of 2 zeocin-resistant clones which appeared after transformation of the *E. coli* strain GT100 (available from Invivogen) with the mixture of the ligation between the vector fragment and the PCR fragment, were found to be in accordance with the desired sequence given in FIG. 1. This synthetic gene, placed under the control of the bacterial EM7 promoter (vector pMOD1Sh ΔCpG) confers a zeocin resistance identical to that provided by the same vector containing the native Sh ble gene with the recipient *E. coli* strain GT100.

EXAMPLE 2

Construction of the Hph Gene for Resistance to Hygromycin Devoid of CpG

The synthetic Hph ΔCpG (sequence SEQ ID No. 3 given in FIG. 3) was constructed according to the method described in Example 1. The two strands were synthesized using oligonucleotides of 60 bases plus two oligonucleotides of 30 bases with an overlapping region of 30 bases. The assembly of the various oligonucleotides given in FIG. 4 was carried out through a final PCR with the sense oligonucleotide TTCAGCTGAGGAGGCACATC (SEQ ID No. 299) and the reverse oligonucleotide CTCAGGATC-CGCTAGCTAAT (SEQ ID No. 300) according to the experimental conditions mentioned in the preceding example.

The amplified and purified fragment (1068 pb) was then digested with the BspHI and NheI restriction enzymes and cloned into the vector pMOD2 LacZ(wt), in which the NcoI site of pMOD1 is replaced with the BspHI site. The *E. coli* clones containing this recombinant vector were selected on FastMedia™ Hydro Agar medium (Cayla). The sequence SEQ ID No. 3 in FIG. 3 was confirmed by sequencing on both strands of the plasmid DNA of two hygromycin-resistant clones. This synthetic gene, placed under the control of bacterial EM7 promoter (vector pMOD2 Hph ΔCpG), confers a hygromycin B resistance which is at least equal to that provided by the same vector containing the native Hph gene with the recipient *E. coli* strain GT100.

EXAMPLE 3

Construction of the Bsr Gene for Resistance to Blasticidin Devoid of CpG

The Bsr ΔCpG gene, the sequence of which is given in FIG. 5 (SEQ ID No. 5), was synthesized using the oligonucleotides indicated in 6, by following the method described in Example 1. The mixture of the assembled oligonucleotides was amplified with the primers OL64 and OL76 (cf. FIG. 6). The amplified and purified fragment was then digested with the BspHI and NheI restriction enzymes and cloned into the vector pMOD2 LacZ(wt). The *E. coli* clones containing this recombinant vector were selected on FastMedia™ Blasti Agar medium (Cayla). The sequence SEQ ID No. 5 in FIG. 5 was confirmed by sequencing on both strands of the plasmid DNA of two blasticidin-resistant clones.

This synthetic gene, placed under the control of the bacterial EM7 promoter (vector pMOD2 Bsr ΔCpG), confers resistance to blasticidin which is identical to that provided by the same vector containing the native Bsr gene with the recipient *E. coli* strain GT100.

EXAMPLE 4

Construction of the Pac Gene for Resistance to Puromycin Devoid of CpG

The BspHI-NheI fragment (Pac ΔCpG gene; SEQ ID No. 7), the sequence of which is given in FIG. 7, was synthesized by assembling the oligonucleotides indicated in FIG. 8.

The mixture of the assembled oligonucleotides was amplified with the sense primer pur24 (AGGACCATCATGACTGAG; SEQ ID No. 301) and the reverse primer pur25 (ATCATGTCGAGCTAGCTC; SEQ ID No. 302). The purified BspHI-NheI fragment was cloned into the plasmid pMOD2LacZ (wt) between the BspHI and NheI sites. The sequences of the plasmid DNA of 2 puromycin-resistant clones of the GT100 strain, which appeared on the FastMedia™ puro Agar medium (Cayla) after transformation by the product of the ligation between the vector fragment and the PCR fragment, were found to be in accordance with the desired sequence given in FIG. 7. The synthetic Pac ΔCpG gene, placed under the control of the bacterial EM7 promoter (vector pMOD2 Pac ΔCpG), confers a puromycin resistance which is slightly greater than that provided by the same vector containing the native pac gene with the recipient *E. coli* strain GT100.

EXAMPLE 5

Construction of the LacZ Gene Devoid of CpG Encoding β-Galactosidase of *E. coli*

The synthetic LacZ ΔCpG gene (SEQ ID No. 9 given in FIG. 9) was constructed according to the method described in the preceding examples. Given the size of the gene to be produced (more than 3000 pb), the construction was carried out in 3 distinct parts, conserving the EcoRV and SacI restriction sites at the same sites as on the native sequence of the lacZ gene. For each part, the two strands were synthesized using oligonucleotides of 40 bases plus two oligonucleotides of 20 bases with an overlapping region of 20 bases.

The first region corresponds to the NcoI-EcoRV fragment (Part I), the second region corresponds to the EcoRV-SacI fragment (Part II) and the third region corresponds to the SacI-NheI fragment. The assembly of the various oligonucleotides given in FIGS. 10A (oligonucleotides used to assemble part I), 10B (oligonucleotides used to assemble part II), and 10C (oligonucleotides used to assemble part III) was carried out by PCR according to the same experimental conditions stated in the preceding examples. The gradual cloning of the three parts of the synthetic gene was carried out in the vector pMOD1 LacZ (wt). The functionality of each cloned part and also that of the complete synthetic gene present on the vector pMOD1 LacZ was demonstrated by revealing the β-galactosidase activity on FastMedia™ Amp Xgal Agar medium (Cayla), of the recombinant clones obtained in the MC1061ΔLac strain. The complete synthetic LacZ ΔCpG gene, placed under the control of the EM7 promoter, gives 30% less β-galactosidase activity (luminometric assay of protein extracts from culture) compared to the expression of the native LacZ gene in the same plasmid environment.

EXAMPLE 6

Construction of a Strong Constitutive Promoter for *E. coli*, Devoid of CpG

The bacterial EM7 promoter present on vectors of the pMOD1 type is a synthetic promoter which is constitutive and strong in *E. coli*. Its sequence, which contains 3 CpG (SEQ ID No. 297 in FIG. 11), was used as a reference to produce a bacterial promoter devoid of CpG. We produced "linker" oligonucleotides which were degenerative at 4 places (indicated W, D, W and H on the sequence SEQ ID No. 298 in FIG. 11) and compatible with the AseI and NcoI restriction sites. These various oligos were hybridized and cloned into pMOD1 ShΔCpG between the AseI and NcoI restriction sites of the EM7 promoter. After selection of the recombinant clones on FastMedia™ Zeo Agar medium and determination of the promoter sequence of the most zeocin-resistant clone, we selected the EM2K promoter (sequence SEQ ID No. 11 in FIG. 11) as the bacterial promoter devoid of CpG.

EXAMPLE 7

Synthesis of the R6K Gamma Origins Devoid of CpG

The PacI DNA fragment containing the R6K gamma M2A origin (SED ID No. 12 in FIG. 12) was synthesized by PCR from the assembly of the oligonucleotides indicated in FIG. 13. The R6K gamma M2A fragment assembly was amplified with the primers RK15 (GCAGGACTGAGGCTTAATTAAACCTTAAAAC; SEQ ID No. 303) and RK16 (AAGTCTCCAGGTTAATTAAGATCAGCAGTTC: SEQ ID No. 304), and the fragments, after digestion with the PacI enzyme, were cloned into a plasmid (pGTCMVneo) containing the kanamycin resistance gene and the pUC origin of replication bordered by 2 PacI sites. Many transformants of the GT97 strain (which expresses the pi protein) were analyzed and only clones containing a high-copy plasmid conserved after several rounds of subculturing in the absence of kanamycin were selected. After sequencing, it was found that the ori fragment of most of these plasmids could have a lower number (5-6) of repeat sequences, instead of the 7, of the natural origin of the R6K plasmid. One of these novel sequences of the synthetic R6K gamma origin devoid of CpG is given in SEQ ID No. 13 in FIG. 14).

Two other versions of the R6K gamma origin, in which the G of each CpG present in the repeat sequences (22 bp element repeated several times in the pi protein-binding region) has been replaced with a C, to give the origin (R6K gamma M2C), or a T, to give the origin (R6K gamma M2T), were synthesized in a similar manner. The functionality of these novel R6K gamma origins in which the G of the CpGs of the repeat sequences is replaced with a C or with a T, added to the example of the origin of FIG. 13, in which the G is replaced with an A, demonstrates that the CpGs of these repeat sequences do not play a role in the functionality of the origin.

EXAMPLE 8

Assembly of Plasmid Vectors Completely Devoid of CpG, Expressing a Gene for Resistance in *E. coli*

Firstly, a PacI-PacI cassette containing the bacterial EM2K promoter and the Sh ΔCpG zeocin resistance gene followed by a CpG-free bacterial terminator was prepared. For this, "linker" oligonucleotides containing the sequence of the t1 terminator of the intergenic region rpsO-pnp of *E. coli* were hybridized and cloned between the NheI and PacI sites of the vector pMOD1 EM2K Sh ΔCpG: "linker" oligonucleotides:

```
rpsO-1 (5'->3'):
CTAGCTGAGTTTCAGAAAAGGGGGCCTGAGTGGCCCCTTTTTTCAACTTAAT  SEQ ID No. 305

rpsO-2 (5'->3'):
TAAGTTGAAAAAAGGGGCCACTCAGGCCCCCTTTTCTGAAACTCAG.       SEQ ID No. 306
```

The recombinant vector obtained (pMOD1 EM2K sH ΔCpG Term) was verified by sequencing in the region of the terminator sequence which does not naturally contain any CpG. The EM2K-Sh ΔCpG-Term cassette contained in this vector was then amplified by PCR so as to flank the two sides with PacI sites using the foll owing primers:

```
PACI-UP (5'->3'):
ATCGTTAATTAAAACAGTAGTTGACAATTAAACATTGGC     SEQ ID
                                            No. 307

PACI-DOWN (5'->3'):
ATCGTTAATTAAGTTGAAAAAAGGGGCC.               SEQ ID
                                            No. 308
```

This amplified fragment was then purified and cleaved with PacI, and then assembled with PacI fragment containing the R6K gamma ΔCpG origin described in Example 7. After transformation of this ligation mixture into the GT97 strain (which expresses the pi protein) and selection on FastMedia™ Zeo medium, analysis of the recombinant clones obtained revealed two possible orientations of the PacI-PacI fragment containing the R6K gamma ΔCpG origin. The orientation selected in pSh ΔCpG is represented in FIG. 16.

EXAMPLE 9

Assembly of a Plasmid Vector Completely Devoid of CpG, Expressing the Zeocin Resistance Gene and the β-Galactosidase Gene in *E. coli.*

The vector pSh ΔCpG described in Example 8 (FIG. 16) was used to insert the synthetic LacZ gene devoid of CpG between the EcoRI and NheI sites. For this, EcoRI- and NcoI-compatible "linker" oligonucleotides containing a ribosome-binding site consensus sequence from *E. coli* were hybridized and cloned with the NcoI-NheI LacZΔCpG fragment of pMOD1 LacZΔCpG, between the EcoRI and NheI sites of the vector pMOD1 EM2K ShΔCpG. "linker" oligonucleotides used:

```
rbs-1   (5'->3'): AATTCTGAGGAGAAGCT  SEQ ID No. 309

rbs-2   (5'->3'): CATGAGCTTCTCCTCAG  SEQ ID No. 310
```

Figure 17:
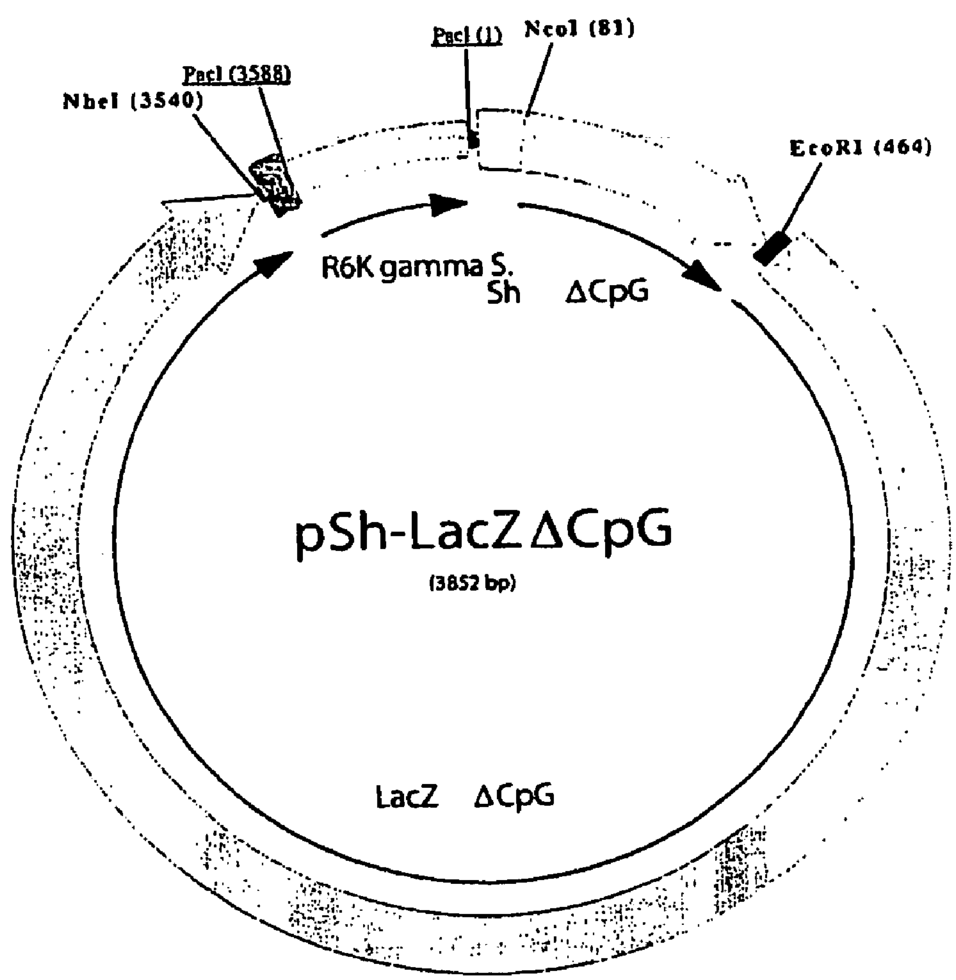
FIG. 17: Map of the plasmid pSh-LacZΔCpG.

Transformation of this ligation mixture into the GT97 strain (which expresses the pi protein) and selection on FastMedia™ Zeo Xgal medium made it possible to obtain the recombinant clones containing the vector pSh-LacZΔCpG (FIGS. 15 and 17). This vector co-expresses, under the control of the bacterial EM2K promoter, in an artificial operon system, the ShΔCpG and LacZΔCpG genes.

EXAMPLE 10

Production of an *E. coli* Strain Expressing the Mutant Protein pi116 and Carrying a Deletion in the dcm Gene The pir gene encoding the pi protein which is essential for initiating replication of the R6K gamma origin, and also the mutated gene pir116 which leads to an increase in the number of copies of R6K gamma plasmids, have been introduced, in a functional form, into various *E. coli* K12 strains by various groups. Strains of this type can be obtained from the *E. coli* Genetic Stock Center (http://cgsc.biology.yale.edu), and are also commercially available from companies specializing in supplying biological material for research. This is the case, for example, of the pir1 (pir116) and pir2 (wild-type pir) strains provided by the company Invitrogen, whose products can be purchased in all European countries. The GT97 strain of the K12 line, which has the genotype Δlac169 hsdR514 endAl recAl codBa uidA (ΔMlul)::pir 116 (available from InvivoGen), was chosen for its simplicity, the consistency of the R6K gamma plasmid DNA preparations and its high levels of competence, from several K12 pir strains of distinctive genotype for some genes. The introduction of a deletion into the dcm gene of the GT97 strain was carried out in the following way:

Two DNA regions, of 1.8 kb and 1.5 kb, flanking respectively the ATG initiation codon (fragment A) and the TGA stop codon (fragment B) of the dcm gene were amplified by PCR. The fragment A was then amplified with the pair of primers OLdcmAF (TTTT GCGGCCGCTTGCTGCGCCAGCAACTAATAACG; SEQ ID No. 311) and OLdcmAR (CCTT GGATCCTGGTAAACACGCACTGTCCGCCAATCGA TTC; SEQ ID No. 312) and fragment B was amplified with the pair of primers OLdcmBF (TTTT GGATCCTCAGCAAGAGGCACAACATG; SEQ ID No. 313) and OLdcmBR (TTTT CTCGAGAAACGGCAGCTCTGATACTTGCTTC; SEQ ID No. 314). The restriction sites for the NotI (GCGGC-CGC), BamHI (GGATCC) and XhoI (CTCGAG) enzymes were introduced into the primers in order to combine fragment A and fragment B with one another, forming a genetic element flanked by the NotI and XhoI sites. The region of the dcm gene is thus reconstituted, creating a deletion which stems from position +3 after the ATG to position −14 before the TGA. This genetic element was cloned into pKO3 (Link A. J., Phillips D. and Church G. M. (1997) *J Bacteriol* 179, 6228-37), a vector developed for allele replacement in *Escherichia coli*, with thermosensitive replication, between the NotI and SalI sites, to give the plasmid named pKO3Δdcm. The GT97 strain was co-transformed with this plasmid and with a plasmid which expresses the RecA protein (pFL352). A transformant containing the two plasmids was cultured at a nonpermissible temperature (42° C.) in the presence of chloramphenicol in order to select clones which have integrated pKO3Δdcm into the bacterial chromosome by homologous recombination. A subclone resistant to chloramphenicol at 42° C. was then cultured at 30° C. on a medium containing a high concentration of sucrose (5%) in order to counter-select the strains which, after a second homologous recombination event, have exchanged the chromosomal region of the dcm gene with the homologous fragment cloned into the plasmid. The deletion introduced into the selected clone (GT106) was verified by PCR with the pair of primers OldcmAF and OldcmBR, generating a fragment smaller in size than that obtained with the parental strain, and by a PCR with the primer OldcmBR and a primer positioned outside the exchanged region (OldcmCF TTTTGCGGCCGCGTTGCGGTATTACCCTTGTC; SEQ ID No. 315).

The dcm$^-$ genotype of the GT106 strain was confirmed by introducing into said strain and into GT106, a plasmid containing a restriction site for the SexAI enzyme, which is subject to dcm methylation. The plasmid purified from GT106 is cleaved by SexAI, whereas it is resistant to the enzyme when it is purified from GT97.

The latter strain named GT106 exhibits the same growth characteristics as the parental strain GT97 and, as expected, no negative modification of the amount of R6K gamma plasmid DNAs was observed, only the quality of the DNAs, assessed by the absence of methylation of the cytosines of the dcm sites, was improved. The GT106 strain will be available from the company Invivogen from the day on which this patent application is filed.

EXAMPLE 11

Production of the Neo Gene for Resistance to Neomycin, Devoid of CpG

The Neo ΔCpG gene, the sequence of which is given in FIG. 18 (position 3 to 797 of the DNA sequence given in FIG. 18=SEQ ID No. 316; protein sequence ═SEQ ID No. 317), was synthesized from an assembly of overlapping oligonucleotides (20-40 pb in size), the sequences of which are given in FIG. 19. The assembly method is carried out in three steps; the first step consists of phosphorylation of the oligonucleotides of the coding strand, in a second step, all the oligonucleotides of both strands are combined by hybridization and ligation and, in the final step, the gene is amplified by PCR.

The 20 oligonucleotides of SEQ ID No. 319 to SEQ ID No. 338 (FIG. 19) corresponding to the coding strand are phosphorylated according to the following procedure: 1 μl of each one of the oligonucleotides, taken up in water at 250 μM, are mixed in a microtube containing 50 μl of water, so as to bring the final solution to a concentration of 100 picomol per microliter. 5 μl of this solution are then mixed with 10 μl of 10-times concentrated polynucleotide kinase buffer, 0.4 μl of a 50 mM ATP solution, 85 μl of water and 1 μl of the enzyme (at 10 μ/μl), and the entire mixture is incubated for 4 hours at 37° C. and then 5 minutes at 95° C. (solution A).

A solution of the oligonucleotides of the noncoding strand is made up by mixing 1 μl of each oligonucleotide (SEQ ID No. 339 to SEQ ID No. 360; FIG. 19) and 1 μl of the oligonucleotide SEQ ID No. 318 (FIG. 19), to which solution 160 μl of water are added in order to obtain a final solution at 54 picomol per μl (solution B).

The assembly of the gene is carried out first by mixing 10 μl of solution A, 1 μl of solution B, 6 μl of a 100 mM KCl solution, 3 μl of a 0.5% solution of the surfactant NP-40, 4 μl of a 50 mM $MgCl_2$ solution, 3 μl of a 10 mM ATP solution and 7.5 μl of Pfu ligase (30 units), and the mixture is then heated in a programmable thermocycler for 3 minutes at 95° C. and then 3 minutes at 80° C., before undergoing 3 cycles of one minute at 95° C., followed by a change from 95° C. to 70° C. in 1 minute, then a change from 70° C. to 55° C. in 1 hour and, finally, 2 hours at 55° C. The mixture of the assembled oligonucleotides is then amplified with the primers NO1 and $NO_{22}$. The amplification product is purified on a Promega column, digested with the BspHI and NheI restriction enzymes and cloned into the plasmid pMOD2LacZ(wt) linearized with BspHI and NheI. The sequences of the plasmid DNA of 2 kanamycin-resistant clones, which appeared after transformation of the *E. coli* strain GT100 (available from Invivogen) with the mixture of the ligation between the vector fragment and the PCR fragment, were found to be in accordance with the sequence given in FIG. 18. This synthetic gene, placed under the control of the bacterial EM7 promoter (vector pMOD2Neo ΔCpG), confers a resistance to kanamycin identical to that provided by the same vector containing the native neo gene with the recipient *E. coli* strain GT100. The BspHI-NheI neo fragment of the plasmid pMOD2Neo ΔCpG was then introduced into the plasmid pSh ΔCpG of FIG. 16, linearized with NcoI-NheI, to give, after ligation and transformation in *E. coli*, the plasmid pNeoΔCpG.

The invention claimed is:

1. An origin of replication for a plasmid, wherein its sequence corresponds to that of the R6K gamma origin of replication in which each G of the CpGs of the repeat region of the core has been replaced with an A, a C or a T, or each C of the CpGs has been replaced with a G, an A or a T.

2. The origin of replication as claimed in claim 1, wherein its sequence comprises the sequence SEQ ID NO: 12 or the sequence SEQ ID NO: 13.

3. The origin of replication as claimed in claim 1, wherein the pi protein-binding sequence is repeated 5 or 6 times.

4. A promoter, whose sequence comprises the sequence SEQ ID NO: 11.

5. A plasmid comprising an origin of replication as claimed in claim 1.

6. The plasmid as claimed in claim 5, being completely devoid of CpG.

7. A plasmid of SEQ ID NO: 14.

8. A method for producing a plasmid completely devoid of CpG and free of methylation on cytosine in the nucleic acid context CC(A/T)GG, wherein a plasmid as claimed in claim 5 is produced by replication in an *Escherichia coil* strain expressing the pi protein, which is deficient for the dcm methylation system.

9. An *Escherichia coil* cell transformed with the plasmids as claimed in claim 5.

10. The transformed *Escherichia coil* cell as claimed in claim 9, wherein it expresses a gene encoding a pi protein.

11. The transformed *Escherichia coli* cell as claimed in claim 10, which further comprises an inactivated dcm gene.

12. A kit for producing plasmids, comprising at least one cell as claimed in claim 9.

* * * * *